US006500626B1

(12) United States Patent
Korsmeyer

(10) Patent No.: US 6,500,626 B1
(45) Date of Patent: Dec. 31, 2002

(54) CELL DEATH REGULATORS

(75) Inventor: Stanley J. Korsmeyer, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 09/379,820

(22) Filed: Aug. 24, 1999

Related U.S. Application Data

(62) Division of application No. 08/856,034, filed on May 14, 1997, now Pat. No. 5,955,595, which is a continuation of application No. 08/112,208, filed on Aug. 26, 1993, now Pat. No. 5,691,179.

(51) Int. Cl.$^7$ .................................... G01N 33/53

(52) U.S. Cl. ........................ 435/7.8; 435/7.1; 435/6; 436/501

(58) Field of Search ........................ 435/7.1, 7.8, 6; 436/501

(56) References Cited

PUBLICATIONS

Callard et al. The Cytokine Facts Book. New York: Academic Press, p. 31.*

Cleary et al., Cloning and Structural Analysis of cDNAs for bcl–2 and a Hybrid bcl–2/Immunoglobulin Transcript Resulting from the t(14;18) Translocation, *Cell 47*:19–28 (1986).

Hockenbery, Bcl–2 is an inner mitochondrial membrane protein that blocks programmed cell death, *Nature 348*:334–336 (1990).

Hockenbery, BCL2 protein is topographically restricted in tissues characterized by apoptotic cell death, *Proc. Natl. Acad. Sci. USA 88*:6961–6965 (1991).

Hockenbery, et al., Bcl–2 Functions in an Antioxidant Pathway to Prevent Apoptosis, *Cell 75*:241–251 (1993).

Korsmeyer, Bcl–2: A repressor of lymphocyte death, *Immunol. Today 13*:285–288 (1992).

Korsmeyer, Bcl–2: An antidote to Programmed Cell Death, *Cancer Surveys 15*:105–118 (1992).

Korsmeyer, Bcl–2 Initiates a New Category of Oncogenes: Regulators of Cell Death, *Blood 80*(40):879–886 (1992).

Kozopas et al., MCL 1, a gene expressed in programmed myeloid cell differentiation, has sequence similarity to BCL2, *Proc. Natl. Acad. Sci. USA 90*:3516–3520 (1993).

Lipford et al., Refinement of Lymphoma Cytogenetics by the Chromosome 18q21 Major Breakpoint Region, *Blood 70*:1816–1823 (1987).

McDonnell et al., Bcl–2–Immunoglobulin Transgenic Mice Demonstrates Extended B Cell Survival and Follicular Lymphoproliferation, *Cell 57*:79–88 (1989).

McDonnell et al., Deregulated Bcl–2–Immunoglobulin Transgene Expands a Resting but Responsive Immunoglobulin M and D–Expressing B–Cell Population, *Mol. & Cell Biol. 10*(5):1901–1907 (1990).

McDonnell et al., Progression from lymphoid hyperlasia to high–grade malignant lymphoma in mice transgenic for the t(14;18), *Nature 349*:254–256 (1991).

McKearn et al., Enrichment of hematopoietic precursor cells and cloning of multipotential B–lymphocyte precursors, *Proc. Nat. Acad. Sci., USA 82*:7414–7418 (1985).

Nakayama, Disappearance of the Lymphoid System in Bcl–2 Homozygous Mutant Chimeric Mice, *Science 261*:1584–1588 (1993).

Nunez et al., Deregulated Bcl–2 Gene Expression Selectively Prolongs Survival of Growth Factor–Deprived Hemopoietic Cell Lines, *J. Immun. 144*(9):3602–3610 (1990).

Oltval et al., Bcl–2 Heterodimerizes in Vivo with a Conserved Homolog, Bax, That Accelerates Programmed Cell Death, *Cell 74*:609–619 (1993).

Sentman, Bcl–2 Inhibits Multiple Forms of Apopotosis by Not Negative Selection in Thymocytes, *Cell 67*:879–888 (1991).

Silverman et al., Meiotic recombination between yeast artifical chromosomes yields a single clone containing the entire BCL2 protooncogene, *Proc. Natl. Acad. Sci. USA 87*:9913–9917 (1990).

Veis et al., Bcl–2 Deficient Mice Demonstrate Fulminant Lymphoid Apoptosis, Polycystic Kidneys, and Hypopigmented Hair, *Cell 75*:229–240 (1993).

Yin et al., BH1 and BH2 domains of BCL–2 are required for inhibition of apoptosis and heterodimerization with Bax, *Nature 369*:321–323 (1994).

Yin et al., BCL–2 functions by counteracting its dimerization partner, BAX, a death accelerator protein, *Blood 82*(10):441A, Abstract No. 1749 (Dec., 1993).

Young et al., A negative Regulatory Element in the bcl–2 5'–Untranslated Region Inhibits Expression from an Upstream Promotor, *Mol.&Cell Biol., 13(6)*:3686–3697 (1993).

Zutter et al., Immunolocalization of the Bcl–2 Protein Within Hematopoietic Neoplasmas, *Blood 78*(4): 1062–1068 (1991).

* cited by examiner

*Primary Examiner*—Gabriele E. Bugalsky
(74) *Attorney, Agent, or Firm*—Thompson Coburn LLP

(57) ABSTRACT

A Bcl-2 associated protein (Bax) and uses thereof.

14 Claims, 25 Drawing Sheets

```
hu cDNA                                                        GAGGCGGCGGCGGGAGCGGCGGTG

                                                    1│2
hu cDNA    ATGGACGGGTCCGGGGAGCAGCCCAGAGGCGGGGGGCCCACCAGCTCTGAGCAGATCATG  60
mu protein                   LeuGlySer
hu protein METAspGlySerGlyGluGlnProArgGlyGlyGlyProThrSerSerGluGlnIleMet

                                                    2│3
hu cDNA    AAGACAGGGGCCCTTTTGCTTCAGGGTTTCATCCAGGATCGAGCAGGGCGAATGGGGGGG  120
mu protein                Phe                                     Ala
hu protein LysThrGlyAlaLeuLeuLeuGlnGlyPheIleGlnAspArgAlaGlyArgMetGlyGly

hu cDNA    GAGGCACCCGAGCTGGCCCTGGACCCGGTGCCTCAGGATGCGTCCACCAAGAAGCTGAGC  180
mu protein   Thr          Thr       GluGlnPro
hu protein GluAlaProGluLeuAlaLeuAspProValProGlnAspAlaSerThrLysLysLeuSer

                                                               3│4
hu cDNA    GAGTGTCTCAAGCGCATCGGGGACGAACTGGACAGTAACATGGAGCTGCAGAGGATGATT  240
mu protein             Arg
hu protein GluCysLeuLysArgIleGlyAspGluLeuAspSerAsnMetGluLeuGlnArgMetIle

hu cDNA    GCCGCCGTGGACACAGACTCCCCCCGAGAGGTCTTTTTCCGAGTGGCAGCTGACATGTTT  300
mu protein     Asp
hu protein AlaAlaValAspThrAspSerProArgGluValPhePheArgValAlaAlaAspMetPhe

hu cDNA    TCTGACGGCAACTTCAACTGGGGCCGGGTTGTCGCCCTTTTCTACTTTGCCAGCAAACTG  360
mu protein Ala
hu protein SerAspGlyAsnPheAsnTrpGlyArgValValAlaLeuPheTyrPheAlaSerLysLeu

                 4│5
hu cDNA    GTGCTCAAGGCCCTGTGCACCAAGGTGCCGGAACTGATCAGAACCATCATGGGCTGGACA  420
mu protein
hu protein ValLeuLysAlaLeuCysThrLysValProGluLeuIleArgThrIleMetGlyTrpThr

                                                            5●│6
hu cDNA    TTGGACTTCCTCCGGGAGCGGCTGTTGGGCTGGATCCAAGACCAGGGTGGTTGGGACGGC  480
mu protein                                                         Glu
hu protein LeuAspPheLeuArgGluArgLeuLeuGlyTrpIleGlnAspGlnGlyGlyTrpAspGly

hu cDNA    CTCCTCTCCTACTTTGGGACGCCCACGTGGCAGACCGTGACCATCTTTGTGGCGGGAGTG  540
mu protein
hu protein LeuLeuSerTyrPheGlyThrProThrTrpGlnThrValThrIlePheValAlaGlyVal

hu cDNA    CTCACCGCCTCGCTCACCATCTGGAAGAAGATGGGCTGAGGCCCCAGCTGCCTTGGACTG
mu protein
hu protein LeuThrAlaSerLeuThrIleTrpLysLysMetGly---
```

Figure 3

Exon 5 ⋮ Intron 5

```
TGGGTGAGACTCCTCAAGCCTCCTCACCCCCACCACCGCGCCCTCACCACCGCCCCTGCC 532
TrpValArgLeuLeuLysProProHisProHisHisArgAlaLeuThrThrAlaProAla

CCACCGTCCCTGCCCCCCGCCACTCCTCTGGGACCCTGGGCCTTCTGGAGCAGGTCACAG 592
ProProSerLeuProProAlaThrProLeuGlyProTrpAlaPheTrpSerArgSerGln

TGGTGCCCTCTCCCCATCTTCAGATCATCAGATGTGGTCTATAATGCGTTTTCCTTACGT 652
TrpCysProLeuProIlePheArgSerSerAspValValTyrAsnAlaPheSerLeuArg

GTCTGA 658
Val---
```

FIGURE 5

Exon 1 ⁞ Exon 3

```
ATGGACGGGTCCGGAGAGCAGCCCAGAGGCGGGGTTTCATCCAGGATCGAGCAGGGCGAA  60
MetAspGlySerGlyGluGlnProArgGlyGlyValSerSerArgIleGluGlnGlyGlu

TGGGGGGGGAGGCACCCGAGCTGGCCCTGGACCCGGTGCCTCAGGATGCGTCCACCAAGA 120
TrpGlyGlyArgHisProSerTrpProTrpThrArgCysLeuArgMetArgProProArg

AGCTGA 126
Ser---
```

| | | | |
|---|---|---|---|
| BCL2 (HUMAN) | 135 | E E L F R D G V - N W G R I V A F F E F G G | 155 |
| BAX (HUMAN) | 97 | A D M F S D G N F N W G R V V A L F Y F A S | 118 |
| MCL1 (MOUSE) | 251 | I H V F S D G V T N W G R I V T L I S F G A | 272 |
| LMW5-HL (ASFV) | 75 | T E L F K/R D L I - N W G R I C G F I V F S A | 95 |
| BHRF1 (EBV) | 88 | L E I F H R G D P S L G R A L A W M A W C M | 109 |

| | | | |
|---|---|---|---|
| BCL-2 (HUMAN) | 183 | R H L H T W I Q D N G G W D A F V E L Y G P S | 205 |
| BAX (HUMAN) | 146 | E R L L G W I Q D Q G G W D G L L S Y F G T P | 168 |
| MCL1 (MOUSE) | 300 | R T K R D W L V K Q R G W D G F V E F F - H V | 321 |
| LMW5-HL (ASFV) | 122 | H N L L P W M I G G Q E E F L A F S L H S | 144 |
| BHRF1 (EBV) | 138 | E G L D G W I H Q Q G G W S T L I E D N I P G | 160 |

FIG. 14B

| | | | |
|---|---|---|---|
| | SacI | | BamHI |
| Original: | . . . . . | E E L F R D G V N W G R I V A | . . . . . |
| mI- 1: | | - - - A A A A - - - - - - - - | |
| mI-2: | | - - - - - - - - - - A A A - - - | |
| mI-3: | | - - - - - - - - - - - A - - - - | |
| mI-4: | | - - - - - - - - - - - E - - - - | |

FIG. 14C

| | | | |
|---|---|---|---|
| | BamHI | | SphI |
| Original: | . . . . . | W I Q D N G G W D A F V E L Y | . . . . . |
| mII-2: | | - - L A A - - - - - - - - - - | |
| mII-4: | | - - - - A - - - - - - - - - - | |
| mII-3: | | - - - - - - - - * * * - - - - - - | |
| mII-5: | | - - - - - - - - - - - - - A - - | |

FL5.12 STABLES

2B4 STABLES

DOMAIN II MUTANT STABLES PROTEIN LEVELS
RELATIVE CELL NUMBER
FL5.12-M2
NEO
BCL-2WT
M2-2
M2-8
FL5.12-M4
NEO
BCL-2WT
M4-2
M4-9
2B4-M2
NEO
M2-1
BCL-2WT
M2-5
FLUORESCENCE INTENSITY

NEO
BCL-2WT
M2-2
M2-8
-30K

NEO
BCL-2WT
M4-2
M4-9
M4-10
-30K

NEO
BCL-2WT
M2-1
M2-5
-30K

Fig. 20C 2B4 DOMAIN II STABLES DEXAMETHOSONE
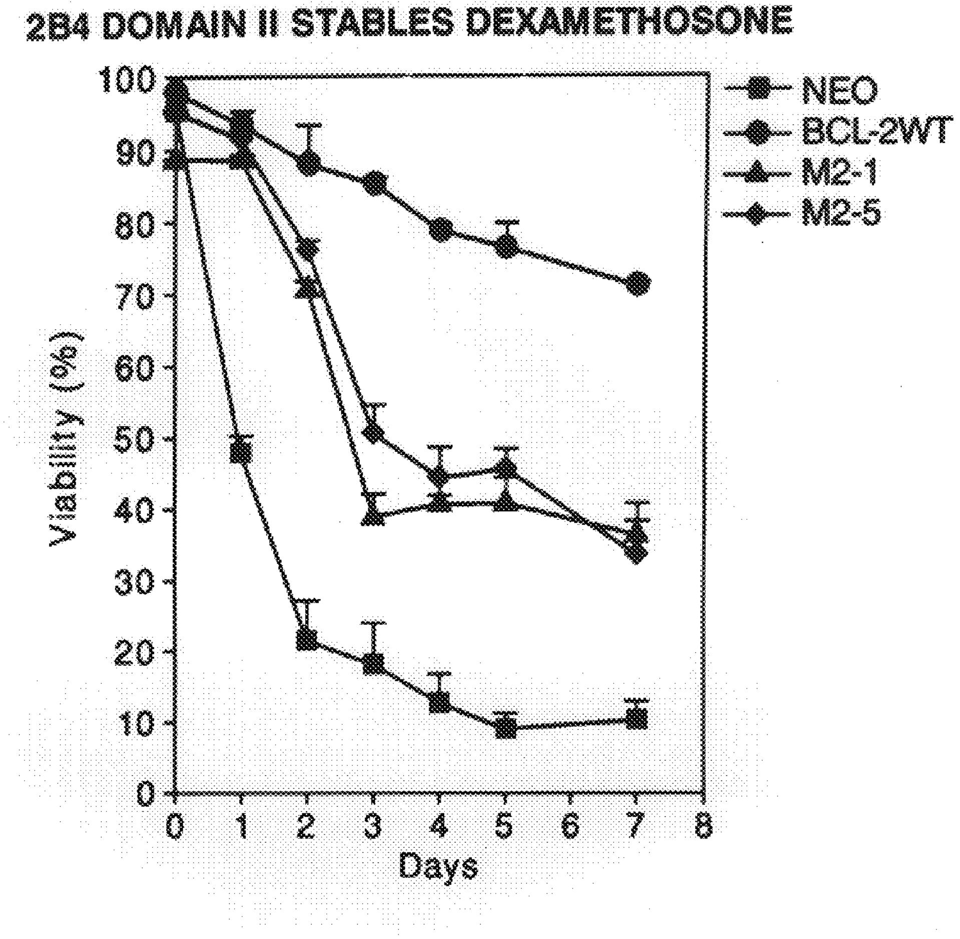
Fig. 20D
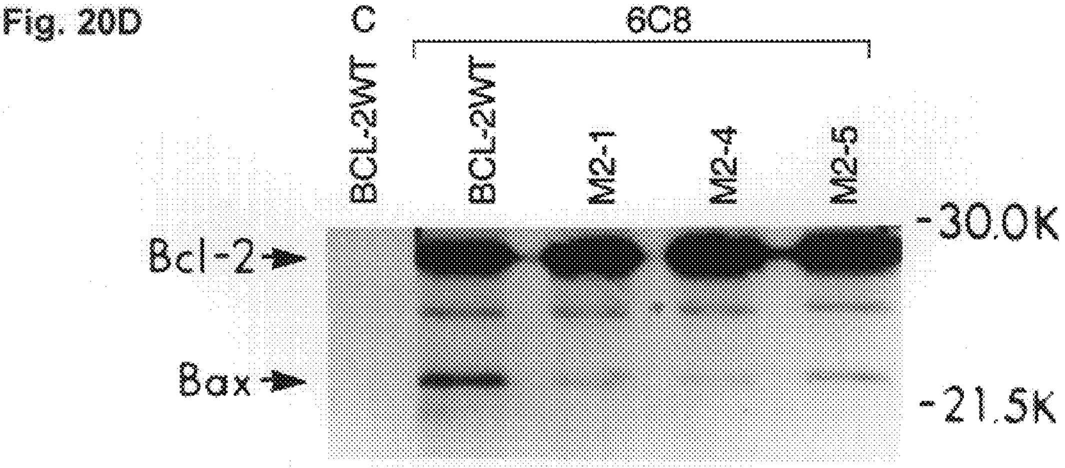

PRIMARY IMMUNOPRECIPITATE

WESTERN OF PRIMARY IMMUNOPRECIPITATION IN B

CELL DEATH REGULATORS

This is a divisional of application Ser. No. 08/856,034; filed on May 14, 1997 now U.S. Pat. No. 5,955,595 which is a continuation of Ser. No. 08/112,208 filed Aug. 26, 1993 now U.S. Pat. No. 5,691,179.

STATEMENT OF RIGHTS

The US Government has a paid-up license in this invention and the right in limited circumstances to require the patent owner to license others on reasonable terms as provided for by the terms of Grant No. 49712-05 issued by the National Institute of Health.

BACKGROUND OF THE INVENTION

1. Field Of The Invention

The invention relates to the identification, purification, and isolation of a novel protein which interacts with Bcl-2 protein to form heteromultimers (heterodimers) in vivo and more particularly to the purification, isolation and use of Bcl-2 associated protein, herein called Bax.

2. Description Of The Related Art

Cell death is an important aspect during the embryonic or post-natal development of major organ systems. Apoptosis, or programmed cell demise, also plays a critical role in maintaining homeostasis in many adult tissues. Within vertebrates; Bcl-2 is the best understood gene in a cell death pathway and functions as a cell death repressor.

Bcl-2 is unique among protooncogenes by being localized to the mitochondrial membrane as defined by Hockenbery, D. M., Nunez, G., Milliman, C., Schreiber, R. D. and Korsmeyer, S. J. "Bcl-2 is an inner mitochondrial membrane protein that blocks programmed. cell death." Nature 378, 334–336, 1990. Bcl-2 has been shown to have the oncogenic function of blocking programmed cell death whereas a deregulated Bcl-2 extends the survival of certain hematopoietic cell lines following growth factor deprivation. When pro-B-cell or promyelocyte cell lines are deprived of interleukin 3 they normally succumb to a programmed demise entitled apoptosis. This pattern of morphologic cell death is characterized by a dramatic plasma membrane blebbing, cell volume contraction, nuclear pyknosis, and internucleosomal DNA degradation following the activation of an endonuclease. Over expression of mitochondrial Bcl-2 appears to function as an antidote to this process and has the unique function of blocking programmed cell death independent of promoting proliferation.

The Bcl-2 protooncogene was discovered at the chromosomal breakpoint of the t(14;18) (q32;q21) which is the cytogenetic hallmark of human follicular lymphoma. Approximately 85% of follicular and 20% of diffuse B-cell lymphomas possess this translocation. Follicular lymphoma is often present as a low-grade malignancy composed of small resting IgM/IgD B cells. Over time, conversion to a more aggressive high-grade lymphoma with a diffuse large-cell architecture frequently occurs.

Studies of Bcl-2 emphasizes the existence of multiple pathways in the generation of neoplasia. The increased cell number in neoplastic tissue can be viewed as a violation of normal homeostasis. The maintenance of homeostasis in normal tissue, in many respects, reflects a simple balanced equation of input (cellular proliferation and renewal) versus output (cell death). This is most easily envisioned for encapsulated organs, such as the prostate, but is also true of the recirculating hematopoietic lineages. The maintenance of remarkably invariant cell numbers reflects tightly regulated death pathways as well as controlled proliferation. See for example S. J. Korsmeyer "Bcl-2 Initiates a New Category of Oncogenes: Regulators of Cell Death", Blood Vol. 80 No. 4 pp. 879–886, Aug. 15, 1992.

Programmed cell death represents a cell autonomous suicide pathway that helps restrict cell numbers. The well-defined loss of specific cells is crucial during embryonic development as part of organogenesis. In mature tissues, genetically programmed demise regulates the volume of cells. A morphologically distinct and temporally regulated cell death entitled apoptosis has been identified by Wyllie A H: "Apoptosis; Cell death in tissue regulation". J. Pathol 153:313, 1987. Cells dying by apoptosis display marked plasma membrane blebbing, volume contraction, nuclear condensation, and the activation of an endonuclease that cleaves DNA into nucleosomal length fragments.

Bcl-2 has been localized to chromosome segment 18q21.3 in a telomere to centromere orientation. The Bcl-2 gene possesses 3 exons, the first of which is untranslated. Two potential promoter regions exist. P1 is GC rich with multiple SP1 sites and is used predominantly. Bcl-2 is an enormous gene in which a 225-kb intron II divides the protein encoding exons II and III. See Silvermann G A et al. "Meiotic recombination between yeast artificial chromosomes yields a single clone containing the entire Bcl-2 proto-oncogene" Proc Natl Acad Sci 87;9913, 1990. A molecular consequence of the translation is the movement of the Bcl-2 gene to the der(14) chromosome placing Bcl-2 in the same transcriptional orientation as the Ig heavy chain locus giving rise to chimeric RNAs. However, translocation does not interrupt the protein encoding region so that normal and translocated alleles produce the same sized, 25-Kd protein.

Hematopoietic progenitors, including pro-B cells, possess high levels of Bcl-2. See Hockenbery D, Zuter M, Hickey W, Nahm M, Korsmeyer S J: "Bcl-2 protein is topographically restricted in tissues characterized by apoptotic cell death". Proc Natl Acad Sci USA 88:6961, 1991. Some mature B cells and, especially, B-cell lines have low levels of Bcl-2 RNA. In contrast, t(14;18)-bearing B cells have inappropriate elevated levels of the Bcl-2-Ig fusion RNA. Graninger W B, Seto M. Boutain B, Goldman, P, Korsmeyer S J: Expression of Bcl-2 and Bcl-2-Ig fusion transcripts in normal and neoplastic cells. J. Clin Invest 80:1512, 1987. This increased steady-state RNA reflects both increased transcription as well as a processing advantage for the Bcl-2-Ig fusion allele.

Bcl-2 has been introduced into a variety of interleukin (IL)-dependent cell lines to determine if it is involved in a growth factor pathway. See S J Korsmeyer above. Such lines were examined to determine if Bcl-2 would spare the need for a specific ligand/receptor interaction. However, no long-term growth factor-independent cell lines emerged after overexpression of Bcl-2 in IL-2, IL-3, IL-4, or IL-6 requiring lines. However, Bcl-2 conferred a death-sparing effect to certain hematopoietic cell lines after growth factor withdrawal in the IL-3-dependent early hematopoietic cell lines FDCP1, FL5.12, and 32D. This effect was not restricted to the IL-3/IL-3 receptor signal transduction pathway in that granulocyte-macrophage colony-stimulating factor (GM-CSF) and IL-4 deprived cells displayed a similar response. Yet, Bcl-2 enhanced cell survival was not universal, as neither IL-2-dependent T-cell lines nor an IL-6-dependent myeloma line showed a consistent effect upon factor withdrawal.

Bcl-2 has not been shown to directly promote cell cycle progression, nor does it necessarily alter the dose response to limiting concentrations of IL-3. See Nunez G, London L., Hockenbery D, Alexander M, McKearn J. Korsmeyer S J: "Deregulated Bcl-2 gene expression selectively prolongs survival of growth factor-deprived hemopoietic cell lines". J. Immunol 144;3602, 1990. Instead, Bcl-2 blocked the plasma membrane blebbing, volume contraction, nuclear condensation, and endonucleolytic cleavage of DNA known as apoptosis. Factor deprived cells return to Go, but do not die. However, they can be rescued after 30 days of deprivation by the addition of IL-3, indicating they are not terminally differentiated or permanently arrested.

While identifying the Bcl-2 cell death pathway is significant, a way of regulating the Bcl-2 pathway has not been discovered. The ability to down-regulate the effect of Bcl-2 would be advantageous in cancer therapy, in controlling hyperplasias such as benign prostatic hypertrophy (BPH) and eliminating self reactive clones in autoimmunity by favoring death effector molecules. Up-regulating the effect of Bcl-2 and favoring death repressor molecules would be beneficial in the treatment and diagnosis of immunodeficiency diseases, including AIDs, and in neurodegenerative and ischemic cell death.

SUMMARY OF THE INVENTION

The present invention relates to the unexpected discovery that Bcl-2 interacts with other proteins and in particular with an associated 21 kD protein called Bax. Bax shares extensive amino acid homology with Bcl-2 focused within highly conserved domains I and II. It has been unexpectedly discovered that Bax homodimerizes and forms heterodimers with Bcl-2 in vivo. It has also been discovered that overexpressed Bax accelerates apoptotic death induced by cytokine deprivation in an IL-3 dependent cell line and that overexpressed Bax also counters the death repressor activity of Bcl-2. This discovery provides a model in which the ratio of Bcl-2/Bax determines cell survival or death following an apoptotic stimulus.

Accordingly, one embodiment of the invention involves the formation of a purified and isolated Bcl-2 associated protein (Bax) and fragments thereof having the amino acid sequence of Domain I or II of FIG. 7.

Another embodiment involves the formation of Bcl-2 and Bax mutants wherein the native protein or fragment has at least one amino acid deleted or replaced by another amino acid and the mutants exhibits altered biological activity from the native protein or fragment.

Another embodiment involves an associated protein, which comprises Bax protein coupled with Bcl-2 associated protein or fragments thereof.

A further embodiment involves DNA isolate consisting essentially of a genomic DNA sequence encoding human Bax and more particularly a composition consisting of c DNA molecules which encode the Bax protein.

In one aspect of the invention, Bax polypeptides and compositions thereof are provided. Bax polypeptides comprise polypeptide sequences which are substantially identical to a sequence shown in FIGS. 3, 5 or 6. In one embodiment, the Bax polypeptide comprises domain I and/or domain II of the Bax polypeptide sequence, and preferably comprises the amino acid sequence(s) -W-G-R- and/or -Q-D-N-, and may be a cyclic polypeptide in some embodiments.

A further aspect involves a composition of αRNA, βRNA and/or γRNA which encode a 21 kD, 24 kD or 4 kD Bax protein as well as cell lines producing such RNA species.

Another aspect of the invention involves Bax pharmaceutical compositions, which contain pharmaceutically effective amounts of a Bax polypeptide and a suitable pharmaceutical carrier.

Polynucleotide sequences encoding Bax are also provided. The characteristics of the cloned sequences are given, including the nucleotide and predicted amino acid sequence in FIGS. 3, 5 and 6. Polynucleotides comprising sequences encoding these amino acid sequences can serve as templates for the recombinant expression of quantities of Bax polypeptides, such as human Bax and murine Bax.

The invention also provides host cells expressing Bax polypeptides encoded by a polynucleotide other than a naturally-occurring Bax gene of the host cell.

In one aspect of the invention, a polynucleotide encoding a Bax polypeptide is delivered to a cell, such as an explanted lymphocyte, hematopoietic stem cell, bone marrow cell, and the like.

An additional aspect of the invention involves a method for controlling cell death repressor activity of Bcl-2, which comprises administering a Bax protein or fragment thereof to a cell containing Bcl-2 activity to enable the formation of a heterodimer containing Bax/Bcl-2, and inhibiting the Bcl-2 cell death repressor activity.

In one aspect of the invention, a method for modulating apoptosis of a cell, typically a lymphocyte, is provided. The method comprises administering to a cell an agent which alters intermolecular binding between Bcl-2 and Bax proteins, typically by inhibiting formation of heteromultimers (e.g., heterodimers) between Bcl-2 and Bax and/or homomultimers of Bcl-2 or Bax.

In one aspect of the invention, the method(s) of modulating apoptosis of a cell by administering an agent which alters intermolecular binding between Bcl-2 and Bax proteins are used to treat a pathological condition in a patient.

As an additional embodiment, the invention involves a method for assaying for the predisposition for an apoptotic cell death, which comprises: collecting a specimen to be tested; contacting the specimen with a material reactive with Bcl-2 or Bax protein; and detecting or determining the presence or absence of Bax and Bcl-2 protein and their ratio in the specimen.

The invention provides screening assays for identifying agents which modulate (e.g., inhibit) binding of a Bax polypeptide to a Bcl-2 polypeptide and/or which modulate (e.g., inhibit) binding of a Bax polypeptide to a Bax polypeptide.

The invention also involves the use of the protein Bax or Bcl-2 or mutant or fragment thereof for performing immunochemical methods for the detection and determination of the protein or its associated protein Bcl-2, in order to monitor cell survival versus death or to detect or monitor the course of diseases.

The invention also provides Bax polynucleotide probes for diagnosis of pathological conditions (e.g., neoplasia, AIDS, hyperplasia, congenital genetic diseases) by detection of Bax mRNA or rearrangements deletions or amplification of the Bax gene in cells explanted from a patient, or detection of a pathognomonic Bax allele (e.g., by RFLP or allele-specific PCR analysis).

In one aspect of the invention, transgenic nonhuman animals, such as mice, bearing a transgene encoding a Bax polypeptide and/or a Bcl-2 polypeptide are provided. Such transgenes may be homlogously recombined into the host chromosome or may be non-homlogously integrated.

Further included is a method for the treatment of a neurodegenerative disease, an immunodeficiency, or an ischemia, which comprises; increasing the effective amount of Bcl-2 or decreasing Bax or administering a mutant or fragment thereof to a patient to regulate the ratio of Bcl-2 to Bax to promote the survival of cells by generating an excess of Bcl-2; and, a method for the treatment of hyperplasias, hypertrophies, cancers and autoimmunity disorders, which comprises: decreasing the effective amount of Bcl-2 or increasing Bax or administering a mutant thereof to a patient to regulate the ratio of Bcl-2 to Bax so as to favor Bax and promote cell death.

In one aspect of the invention, an antisense polynucleotide is administered to inhibit transcription and/or translation of Bax in a cell.

The invention provides antibodies, both monoclonal antibodies and polyclonal antisera, which specifically bind to a Bax polypeptide with an affinity of about at least $1\times10^7$ $M^{-1}$, typically at least $1\times10^8$ $M^{-1}$ or more.

BRIEF DESCRIPTION OF THE DRAWINGS

FIG. 3 demonstrates the human cDNA (SEQ ID NO:1) and protein sequence of human (SEQ ID NO:2) and murine (SEQ ID NO:3) Bax.

FIG. 5 demonstrates the DNA (SEQ ID NO:6) and the amino acids (SEQ ID NO.:5) encoded from intron 5 of βRNA.

FIG. 6 demonstrates the DNA (SEQ ID NO:6) and the amino acids (SEQ ID NO:7) encoded from γRNA.

FIG. 14 shows a family of Bcl-2 closely related genes and the Bcl-2 mutants generated. (SEQ. ID NOS: 12 to 31).

DESCRIPTION OF THE PREFERRED EMBODIMENTS

Figure 1:
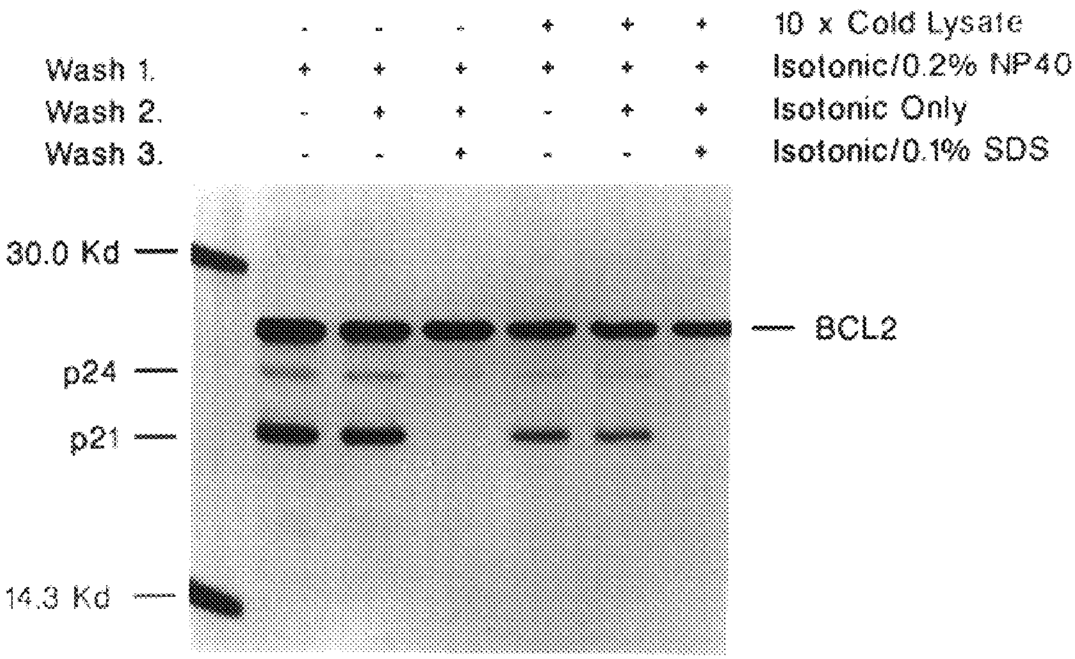
FIG. 1 shows the analysis of ($^{35}$S) Methionine-labeled immunoprecipitates using RL-7 cells.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

As used herein, the twenty conventional amino acids and their abbreviations follow conventional usage (*Immunology—A Synthesis*, 2nd Edition, E. S. Golub and D. R. Gren, Eds., Sinauer Associates, Sunderland, Mass. (1991), which is incorporated herein by reference). Stereoisomers (e.g., D-amino acids) of the twenty conventional amino acids, unnatural amino acids such as αα-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention. Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

As used herein, the term "Bax" refers to the mammalian Bax gene and mammalian Bax proteins, including the α, β, and γ isoforms, unless otherwise identified; human and murine Bax proteins and genes are preferred exemplifications of mammalian Bax, and in its narrowest usage Bax refers to human Bax polynucleotide and polypeptide sequences.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, such as a polynucleotide sequence of FIG. 3 or FIGS. 5 and 6, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci. (U.S.A.)* 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length human Bax polynucleotide sequence shown in FIG. 3 or FIGS. 5 and 6.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Figure 4:
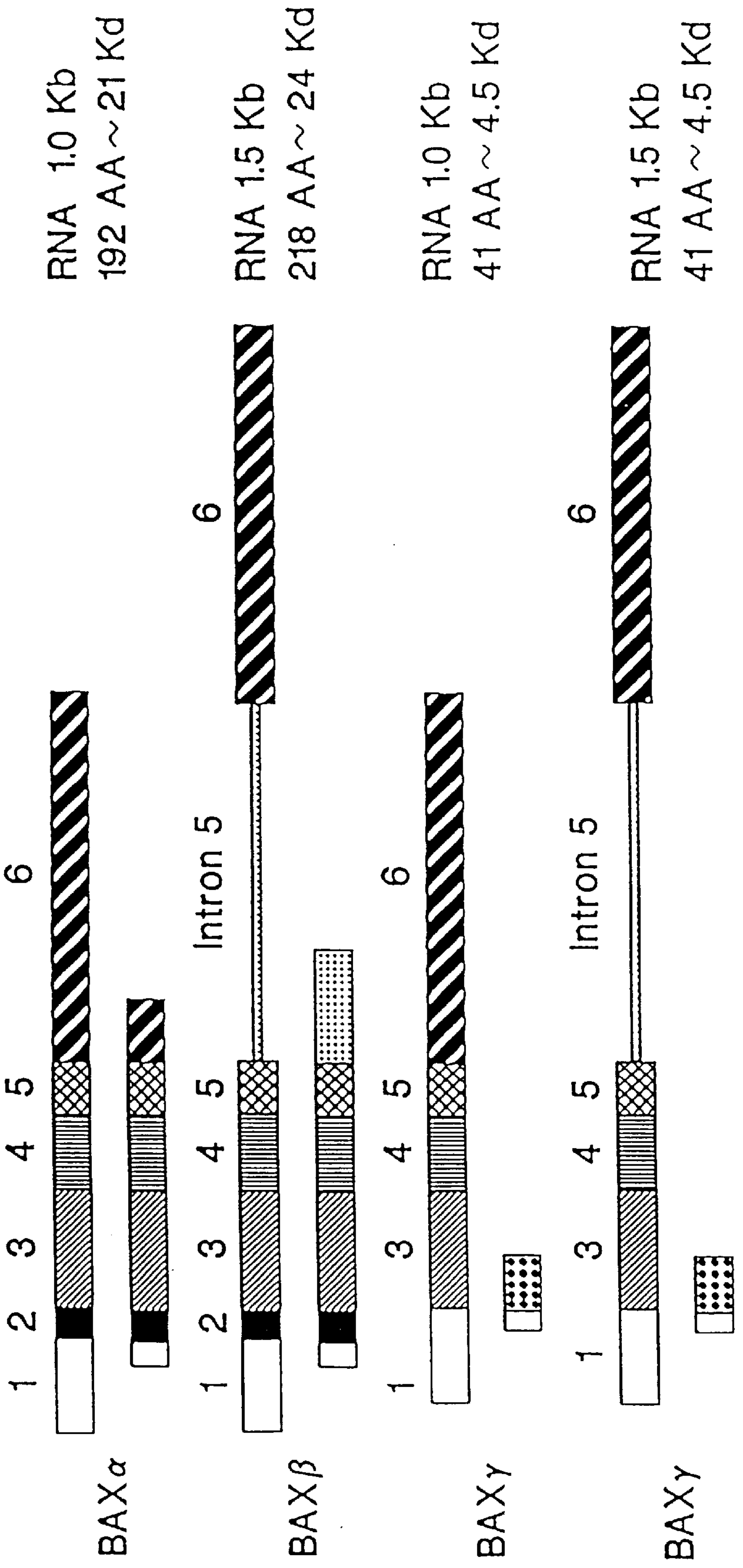
FIG. 4 demonstrates alternative α, β, γ transcripts and proteins of the Bax gene.

The term "Bax native protein" and "full-length Bax protein" as used herein refers to a full-length Bax α, β, γ or isoform of 192 amino acids (SEQ ID NOS:2, 3, 8 or 9), 218 amino acids (SEQ ID NO:32), or 41 amino acids (SEQ ID NO:7), respectively, as shown herein (see, FIG. 4). A preferred Bax native protein is the polypeptide corresponding to the deduced amino acid sequence shown in FIG. 3 or corresponding to the deduced amino acid sequence of a cognate full-length cDNA of another species. Also for example, a native Bax protein present in naturally-occurring lymphocytes which express the Bas gene a re considered full-length Bax proteins.

The term "fragment" as used herein refers to a polypeptide that has an amino-terminal and/or carboxy-terminal deletion, but where the remaining amino acid sequence is identical to the corresponding positions in the sequence deduced from a full-length cDNA sequence (e.g., the cDNA sequence shown in FIG. 3). Fragments typically are at least 14 amino acids long, preferably at least 20 amino acids long, usually at least 50 amino acids long or longer.

The term "analog", "mutein" or "mutant" as used herein refers to polypeptides which are comprised of a segment of at least 10 amino acids that has substantial identity to a portion of the naturally occurring protein. For example, a Bax analog comprises a segment of at least 10 amino acids that has substantial identity to a Bax protein, such as the human α, β, or γ isoforms; preferably the deduced amino acid sequence shown in FIG. 3 or deduced amino acid sequences shown in FIGS. 5 and 6, and which has at least one of the following properties: binding to Bcl-2 or native Bax protein under suitable binding conditions. Typically, analog polypeptides comprise a conservative amino acid substitution (or addition or deletion) with respect to the naturally-occurring sequence. Analogs typically are at least 20 amino acids long, preferably at least 50 amino acids long or longer, most usually being as long as full-length naturally-occurring protein (e.g., 192, 218, or 41 amino acid residues for human Bax α, β, and γ, respectively). Some analogs may lack biological activity (e.g., Bcl-2 binding) but may still be employed for various uses, such as for raising antibodies to Bax epitopes, as an immunological reagent to detect and/or purify α-Bax antibodies by affinity chromatography, or as a competitive or noncompetitive agonist, antagonist, or partial agonist of native Bax protein function.

The term "Bax polypeptide" is used herein as a generic term to refer to native protein, fragments, or analogs of Bax. Hence, native Bax, fragments of Bax, and analogs of Bax are species of the Bax polypeptide genus. Preferred Bax polypeptides include: a murine full-length Bax protein comprising the murine polypeptide sequence shown in FIG. 3, a full-length human Bax protein comprising the polypeptide sequence shown in FIG. 3, polypeptides consisting essentially of the sequence of human Bax domain I or domain II, and the naturally-occurring human Bax α, β (SEQ ID NO:32), or y isoforms.

The term "Bcl-2 polypeptide" is used herein as a generic term to refer to native protein, fragments, or analogs of Bcl-2, preferably human or murine Bcl-2, usually human Bcl-2.

The term "cognate" as used herein refers to a gene sequence that is evolutionarily and functionally related between species. For example but not limitation, in the human genome, the human CD4 gene is the cognate gene to the mouse CD4 gene, since the sequences and structures of these two genes indicate that they are highly homologous and both genes encode a protein which functions in signaling T cell activation through MHC class II-restricted antigen recognition. Thus, the cognate human gene to the murine Bax gene is the human gene which encodes an expressed protein which has the greatest degree of sequence identity to the murine Bax protein and which exhibits an expression pattern similar to that of the murine Bax (e.g., expressed in lymphocytes). Preferred cognate Bax genes are: rat Bax, rabbit Bax, canine Bax, nonhuman primate Bax, porcine Bax, bovine Bax, and hamster Bax.

The term "agent" is used herein to denote a chemical compound, a mixture of chemical compounds, a biological macromolecule, or an extract made from biological materials such as bacteria, plants, fungi, or animal (particularly mammalian) cells or tissues. Agents are evaluated for potential activity as antineoplastics or apoptosis modulators by inclusion in screening assays described hereinbelow.

The term "antineoplastic agent" is used herein to refer to agents that have the functional property of inhibiting a development or progression of a neoplasm in a human, particularly a lymphocytic leukemia, lymphoma or preleukemic condition.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). Various methods of labeling polypeptides and glycoproteins are known in the art and may be used. Examples of labels for polypeptides include, but are not limited to, the following: radioisotopes (e.g., $^{3}H$, $^{14}C$, $^{35}S$, $^{125}I$, $^{131}I$), fluorescent labels (e.g., FITC, rhodamine, lanthanide phosphors), enzymatic labels (e.g., horseradish peroxidase, β-galactosidase, luciferase, alkaline phosphatase), biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

As used herein "normal blood" or "normal human blood" refers to blood from a healthy human individual who does not have an active neoplastic disease or other disorder of lymphocytic proliferation, or an identified predisposition for developing a neoplastic disease. Similarly, "normal cells", "normal cellular sample", "normal tissue", and "normal lymph node" refers to the respective sample obtained from a healthy human individual who does not have an active neoplastic disease or other lymphoproliferative disorder.

As used herein the terms "pathognomonic concentration", "pathognomonic amount", and "pathognomonic staining pattern" refer to a concentration, amount, or localization pattern, respectively, of a Bax protein or mRNA in a sample, that indicates the presence of a pathological (e.g., neoplastic) condition or a predisposition to developing a neoplastic disease, such as lymphocytic leukemia. A pathognomonic amount is an amount of a Bax protein or Bax mRNA in a cell or cellular sample that falls outside the range of normal clinical values that is established by prospective and/or retrospective statistical clinical studies. Generally, an individual having a neoplastic disease (e.g., lymphocytic leukemia) will exhibit an amount of Bax protein or mRNA in a cell or tissue sample that is outside the range of concentrations that characterize normal, undiseased individuals; typically the pathognomonic concentration is at least about one standard deviation outside the mean normal value, more usually it is at least about two standard deviations or more above the mean normal value. However, essentially all clinical diagnostic tests produce some percentage of false positives and false negatives. The sensitivity and selectivity of the diagnostic assay must be sufficient to satisfy the diagnostic objective and any relevant regulatory requirements. In general, the diagnostic methods of the invention are used to identify individuals as disease candidates, providing an additional parameter in a differential diagnosis of disease made by a competent health professional.

Oligonucleotides can be synthesized on an Applied Bio Systems oligonucleotide synthesizer according to specifications provided by the manufacturer.

Methods for PCR amplification are described in the art (*PCR Technology: Principles and Applications for DNA Amplification* ed. H A Erlich, Freeman Press, New York, N.Y. (1992); *PCR Protocols: A Guide to Methods and Applications*, eds. Innis, Gelfland, Snisky, and White, Academic Press, San Diego, Calif. (1990); Mattila et al. (1991) *Nucleic Acids Res.* 19: 4967; Eckert, K. A. and Kunkel, T. A. (1991) *PCR Methods and Applications* 1: 17; *PCR*, eds. McPherson, Quirkes, and Taylor, IRL Press, Oxford; and U.S. Pat. No. 4,683,202, which are incorporated herein by reference).

It is known that the development as well as the maintenance of many adult tissues is achieved by several dynamically regulated processes that include cell proliferation, differentiation and programmed cell death. In the latter process, cells are eliminated by a highly characteristic suicide program entitled apoptosis.

Bcl-2 was first isolated at the chromosomal breakpoint of t(14;18) bearing follicular B cell lymphomas. Transgenic mice bearing a Bcl-2-Ig mini-gene that recapitulates this translocation display a polyclonal follicular hyperplasia with a four-fold increase in resting B cells and as such B cells accumulate because of extended cell survival rather than increased proliferation.

A survey of adult tissues indicates that Bcl-2 has played several roles in numerous cell lineages. Glandular epithelium that undergoes hyperplasia or involution in response to hormonal stimuli or growth factors express Bcl-2. In complex epithelium, such as the skin and gut, Bcl-2 is restricted to stem cells and proliferation zones. Within the adult nervous system Bcl-2 is more prominent in the peripheral nervous system rather than the central nervous system. Thus Bcl-2 may be needed to save the progenitor and long-lived cells in a variety of cell lineages.

Despite the progress in defining Bcl-2's physiologic roles, the biochemical basis of its action has remained ambiguous up until the present invention. Dual fluorescence staining of cells, examined with a laser scanning confocal microscope, indicates that Bcl-2 protein within a B cell line was coincident with the distribution of mitochondria. Subcellular fractionation studies revealed that the majority of Bcl-2 was localized as an integral mitochondrial membrane protein which suggests that Bcl-2 might alter some mitochondrial function associated with energy production. However, Bcl-2 was able to prevent cell death in a fibroblast line that lacks mitochondrial DNA.

Bcl-2 appears to function in several subcellular locations, yet lacks any known motifs that would confer a biochemical role. It has been unexpectedly discovered that Bcl-2 associates, in vivo with a 21 kD protein partner, herein called Bax. Bax shows extensive amino acid homology with Bcl-2 and forms homodimers with itself and heterodimers-with Bcl-2 in vivo. Bax is encoded by 6 exons and demonstrates a complex pattern of alternative RNA splicing that predicts a 21 Kd membrane (α) and two forms (β and γ) of cytosolic protein. When Bax predominates, programmed cell death is accelerated and the death repressor activity of Bcl-2 is countered.

According to the present invention a co-immunoprecipitation procedure was used to identify Bax, the novel protein associated with Bcl-2. It was completely unexpected to find that Bax shared extensive homology with Bcl-2, especially within two highly conserved domains. These domains are also the most highly conserved regions of human, mouse and chicken Bcl-2. These domains are also conserved in an open reading frame BHRF-1 within Epstein-Barr virus and Mcl-1, a gene recently isolated from a myeloid leukemia cell line following induction with phorbol ester (Kozopas et al., 1993). Thus, a clear family of Bcl-2-like genes is appearing and are likely to be sequential numbers of a single death pathway or regulators of parallel death pathways.

As discussed above, Bax homodimerizes or heterodimerizes with Bcl-2 in vivo. While the precise multiplicity of these interactions is not fully known, conserved domains I and II are areas of dimerization motifs. Baxα possesses a COOH-terminal hydrophobic segment predicted to be membrane spanning and has a similar secondary structure to Bcl-2. Thus, the two proteins are likely to be inserted into the same membrane with an identical orientation. However, coinsertion is not required for association in that the ΔC-22 cytosolic form of Bcl-2 still coprecipitates Baxα, provided it has been solubilized from membranes. Since Bcl-2 ΔC-22 partially protects cells from death, this further strengthens the importance of the Bcl-2/Bax interaction. Moreover, results using FL5.12 cells indicate that Bax homodimerization is favored over heterodimerization with Bcl-2. It has been found that the majority of introduced HA-Baxα dimerizes with endogenous Baxα rather than with the modest amounts of endogenous Bcl-2 in FL5.12 cells. Overexpression of Bcl-2 in these cells thus competes for Bax homodimerization and forms heterodimers with HA-Baxα and endogenous Baxα.

The complexity of the RNA splicing therein proves to be an important differential regulator of Bax activity and localization. The predicted membrane α and cytosolic β forms of Bax are parallel to the α integral membrane form of Bcl-2 and predicted β cytosolic form. The exon/intron juncture responsible for the α and β RNAs are evolutionarily conserved and thus the existence of 24 kD Baxβ protein is believed to be proven. Consistent with this, RL-7 cells display a 24 kD protein associated with Bcl-2 and possess the 1.5 kb βRNA, while FL5.12 cells lack both. A cytosolic Baxβ could provide an additional level of regulation by homodimerizing or heterodimerizing with the integral membrane forms of Bax and Bcl-2. The γ form of Bax RNA might result in a truncated γ protein or could represent a splicing strategy to avoid making the full length product.

It has been discovered that the ratio of Bcl-2/Bax determines a cells susceptibility to death following an apoptotic stimulus. In the presence of IL-3 overexpressed Bax does not noticeably alter normal cell division or viability. Bax is present and associated with Bcl-2 prior to growth factor deprivation. Moreover, the ratio of Bcl-2/Bax within FL5.12 cells is not substantially altered 12 hrs after deprivation of IL-3. Bax RNA is expressed in normal tissues and in a variety of cell lines prior to a death induction signal. Thus, the synthesis of Bax does not appear to be a de novo response that follows a death stimulus, and Bax in itself accelerates apoptotic cell death only following a death signal, such as IL-3 deprivation. Excess Bax also counters the death repressor activity of Bcl-2. When Bcl-2 is in excess cells are protected. However, when Bax is in excess and Bax homodimers dominate, cells are susceptible to apoptosis.

It has also been discovered that a single amino acid substitution in Bcl-2 eliminates Bcl-2/Bax heterodimers but not Bcl-2 homodimers and abolishes death repressor activity. As discussed herein, the Bcl-2 proto-oncogene inhibits apoptosis induced by a variety of signals within multiple cell types. Protein mutations with as minor as a single amino acid substitution within one conserved region, domain I, of the Bcl-2 molecule also eliminates its death repressor activity. Mutated Bcl-2 no longer blocks cell death induced by factor deprivation, glucocorticoid treatment or gamma irradiation. Bcl-2 mutations that no longer function, no longer heterodimerize with Bax, and when overexpressed accelerate programmed cell death. Mutations within domain II of Bcl-2 partially disrupt its death repressor activity and correspondingly partially inhibit its heterodimerization with Bax. However, mutant Bcl-2 as well as wild-type Bcl-2 still effectively forms homodimers. These results document the importance of the conserved sequences especially domain I and their role in heterodimerization for Bcl-2 and Bax. Such domains are also likely to be instrumental in dictating homo and heterodimerization formation in other Bcl-2 family members including Bcl-x, MCL-1, LMW5-HL and BHRF1.

The current data support a model in which Bcl-2 functions by neutralizing a death accelerating protein Bax through heterodimerization. Therapeutic modalities which disrupt Bcl-2/Bax heterodimers prove profoundly effective in promoting cell death.

Several mechanistic possibilities are believed to account for the regulatory role of this protein-protein interaction. Bax might function as a death effector molecule that is neutralized by Bcl-2. In this scenario, Bcl-2 might simply be an inert handcuff that disrupts the formation of Bax homodimers. Alternatively, Bcl-2 could possess a biochemical function that is diametrically opposed to Bax. In contrast Bcl-2 might function as a death repressor molecule that is neutralized by competition with an inert Bax molecule. Either way, the capacity of Bax and Bcl-2 to compete for one another via heterodimers indicates a reciprocal relationship in which Bcl-2 monomers or homodimers favor survival, and Bax homodimers favor death.

Mammalian cells are often dependent upon an extracellular milieu including growth and survival factors or cell-cell contact molecules. The dependence of the early hematopoietic cell line, FL5.12, upon IL-3 for its survival as well as proliferation is a typical example. However, a number of biologic systems indicate that cells within the same lineage have an inherent sensitivity or resistance to a given death stimulus. For example, $CD4^+8^+$ cortical thymocytes are sensitive to glucocorticoid induced apoptosis while the more mature medullary thymocytes are resistant. This differential sensitivity correlates with the presence of Bcl-2 protein. The Bcl-2/Bax interaction represents one such endogenous regulator of susceptibility to apoptosis. These discoveries suggest a model in which the response of a cell to a death signal is determined by a preset mechanism, such as the ratio of Bcl-2/Bax.

Because of this interaction it is possible to use this invention for the detection and determination of Bax or Bcl-2, for example in a fraction from a tissue or organ separation operation, or immunochemical technique in view of the proteins antigenic properties. Specific antibodies can also be formed on immunization of animals with this protein. It is known that monoclonal antibodies already exist to Bcl-2.

An antiserum which can be utilized for this purpose can be obtained by conventional procedures. One exemplary procedure involves the immunization of a mammal, such as rabbits, which induces the formation of polyclonal antibodies against Bax. Monoclonal antibodies are also being generated from already immunized hamsters. This antibody can be used to detect the presence and level of the Bax protein.

It is also possible to use the proteins for the immunological detection of Bax, Bcl-2 and associations thereof with standard assays as well as assays using markers, which are radioimmunoassays or enzyme immunoassays.

The detection and determination of Bax and/or Bcl-2 has significant diagnostic importance. For example, the detection of proteins favoring death effector molecules would be advantageous in cancer therapy and controlling hypertrophies and eliminating self reactive clones in autoimmunity. The detection or determination of proteins favoring death repressor molecules will be beneficial in immunodeficiency disease, including HIV-I, II and III, and in neurodegenerative and ischemic cell death. Thus these proteins and their antibodies can be employed as a marker to monitor, check or detect the course of disease.

More particularly, the protein Bax may be used for performing immunochemical methods for the detection and determination of the protein or its associated protein Bcl-2, in order to monitor cell growth or to detect or monitor the course of diseases. It can also be used as a method for the treatment of a neurodegenerative disease, or immunodeficiency, or an ischemia induced injury such as myocardial infarction and neurologic stroke, which comprises; administering an effective amount of a compound to a patient to regulate the ratio of Bcl-2 to Bax to promote the survival of cells by generating an excess of Bcl-2.

A method for the treatment of hyperplasias, hypertrophies, cancers and autoimmunity disorders, which comprises: administering an effective amount of a compound to a patient to regulate the ratio of Bcl-2 to Bax so as to favor the Bax protein and promote cell death.

Specific preparations of the Bax proteins and compounds can also be prepared for administration in pharmaceutical preparations. These may be accomplished in a variety of ways well known to those skilled in the art of pharmacy.

It will be understood that the precise chemical structure of Bax and Bcl-2 will depend upon a number of factors. For example, since ionizable amino and carboxyl groups are present in the molecule, a particular protein may be obtained as an acidic or basic salt, or in neutral form. All forms of Bax which retain their therapeutic activity for purposes of the instant invention are intended to be within the scope of the definition of Bax.

The term "recombinant" used herein refers to Bax and Bcl-2 produced by recombinant DNA techniques wherein the gene coding for protein is cloned by known recombinant DNA technology. For example, the human gene for Bax may be inserted into a suitable DNA vector, such as a bacterial plasmid, and the plasmid used to transform a suitable host. The gene is then expressed in the host to produce the recombinant protein. The transformed host may be prokaryotic or eukaryotic, including mammalian, yeast, Aspergillus and insect cells. One preferred embodiment employs bacterial cells as the host.

Therapeutically useful derivatives of Bax may be prepared by augmenting the primary amino acid sequence of the protein with at least one additional molecule selected from the group consisting of glucose moieties, lipids, phosphate groups, acetyl groups, hydroxyl groups, saccharides, methyl groups, propyl groups, amino acids, and polymeric molecules. Augmentation may be accomplished through post-translational processing systems of the producing host, or it may be carried out in vitro. Both techniques are well-known in the art.

Referring to the Sequence Description of Bax, it should be noted that the peptide includes several potential glycosylation sites. Glycosylation is a process of forming a protein derivative, wherein a portion of the protein's amino acid sequence is augmented by a sugar moiety. It will therefore be understood that therapeutically useful derivatives of Bax may be prepared by addition of one or more sugar residues to the protein, or alternatively by removal of some or all of the sugar residues from the sites of glycosylation on the Bax molecule.

Other therapeutically useful derivatives of Bax may be formed by modifying at least one amino acid residue of Bax or Bcl-2 by oxidation, reduction, or other derivatization processes known in the art.

Mutants of Bax and Bcl-2 which modify the activity of the protein may be used as the active treating substance of the instant invention. Muteins are prepared by modification of the primary structure of the protein itself, by deletion, addition, or alteration of the amino acids incorporated into the sequence during translation. For example, at least one glycine residue of Bax or Bcl-2 in Domain I may be replaced with an amino acid such as alanine or glutamic acid. Also, it may be desirable to eliminate or replace a group of amino aids, such as the FRDG or WGR sequence in Bcl-2 domain I to remove bioactivity of the protein.

Bax and Bcl-2 are believed to exist in nature as a dimer of two identical, non-covalently linked protein subunits. Accordingly, since each subunit is believed to have the amino acid sequence shown in SEQ ID NO:1 and 2, a subunit of Bax or Bcl-2 could be used as the therapeutically active or diagnostic substance according to the instant invention. The invention also encompasses use of subunits of protein that are covalently or non-covalently linked, either naturally or by artificial techniques known in the art.

In addition, it is contemplated that fragments of Bax and Bcl-2 would be useful in the invention, provided that such fragments retained their therapeutic activity.

Figure 7:
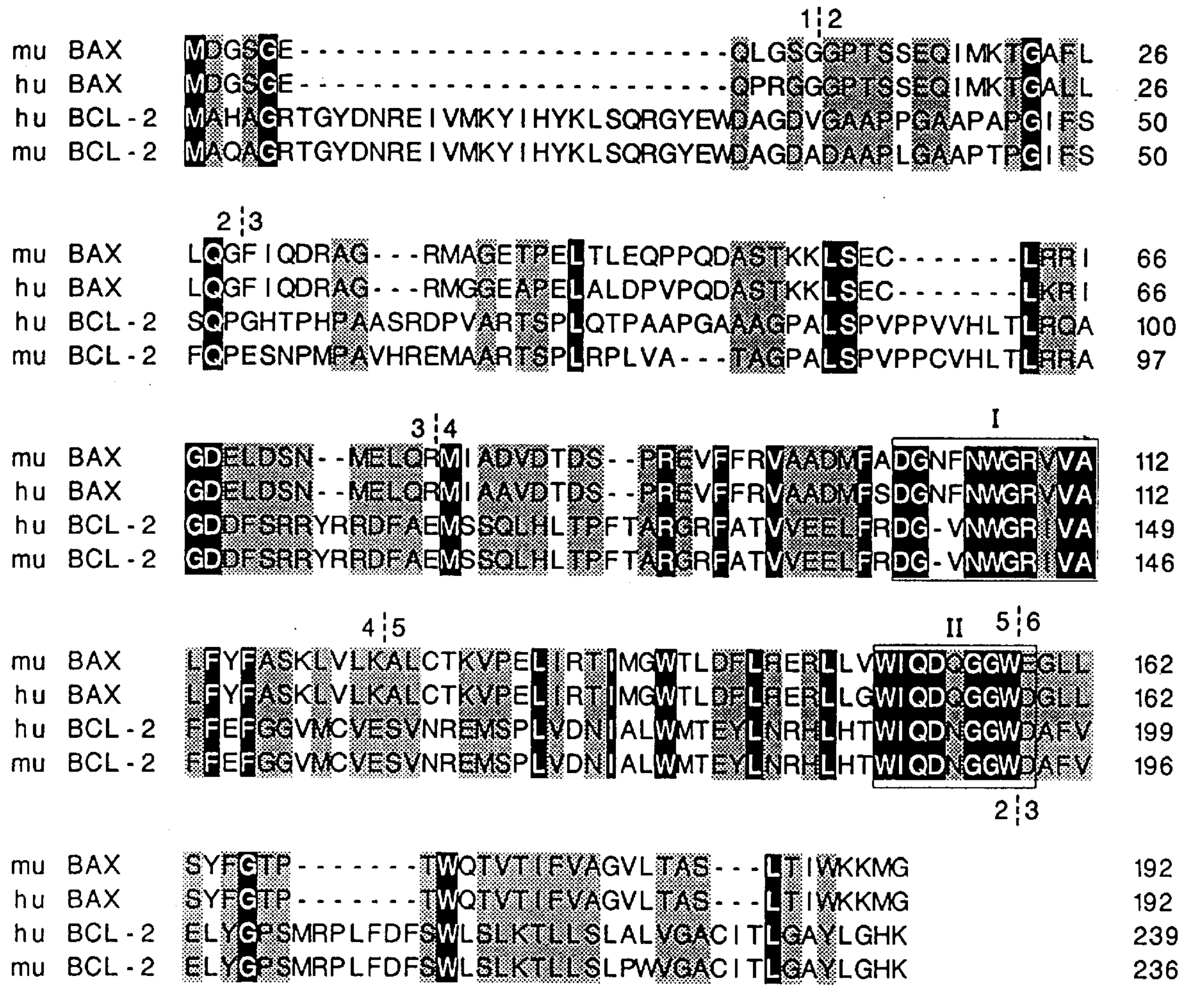
FIG. 7 shows the alignment of the murin Bax (SEQ ID NO:8) and human Bax (SEQ ID NO:9) and human (SEQ ID NO:1) and murine (SEQ ID NO:11) Bcl-1 proteins.

The fragment defined by amino acid residues in domain I and domain II of FIG. 7 are believed to be therapeutically active for purposes of the invention. The fragment defined by these residues is believed to be therapeutically active because: it is a linear sequence not involving disulfide bridges and because it appears to be key to repressing cell death.

The above-described forms of Bax and Bcl-2 are used in an effective therapeutic amount, which will vary depending on the level of Bax and Bcl-2 already present in the patient, the site and method of administration, the form of protein utilized, and other factors understood to those having ordinary skill in the art.

Cloning of Bax Polynucleotides

Genomic or cDNA clones encoding Bax may be isolated from clone libraries (e.g., available from Clontech, Palo Alto, Calif.) using hybridization probes designed on the basis of the nucleotide sequences shown in FIG. 3 and FIGS. 5 and 6 and using conventional hybridization screening methods (e.g., Benton W D and Davis R W (1977) *Science* 196: 180; Goodspeed et al. (1989) *Gene* 76: 1). Where a cDNA clone is desired, clone libraries containing cDNA derived from lymphocyte mRNA or other Bax-expressing cell mRNA are preferred. Alternatively, synthetic polynucleotide sequences corresponding to all or part of the sequences shown in FIG. 3 and FIGS. 5 and 6 may be constructed by chemical synthesis of oligonucleotides. Additionally, polymerase chain reaction (PCR) using primers based on the sequence data disclosed in FIG. 3 and FIGS. 5 and 6 may be used to amplify DNA fragments from genomic DNA, mRNA pools, or from cDNA clone libraries. U.S. Pat. Nos. 4,683,195 and 4,683,202 describe the PCR method. Additionally, PCR methods employing one primer that is based on the sequence data disclosed in FIG. 3 and a second primer that is not based on that sequence data may be used. For example, a second primer that is homologous to or complementary to a polyadenylation segment may be used.

It is apparent to one of skill in the art that nucleotide substitutions, deletions, and additions may be incorporated into the polynucleotides of the invention. Nucleotide sequence variation may result from sequence polymorphisms of various Bax alleles, minor sequencing errors, and the like. However, such nucleotide substitutions, deletions, and additions should not substantially disrupt the ability of the polynucleotide to hybridize to one of the polynucleotide sequences shown in FIG. 3 or FIGS. 5 and 6 under hybridization conditions that are sufficiently stringent to result in specific hybridization.

Specific hybridization is defined herein as the formation of hybrids between a probe polynucleotide (e.g., a polynucleotide of the invention which may include substitutions, deletion, and/or additions) and a specific target polynucleotide (e.g., a polynucleotide having the sequence in FIG. 3 or FIGS. 5 and 6), wherein the probe preferentially hybridizes to the specific target such that, for example, a single band corresponding to one or more of the isoforms of Bax ($\alpha$, $\beta$, or $\gamma$) alternatively spliced mRNA species can be identified on a Northern blot of RNA prepared from a suitable cell source (e.g., a T or B cell expressing Bax). Polynucleotides of the invention and recombinantly produced Bax, and fragments or analogs thereof, may be prepared on the basis of the sequence data provided in FIG. 3 and FIGS. 5 and 6 according to methods known in the art and described in Maniatis et al., *Molecular Cloning: A Laboratory Manual*, 2nd Ed., (1989), Cold Spring Harbor, N.Y. and Berger and Kimmel, *Methods in Enzymology, Volume* 152, *Guide to Molecular Cloning Techniques* (1987), Academic Press, Inc., San Diego, Calif., which are incorporated herein by reference.

Bax polynucleotides may be short oligonucleotides (e.g., 25–100 bases long), such as for use as hybridization probes and PCR (or LCR) primers. Bax polynucleotide sequences may also comprise part of a larger polynucleotide (e.g., a cloning vector comprising a Bax clone) and may be fused, by polynucleotide linkage, in frame with another polynucleotide sequence encoding a different protein (e.g., glutathione S-transferase or $\beta$-galactosidase) for encoding expression of a fusion protein. Typically, Bax polynucleotides comprise at least 25 consecutive nucleotides which are substantially identical to a naturally-occurring Bax sequence (e.g., FIG. 3), more usually Bax polynucleotides comprise at least 50 to 100 consecutive nucleotides which are substantially identical to a naturally-occurring Bax sequence. However, it will be recognized by those of skill that the minimum length of a Bax polynucleotide required for specific hybridization to a Bax target sequence will depend on several factors: G/C content, positioning of mismatched bases (if any), degree of uniqueness of the sequence as compared to the population of target polynucleotides, and chemical nature of the polynucleotide (e.g., methylphosphonate backbone, phosphorothiolate, etc.), among others.

If desired, PCR amplimers for amplifying substantially full-length cDNA copies may be selected at the discretion of the practioner. Similarly, amplimers to amplify single Bax exons or portions of the Bax gene (murine or human) may be selected.

Each of these sequences may be used as hybridization probes or PCR amplimers to detect the presence of Bax mRNA, for example to diagnose a lymphoproliferative disease characterized by the presence of an elevated or reduced Bax mRNA level in lymphocytes, or to perform tissue typing (i.e., identify tissues characterized by the expression of Bax mRNA), and the like. The sequences may also be used for detecting genomic Bax gene sequences in a DNA sample, such as for forensic DNA analysis (e.g., by RFLP analysis, PCR product length(s) distribution, etc.) or for diagnosis of diseases characterized by amplification and/or rearrangements of the Bax gene.

Production of Bax Polypeptides

The nucleotide and amino acid sequences shown in FIG. 3 and FIG. 5 and 6 enable those of skill in the art to produce polypeptides corresponding to all or part of the full-length human and murine Bax polypeptide sequences. Such polypeptides may be produced in prokaryotic or eukaryotic host cells by expression of polynucleotides encoding Bax, or fragments and analogs thereof. Alternatively, such polypeptides may be synthesized by chemical methods or produced by in vitro translation systems using a polynucleotide template to direct translation. Methods for expression of heterologous proteins in recombinant hosts, chemical synthesis of polypeptides, and in vitro translation are well known in the art and are described further in Maniatis et al., *Molecular Cloning: A Laboratory Manual* (1989), 2nd Ed., Cold Spring Harbor, N.Y. and Berger and Kimmel, *Methods in Enzymology, Volume* 152, *Guide to Molecular Cloning Techniques* (1987), Academic Press, Inc., San Diego, Calif.

Fragments or analogs of Bax may be prepared by those of skill in the art. Preferred amino- and carboxy-termini of fragments or analogs of Bax occur near boundaries of functional domains. For example, but not for limitation, such functional domains include domains conferring the property of binding to a Bcl-2 polypeptide, and (2) domains conferring the property of binding to a Bax polypeptide.

One method by which structural and functional domains may be identified is by comparison of the nucleotide and/or amino acid sequence data shown in FIG. 3 or FIGS. 5 and 6 to public or proprietary sequence databases. Preferably, computerized comparison methods are used to identify sequence motifs or predicted protein conformation domains that occur in other proteins of known structure and/or function, such as domain I and domain II. For example, the NAD-binding domains of dehydrogenases, particularly lactate dehydrogenase and malate dehydrogenase, are similar in conformation and have amino acid sequences that are detectably homologous (*Proteins. Structures and Molecular Principles*, (1984) Creighton (ed.), W.H. Freeman and Company, New York, which is incorporated herein by reference). Further, a method to identify protein sequences that fold into a known three-dimensional structure are known (Bowie et al. (1991) *Science* 253: 164). Thus, the foregoing examples demonstrate that those of skill in the art can recognize sequence motifs and structural conformations that may be used to define structural and functional domains in the Bax sequences of the invention.

Additionally, computerized comparison of sequences shown in FIG. 3 or FIGS. 5 and 6 to existing sequence databases can identify sequence motifs and structural conformations found in other proteins or coding sequences that indicate similar domains of the Bax protein. For example but not for limitation, the programs GAP, BESTFIT, FASTA, and TFASTA in the Wisconsin. Genetics Software Package (Genetics Computer Group, 575 Science Dr., Madison, Wis.) can be used to identify sequences in databases, such as GenBank/EMBL, that have regions of homology with a Bax sequences. Such homologous regions are candidate structural or functional domains. Alternatively, other algorithms are provided for identifying such domains from sequence data. Further, neural network methods, whether implemented in hardware or software, may be used to: (1) identify related protein sequences and nucleotide sequences, and (2) define structural or functional domains in Bax polypeptides (Brunak et al. (1991) *J. Mol. Biol.* 220: 49, which is incorporated herein by reference).

Fragments or analogs comprising substantially one or more functional domain may be fused to heterologous polypeptide sequences, wherein the resultant fusion protein exhibits the functional property(ies) conferred by the Bax fragment. Alternatively, Bax polypeptides wherein one or more functional domain have been deleted will exhibit a loss of the property normally conferred by the missing fragment.

By way of example and not limitation, the domain(s) conferring the property of binding to Bcl-2 may be fused to β-galactosidase to produce a fusion protein that can bind an immobilized Bcl-2 polypeptide in a binding reaction and which can enzymatically convert a chromogenic substrate to a chromophore.

Although one class of preferred embodiments are fragments having amino- and/or carboxy-termini corresponding to amino acid positions near functional domains borders, alternative Bax fragments may be prepared. The choice of the amino- and carboxy-termini of such fragments rests with the discretion of the practitioner and will be made based on experimental considerations such as ease of construction, stability to proteolysis, thermal stability, immunological reactivity, amino- or carboxyl-terminal residue modification, or other considerations.

In addition to fragments, analogs of Bax can be made. Such analogs may include one or more deletions or additions of amino acid sequence, either at the amino- or carboxy-termini, or internally, or both; analogs may further include sequence transpositions. Analogs may also comprise amino acid substitutions, preferably conservative substitutions. Additionally, analogs may include heterologous sequences generally linked at the amino- or carboxy-terminus, wherein the heterologous sequence(s) confer a functional property to the resultant analog which is not indigenous to the native Bax protein. However, Bax analogs must comprise a segment of 25 amino acids that has substantial similarity to a portion of the amino acid sequences shown in FIG. 3 or FIGS. 5 and 6 or other mammalian Bax proteins, respectively, and which has at least one of the requisite functional properties (i.e., forms heterodimers with Bcl-2 and/or forms homodimers with Bax. Preferred amino acid substitutions are those which: (1) reduce susceptibility to proteolysis, (2) reduce susceptibility to oxidation, (3) alter post-translational modification of the analog, possibly including phosphorylation, and (4) confer or modify other physicochemical or functional properties of such analogs. Bax analogs include various muteins of a Bax sequence other than the naturally-occurring peptide sequence. For example, single or multiple amino acid substitutions (preferably conservative amino acid substitutions) may be made in the naturally-occurring Bax sequence (preferably in the portion of the polypeptide outside domains I and II).

Conservative amino acid substitution is a substitution of an amino acid by a replacement amino acid which has similar characteristics (e.g., those with acidic properties: Asp and Glu). A conservative (or synonymous) amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles*, (1984) Creighton (ed.), W.H. Freeman and Company, New York; *Introduction to Protein Structure*, (1991), C. Branden and J. Tooze, Garland Publishing, New York, N.Y.; and Thornton et al. (1991) *Nature* 354: 105; which are incorporated herein by reference).

Similarly, full-length Bcl-2 polypeptides and fragments or analogs thereof can be made by those of skill in the art from the available Bcl-2 gene, cDNA, and protein sequences (e.g., GenBank).

Native Bax proteins, fragments thereof, or analogs thereof can be used as reagents in binding assays to detect binding to Bcl-2 and or binding to Bax for identifying agents that interfere with Bax function, said agents are thereby identified as candidate drugs which may be used, for example, to block apoptosis, to induce apoptosis (e.g., to treat lymphocytic leukemias), and the like. Typically, in vitro binding assays that measure binding of Bax to Bcl-2 employ native Bax (α or β isoform) that contains domain I and domain II. The Bcl-2 (or Bax) polypeptide is typically linked to a solid substrate by any of various means known to those of skill in the art; such linkage may be noncovalent (e.g., binding to a highly charged surface such as Nylon 66) or may be by covalent bonding (e.g., typically by chemical linkage). Bax polypeptides are typically labeled by incorporation of a radiolabeled amino acid or fluorescent label. The labeled Bax polypeptide is contacted with the immobilized Bcl-2 (or Bax) polypeptide under aqueous conditions that permit specific binding in control binding reactions with a binding affinity of about $1\times10^5$ $M^{-1}$ or greater (e.g., 10–250 mM NaCl or KCl and 5–100 mM Tris HCl pH 5–9, usually pH 6–8), generally including $Zn^{+2}$ and/or $Mn^{+2}$ and/or $Mg^{+2}$ in the nanomolar to micromolar range (1 nM to 999 μM). Specificity of binding is typically established by adding unlabeled competitor at various concentrations selected at the discretion of the practitioner. Examples of unlabeled protein competitors include, but are not limited to, the following: unlabeled Bax polypeptide, bovine serum albumin, and cellular protein extracts. Binding reactions wherein one or more agents are added are performed in parallel with a control binding reaction that does not include an agent. Agents which inhibit the specific binding of Bax polypeptides to Bcl-2 polypeptides and/or Bax polypeptides, as compared to a control reaction, are identified as candidate Bax modulating drugs.

Peptidomimetics

In addition to Bax polypeptides consisting only of naturally-occurring amino acids, Bax peptidomimetics are also provided. Peptide analogs are commonly used in the pharmaceutical industry as non-peptide drugs with properties analogous to those of the template peptide. These types of non-peptide compound are termed "peptide mimetics" or "peptidomimetics" (Fauchere, J. (1986) *Adv. Drug Res.* 15: 29; Veber and Freidinger (1985) *TINS* p.392; and Evans et al. (1987) *J. Med. Chem* 30: 1229, which are incorporated herein by reference) and are usually developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biological or pharmacological activity), such as human Bax, but have one or more peptide linkages optionally replaced by a linkage selected from the group consisting of: $—CH_2NH—$, $—CH_2S—$, $—CH_2—CH_2—$, $—CH{=}CH—$ (cis and trans), $—COCH_2—$, $—CH(OH)CH_2—$, and $—CH_2SO—$, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Spatola, A. F., Vega Data (March 1983), Vol. 1, Issue 3, "Peptide Backbone Modifications" (general review); Morley, J. S., *Trends Pharm Sci* (1980) pp. 463–468 (general review); Hudson, D. et al., *Int J Pept Prot Res* (1979) 14:177–185 ($—CH_2NH—$, $CH_2CH_2—$); Spatola, A. F. et al., *Life Sci* (1986) 38:1243–1249 ($—CH_2—S$); Hann, M. M., *J Chem Soc Perkin Trans I* (1982) 307–314 (—CH—CH—, cis and trans); Almquist, R. G. et al., *J Med Chem* (1980) 23:1392–1398 ($—COCH_2—$); Jennings-White, C. et al., *Tetrahedron Lett* (1982) 23:2533 ($—COCH_2—$); Szelke, M. et al., European Appln. EP 45665 (1982) CA: 97:39405 (1982) ($—CH(OH)CH_2—$); Holladay, M. W. et al., *Tetrahedron Lett* (1983) 24:4401–4404 ($—C(OH)CH_2—$); and Hruby, V. J., *Life Sci* (1982) 31:189–199 ($—CH_2—S—$); each of which is incorporated herein by reference. A particularly preferred non-peptide linkage is $—CH_2NH—$. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) to which the peptidomimetic binds to produce the therapeutic effect. Derivitization (e.g., labelling) of peptidomimetics should not substantially interfere with the desired biological or pharmacological activity of the peptidomimetic.

Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical concensus sequence variation may be generated by methods known in the art (Rizo and Gierasch (1992) *Ann. Rev. Bioch.* 61: 387, incorporated herein by reference); for example, by adding internal cysteine residues capable of forming intramolecular disulfide bridges which cyclize the peptide. Cyclic peptides comprising the sequence -WGR- (amino acids 107–109 of SEQ ID NO:2) and/or -QDN- (amino acids 32–34 of SEQ ID NO:2) and or -FRDG- (amino acids 5–8 of SEQ ID NO:12) frequently are preferred.

The amino acid sequences of Bax polypeptides identified herein will enable those of skill in the art to produce polypeptides corresponding to Bax peptide sequences and sequence variants thereof. Such polypeptides may be produced in prokaryotic or eukaryotic host cells by expression of polynucleotides encoding a Bax peptide sequence, frequently as part of a larger polypeptide. Alternatively, such peptides may be synthesized by chemical methods. Methods for expression of heterologous proteins in recombinant hosts, chemical synthesis of polypeptides, and in vitro translation are well known in the art and are described further in Maniatis et al., *Molecular Cloning: A Laboratory Manual* (1989), 2nd Ed., Cold Spring Harbor, N.Y.; Berger and Kimmel, *Methods in Enzymology, Volume* 152, *Guide to Molecular Cloning Techniques* (1987), Academic Press, Inc., San Diego, Calif; Merrifield, J. (1969) *J. Am. Chem. Soc.* 91: 501; Chaiken I. M. (1981) *CRC Crit. Rev. Biochem.* 11: 255; Kaiser et al.(1989) *Science* 243: 187; Merrifield, B. (1986) *Science* 232: 342; Kent, S. B. H. (1988) *Ann. Rev. Biochem.* 57: 957; and Offord, R. E. (1980) *Semisynthetic Proteins*, Wiley Publishing, which are incorporated herein by reference).

Peptides of the sequence N-W-G-R (amino acids 106–109 of SEQ ID NO:2) or W-G-R (amino acids 107–109 of SEQ ID NO:2) can be produced, typically by direct chemical synthesis, and used as agents to competitively inhibit Bax/Bcl-2 heterodimers formation. The N-W-G-R and W-G-R peptides are frequently produced as modified peptides, with nonpeptide moieties attached by covalent linkage to the N-terminus and/or C-terminus. In certain preferred embodiments, either the carboxy-terminus or the amino-terminus or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal modifications such as amidation, as well as other terminal modifications, including cyclization, may be incorporated into various embodiments of the invention. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Such N.W.G.R and W.G-R peptides may be used therapeuticaly to treat disease by altering the process of apoptosis in a cell population of a patient.

Production and Applications of α-Bax Antibodies

Native Bax proteins, fragments thereof, or analogs thereof, may be used to immunize an animal for the production of specific antibodies. These antibodies may comprise a polyclonal antiserum or may comprise a monoclonal antibody produced by hybridoma cells. For general methods to prepare antibodies, see *Antibodies: A Laboratory Manual*, (1988) E. Harlow and D. Lane, Cold Spring Harbor Laboratory, Cold Spring Harbor, N.Y., which is incorporated herein by reference.

For example but not for limitation, a recombinantly produced fragment of human Bax can be injected into a mouse along with an adjuvant following immunization protocols known to those of skill in the art so as to generate an immune response. Typically, approximately at least 1–50 μg of a Bax fragment or analog is used for the initial immunization, depending upon the length of the polypeptide. Alternatively or in combination with a recombinantly produced Bax polypeptide, a chemically synthesized peptide having a Bax sequence may be used as an immunogen to raise antibodies which bind a Bax protein, such as the native human Bax polypeptide having the sequence shown essentially in FIG. 3 or the native human Bax polypeptide having the sequence shown essentially in FIGS. 5 and 6. Immunoglobulins which bind the recombinant fragment with a binding affinity of at least $1\times10^7$ $M^{-1}$ can be harvested from the immunized animal as an antiserum, and may be further purified by immunoaffinity chromatography or other means. Additionally, spleen cells are harvested from the immunized animal (typically rat or mouse) and fused to myeloma cells to produce a bank of antibody-secreting hybridoma cells. The bank of hybridomas can be screened for clones that secrete immunoglobulins which bind the recombinantly produced Bax polypeptide (or chemically synthesized Bax polypeptide) with an affinity of at least $1\times10^6$ $M^{-1}$. Animals other than mice and rats may be used to raise antibodies; for example, goats, rabbits, sheep, and chickens may also be employed to raise antibodies reactive with a Bax protein. Transgenic mice having the capacity to produce substantially human antibodies also may be immunized and used for a source of α-Bax antiserum and/or for making monoclonal-secreting hybridomas.

Bacteriophage antibody display libraries may also be screened for binding to a Bax polypeptide, such as a full-length human Bax protein, a Bax fragment, or a fusion protein comprising a Bax polypeptide sequence comprising a Bax epitope (generally at least 3–5 contiguous amino acids). Generally such Bax peptides and the fusion protein portions consisting of bax sequences for screening antibody libraries comprise about at least 3 to 5 contiguous amino acids of Bax, frequently at least 7 contiguous amino acids of Bax, usually comprise at least 10 contiguous amino acids of Bax, and most ususally comprise a Bax sequence of at least 14 contiguous amino acids as shown in FIG. 3 or FIGS. 5 and 6. Combinatorial libraries of antibodies have been generated in bacteriophage lambda expression systems which may be screened as bacteriophage plaques or as colonies of lysogens (Huse et al. (1989) *Science* 246: 1275; Caton and Koprowski (1990) *Proc. Natl. Acad. Sci. (U.S.A.)* 87: 6450; Mullinax et al (1990) *Proc. Natl. Acad. Sci. (U.S.A.)* 87: 8095; Persson et al. (1991) *Proc. Natl. Acad. Sci. (U.S.A.)* 88: 2432). Various embodiments of bacteriophage antibody display libraries and lambda phage expression libraries have been described (Kang et al. (1991) *Proc. Natl. Acad. Sci. (U.S.A.)* 88: 4363; Clackson et al. (1991) *Nature* 352: 624; McCafferty et al. (1990) *Nature* 348: 552; Burton et al. (1991) *Proc. Natl. Acad. Sci. (U.S.A.)* 88: 10134; Hoogenboom et al. (1991) *Nucleic Acids Res.* 19: 4133; Chang et al. (1991) *J. Immunol.* 147: 3610; Breitling et al. (1991) *Gene* 104: 147; Marks et al. (1991) *J. Mol. Biol.* 222: 581; Barbas et al. (1992) *Proc. Natl. Acad. Sci. (U.S.A.)* 89: 4457; Hawkins and Winter (1992) *J. Immunol.* 22: 867; Marks et al. (1992) *Biotechnology* 10: 779; Marks et al. (1992) *J. Biol. Chem.* 267: 16007; Lowman et al (1991) *Biochemistry* 30: 10832; Lerner et al. (1992) *Science* 258: 1313, incorporated herein by reference). Typically, a bacteriophage antibody display library is screened with a Bax polypeptide that is immobilized (e.g., by covalent linkage to a chromatography resin to enrich for reactive phage by affinity chromatography) and/or labeled (e.g., to screen plaque or colony lifts).

Bax polypeptides which are useful as immunogens, for diagnostic detection of α-Bax antibodies in a sample, for diagnostic detection and quantitation of Bax protein in a sample (e.g., by standardized competitive ELISA), or for screening a bacteriophage antibody display library, are suitably obtained in substantially pure form, that is, typically about 50 percent (w/w) or more purity, substantially free of interfering proteins and contaminants. Preferably, these polypeptides are isolated or synthesized in a purity of at least 80 percent (w/w) and, more preferably, in at least about 95 percent (w/w) purity, being substantially free of other proteins of humans, mice, or other contaminants.

For some applications of these antibodies, such as identifying immunocrossreactive proteins, the desired antiserum or monoclonal antibody(ies) is/are not monospecific. In these instances, it may be preferable to use a synthetic or recombinant fragment of Bax as an antigen rather than using the entire native protein. More specifically, where the object is to identify immunocrossreactive polypeptides that comprise a particular structural moiety, such as a Bcl-2 binding domain, it is preferable to use as an antigen a fragment corresponding to part or all of a commensurate structural domain in the Bax protein. Production of recombinant or synthetic fragments having such defined amino- and carboxy-termini is provided by the Bax sequences shown in FIG. 3 and FIGS. 5 and 6.

If an antiserum is raised to a Bax fusion polypeptide, such as a fusion protein comprising a Bax immunogenic epitope fused to β-galactosidase or glutathione S-transferase, the antiserum is preferably preadsorbed with the non-Bax fusion partner (e.g, β-galactosidase or glutathione S-transferase) to deplete the antiserum of antibodies that react (i.e., specifically bind to) the non-Bax portion of the fusion protein that serves as the immunogen. Monoclonal or polyclonal antibodies which bind to the human and/or murine Bax protein can be used to detect the presence of human or murine Bax polypeptides in a sample, such as a Western blot of denatured protein (e.g., a nitrocellulose blot of an SDS-PAGE) obtained from a lymphocyte sample of a patient. Preferably quantitative detection is performed, such as by denistometric scanning and signal integration of a Western blot. The monoclonal or polyclonal antibodies will bind to the denatured Bax epitopes and may be identified visually or by other optical means with a labeled second antibody or labeled *Staphylococcus aureus* protein A by methods, known in the art.

One use of such antibodies is to screen cDNA expression libraries, preferably containing cDNA derived from human or murine mRNA from various tissues, for identifying clones containing cDNA inserts which encode structurally-related, immunocrossreactive proteins, that are candidate novel Bcl-2 binding factors or Bax-related proteins. Such screening of cDNA expression libraries is well known in the art, and is further described in Young et al., *Proc. Natl. Acad. Sci. U.S.A.* 80:1194–1198 (1983), which is incorporated herein by reference] as well as other published sources. Another use of such antibodies is to identify and/or purify immunocrossreactive proteins that are structurally or evolutionarily related to the native Bax protein or to the corresponding Bax fragment (e.g., functional domain; Bcl-2-binding domain) used to generate the antibody. The anti-Bax antibodies of the invention can be used to measure levels of Bax protein in a cell or cell population, for example in a cell explant (e.g., lymphocyte sample) obtained from a patient. When used in conjunctin with antibodies that specifically bind to Bcl-2, the anti-Bax antibodies of the present invention can be used to measure the ratio of Bax protein to Bcl-2 protein (i.e., Bax:Bcl-2 ratio) in a cell or cell population. The anti-Bax and anti-Bcl-2 antibodies can be used to measure the corresponding protein levels (Bax or Bcl-2, respectively) by various methods, including but not limited to: (1) standardized ELISA on cell extracts, (2) immunoprecipitation of cell extracts followed by polyacrylamide gel electrophoresis of the immunoprecipitated products and quantitative detection of the band(s) corresponding to Bax and/or Bcl-2, and (3) in situ detection by immmunohistochemical straining with the anti-Bax and/or anti-Bcl-2 antibodies and detection with a leabeled second antibody. The measurement of the Bax:Bcl-2 ratio in a cell or cell population is informative regarding the apoptosis status of the cell or cell population.

Various other uses of such antibodies are to diagnose and/or stage leukemias or other neoplasms, and for therapeutic application (e.g., as captionized antibodies or by targeted liposomal delivery) to treat neoplasia, autoimmune disease, AIDS, and the like.

Bax Polynucleotides

Disclosure of the full coding sequences for murine and human Bax shown in FIG. 3 and FIGS. 5 and 6 makes possible the construction of isolated polynucleotides that can direct the expression of Bax, fragments thereof, or analogs thereof. Further, the sequences in FIG. 3 and FIGS. 5 and 6 make possible the construction of nucleic acid hybridization probes and PCR primers that can be used to detect RNA and DNA sequences encoding Bax.

Polynucleotides encoding full-length Bax or fragments or analogs thereof, may include sequences that facilitate transcription (expression sequences) and translation of the coding sequences, such that the encoded polypeptide product is produced. Construction of such polynucleotides is well known in the art and is described further in Maniatis et al., *Molecular Cloning: A Laboratory Manual*, 2nd Ed. (1989), Cold Spring Harbor, N.Y. For example, but not for limitation, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector. A typical eukaryotic expression cassette will include a polynucleotide sequence encoding a Bax polypeptide linked downstream (i.e., in translational reading frame orientation; polynucleotide linkage) of a promoter such as the HSV tk promoter or the pgk (phosphoglycerate kinase) promoter, optionally linked to an enhancer and a downstream polyadenylation site (e.g., an SV40 large T Ag poly A addition site).

Preferably, these amino acid sequences occur in the given order (in the aminoterminal to carboxyterminal orientation) and may comprise other intervening and/or terminal sequences; generally such polypeptides are less than 1000 amino acids in length, more usually less than about 500 amino acids in lengths, and frequently approximately 41 to 218 amino acids in length (e.g., 192 amino acids or 218 amino acids; $\alpha$ or $\beta$ human isoforms). The degeneracy of the genetic code gives a finite set of polynucleotide sequences encoding these amino acid sequences; this set of degenerate sequences may be readily generated by hand or by computer using commercially available software (Wisconsin Genetics Software Package Release 7.0). Isolated Bax polynucleotides typically are less than approximately 10,000 nucleotides in length.

Additionally, where expression of a polypeptide is not desired, polynucleotides of this invention need not encode a functional protein. Polynucleotides of this invention may serve as hybridization probes and/or PCR primers (amplimers) and/or LCR oligomers for detecting Bax RNA or DNA sequences.

Alternatively, polynucleotides of this invention may serve as hybridization probes or primers for detecting RNA or DNA sequences of related genes, such genes may encode structurally or evolutionarily related proteins. For such hybridization and PCR applications, the polynucleotides of the invention need not encode a functional polypeptide. Thus, polynucleotides of the invention may contain substantial deletions, additions, nucleotide substitutions and/or transpositions, so long as specific hybridization or specific amplification to a Bax sequence is retained.

Specific hybridization is defined hereinbefore, and can be roughly summarized as the formation of hybrids between a polynucleotide of the invention (which may include substitutions, deletions, and/or additions) and a specific target polynucleotide such as murine or human Bax mRNA so that a single band corresponding to each isoform present is identified on a Northern blot of RNA prepared from Bax-expressing cells (i.e., hybridization and washing conditions can be established that permit detection of discrete Bax mRNA band(s)). Thus, those of ordinary skill in the art can prepare polynucleotides of the invention, which may include substantial additions, deletions, substitutions, or transpositions of nucleotide sequence as compared to sequences shown in FIG. 3 or FIGS. 5 and 6, and determine whether specific hybridization is a property of the polynucleotide by performing a Northern blot using RNA prepared from a lymphocyte cell line which expresses Bax mRNA and/or by hybridization to a Bax DNA clone (cDNA or genomic clone).

Specific amplification is defined as the ability of a set of PCR amplimers, when used together in a PCR reaction with a Bax polynucleotide, to produce substantially a single major amplification product which corresponds to a Bax gene sequence or mRNA sequence. Generally, human genomic DNA or mRNA from Bax expressing human cells (e.g., Jurkat cell line) is used as the template DNA sample for the PCR reaction. PCR amplimers that exhibit specific amplification are suitable for quantitative determination of Bax mRNA by quantitative PCR amplification. Bax allele-specific amplification products, although having sequence and/or length polymorphisms, are considered to constitute a single amplification product for purposes of this definition.

Generally, hybridization probes comprise approximately at least 10 and preferably 25 consecutive nucleotides of a sequence shown in FIG. 3 or FIGS. 5 and 6 (for human and murine Bax detection), preferably the hybridization probes contain at least 50 consecutive nucleotides of a sequence shown in FIG. 3 or FIGS. 5 and 6, and more preferably comprise at least 100 consecutive nucleotides of a sequence shown in FIG. 3 or FIGS. 5 and 6. PCR amplimers typically comprise approximately 25 to 50 consecutive nucleotides of a sequence shown in FIG. 3 or FIGS. 5 and 6, and usually consist essentially of approximately 25 to 50 consecutive nucleotides of a sequence shown in FIG. 3 or FIGS. 5 and 6 with additional nucleotides, if present, generally being at the 5' end so as not to interfere with polymerase-mediated chain extension. PCR amplimer design and hybridization probe selection are well within the scope of discretion of practitioners of ordinary skill in the art.

Methods of Identifying Novel and Apoptosis-Modulating Agents

A basis of the present invention is the experimental finding that a novel protein, Bax, is present in many cell types which undergo apoptosis and Bax binds specifically to Bcl-2, a protein known to modulate (inhibit) apoptosis in cells. For example, agents which block Bax function and/or block Bcl-2 function may be developed as potential human therapeutic drugs.

Therapeutic agents which inhibit cell death by modulating Bcl-2-dependent inhibition of Bax function (i.e., formation of Bax/Bax homodimers and/or induction of apoptosis), for example by augmenting formation of Bcl-2/Bax heterodimers and thereby reducing formation of Bax/Bax homodimers, can be used as pharmaceuticals. Such pharmaceuticals will be used to treat a variety of human a veterinary diseases, such as: reperfusion injury, myocardial infarction, stroke, traumatic brain injury, neurodegenerative diseases, aging, ischemia, toxemia, infection, AIDS, hepatitis, and the like.

Therapeutic agents which augment (induce) cell death by modulating the levels of Bax/Bcl-2 heterodimers and Bax/Bax homodimers can be used as pharmaceuticals. Such pharmaceuticals can be used to treat a variety of diseases including but not limited to: hyperplasia, neoplasia, autoimmune diseases, transplant rejection, lymphoproliferative diseases, and the like.

Candidate antineoplastic agents are then tested further for antineoplastic activity in assays which are routinely used to predict suitability for use as human antineoplastic drugs. Examples of these assays include, but are not limited to: (1) ability of the candidate agent to inhibit the ability of anchorage-independent transformed cells to grow in soft agar, (2) ability to reduce tumorigenicity of transformed cells transplanted into nu/nu mice, (3) ability to reverse morphological transformation of transformed cells, (4) ability to reduce growth of transplanted tumors in nu/nu mice, (5) ability to inhibit formation of tumors or preneoplastic cells in animal models of spontaneous or chemically-induced carcinogenesis, and (6) ability to induce a more differentiated phenotype in transformed cells to which the agent is applied.

Bax/Bcl-2 Intermolecular Binding

A basis of the present invention is the surprising finding that the Bax protein forms a complex with the Bcl-2 protein under physiological conditions. This finding indicates that the Bax protein serves as a modulator of Bcl-2 function, and vice versa. Such functional modulation can serve to couple a signal transduction pathway (via Bax) to an apoptosis regulatory protein (i.e., Bcl-2).

Assays for detecting the ability of agents to inhibit or augment the binding of Bax to Bcl-2 provide for facile high-throughput screening of agent banks (e.g., compound libraries, peptide libraries, and the like) to identify Bax or Bcl-2 antagonists or agonists. Such Bax or Bcl-2 antagonists and agonists may modulate Bax and/or Bcl-2 activity and thereby modulate apoptosis.

Administration of an efficacious dose of an agent capable of specifically inhibiting Bax/Bcl-2 complex formation or Bcl-2/Bcl-2 complex formation to a patient can be used as a therapeutic or prophylactic method for treating pathological conditions (e.g., cancer, inflammation, lymphoproliferative diseases, autoimmune disease, neurodegenerative diseases, and the like) which are effectively treated by modulating Bax and/or Bcl-2 activity and apoptosis.

Binding assays generally take one of two forms: immobilized Bax polypeptide(s) can be used to bind labeled Bcl-2 polypeptide(s), or conversely, immobilized Bcl-2 polypeptide(s) can be used to bind labeled Bax polypeptides. Alternatively, a binding assay can be performed to detect binding of a Bax polypeptide to form a homodimer with a Bax polypeptide; typically, a labeled Bax polypeptide is contacted with an immobilized Bax polypeptide under aqueous binding conditions and the extent of binding is determined by measuring the amount of immobilized labeled Bax. In each case, the labeled polypeptide is contacted with the immobilized polypeptide under aqueous conditions that permit specific binding of the polypeptides(s) to form a Bax/Bcl-2 complex in the absence of added agent. Particular aqueous conditions may be selected by the practitioner according to conventional methods. For general guidance, the following buffered aqueous conditions may be used: 10–250 mM NaCl, 5–50 mM Tris HCl, pH 5–8, with optional addition of divalent cation(s) and/or metal chelators and/or nonionic detergents and/or membrane fractions. It is appreciated by those in the art that additions, deletions, modifications (such as pH) and substitutions (such as KCl substituting for NaCl or buffer substitution) may be made to these basic conditions. Modifications can be made to the basic binding reaction conditions so long as specific binding of Bax polypeptide(s) to Bcl-2 polypeptides occurs in the control reaction(s). In some embodiments, where the assay detects formation of Bax/Bax homodimers, modifications can be made to the basic binding reaction conditions so long as specific binding of a Bax polypeptide to a Bax polypeptides occurs in the control reaction(s). Conditions that do not permit specific binding in control reactions (no agent included) are not suitable for use in binding assays.

Preferably, at least one polypeptide species is labeled with a detectable marker. Suitable labeling includes, but is not limited to, radiolabeling by incorporation of a radiolabeled amino acid (e.g., $^{14}C$-labeled leucine, $^{3}H$-labeled glycine, $^{35}S$-labeled methionine), radiolabeling by post-translational radioiodination with $^{125}I$ or $^{131}I$ (e.g., Bolton-Hunter reaction and chloramine T), labeling by post-translational phosphorylation with $^{32}P$ (e.g., phosphorylase and inorganic radiolabeled phosphate) fluorescent labeling by incorporation of a fluorescent label (e.g., fluorescein or rhodamine), or labeling by other conventional methods known in the art. In embodiments where one of the polypeptide species is immobilized by linkage to a substrate, the other polypeptide is generally labeled with a detectable marker.

Additionally, in some embodiments a Bax or Bcl-2 polypeptide may be used in combination with an accessory protein (e.g., a protein which forms a complex with the polypeptide in vivo), it is preferred that different labels are used for each polypeptide species, so that binding of individual and/or heterodimeric and/or multimeric complexes can be distinguished. For example but not limitation, a Bax polypeptide may be labeled with fluorescein and an accessory polypeptide may be labeled with a fluorescent marker that fluorescesces with either a different excitation wavelength or emission wavelength, or both. Alternatively, double-label scintillation counting may be used, wherein a Bax polypeptide is labeled with one isotope (e.g., $^{3}H$) and a second polypeptide species is labeled with a different isotope (e.g., $^{14}C$) that can be distinguished by scintillation counting using discrimination techniques.

Labeled polypeptide(s) are contacted with immobilized polypeptide(s) under aqueous conditions as described herein. The time and temperature of incubation of a binding reaction may be varied, so long as the selected conditions permit specific binding to occur in a control reaction where no agent is present. Preferable embodiments employ a reaction temperature of about at least 15 degrees Centigrade, more preferably 35 to 42 degrees Centigrade, and a time of incubation of approximately at least 15 seconds, although longer incubation periods are preferable so that, in some embodiments, a binding equilibrium is attained. Binding kinetics and the thermodynamic stability of bound Bax/Bcl-2 complexes determine the latitude available for varying the time, temperature, salt, pH, and other reaction conditions. However, for any particular embodiment, desired binding reaction conditions can be calibrated readily by the practitioner using conventional methods in the art, which may include binding analysis using Scatchard analysis, Hill analysis, and other methods (*Proteins, Structures and Molecular Principles*, (1984) Creighton (ed.), W.H. Freeman and Company, New York).

Specific binding of labeled Bax or Bcl-2 polypeptide to immobilized Bcl-2 or Bax polypeptide, respectively, is determined by including unlabeled competitor protein(s) (e.g., albumin). After a binding reaction is completed, labeled polypeptide(s) that is/are specifically bound to immobilized polypeptide is detected. For example and not for limitation, after a suitable incubation period for binding, the aqueous phase containing non-immobilized protein is removed and the substrate containing the immobilized polypeptide species and any labeled protein bound to it is washed with a suitable buffer, optionally containing unlabeled blocking agent(s), and the wash buffer(s) removed. After washing, the amount of detectable label remaining specifically bound to the immobilized polypeptide is determined (e.g., by optical, enzymatic, autoradiographic, or other radiochemical methods).

In some embodiments, addition of unlabeled blocking agents that inhibit non-specific binding are included. Examples of such blocking agents include, but are not limited to, the following: calf thymus DNA, salmon sperm DNA, yeast RNA, mixed sequence (random or pseudorandom sequence) oligonucleotides of various lengths, bovine serum albumin, nonionic detergents (NP-40, Tween, Triton X-100, etc.), nonfat dry milk proteins, Denhardt's reagent, polyvinylpyrrolidone, Ficoll, and other blocking agents. Practitioners may, in their discretion, select blocking agents at suitable concentrations to be included in binding assays; however, reaction conditions are selected so as to permit specific binding between a Bax polypeptide and a Bcl-2 polypeptide in a control binding reaction. Blocking agents are included to inhibit nonspecific binding of labeled protein to immobilized protein and/or to inhibit nonspecific binding of labeled polypeptide to the immobilization substrate.

In embodiments where a polypeptide is immobilized, covalent or noncovalent linkage to a substrate may be used. Covalent linkage chemistries include, but are not limited to, well-characterized methods known in the art (Kadonaga and Tijan (1986) *Proc. Natl. Acad. Sci. (U.S.A.)* 83: 5889). One example, not for limitation, is covalent linkage to a substrate derivatized with cyanogen bromide (such as CNBr-derivatized Sepharose 4B). It may be desirable to use a spacer to reduce potential steric hindrance from the substrate. Noncovalent bonding of proteins to a substrate include, but are not limited to, bonding of the protein to a charged surface and binding with specific antibodies.

In one class of embodiments, parallel binding reactions are conducted, wherein one set of reactions serves as control and at least one other set of reactions include various quantities of agents, mixtures of agents, or biological extracts, that are being tested for the capacity to inhibit binding of a Bax polypeptide to a Bcl-2 polypeptide, and/or to inhibit binding of a Bax polypeptide to form homomultimers (homodimers) with a Bax polypeptide.

Yeast Two-Hybrid Screening Assays

Yeast comprising (1) an expression cassette encoding a GAL4 DNA binding domain (or GAL4 activator domain) fused to a binding fragment of Bcl-2 capable of binding to a Bax polypeptide, (2) an expression cassette encoding a GAL4 DNA activator domain (or GAL4 binding domain, respectively) fused to a binding fragment of Bax capable of binding to a Bcl-2 polypeptide, and (3) a reporter gene (e.g., β-galactosidase) comprising a cis-linked GAL4 transcriptional response element can be used for agent screening. Such yeast are incubated with a test agent and expression of the reporter gene (e.g., β-galactosidase) is determined; the capacity of the agent to inhibit expression of the reporter gene as compared to a control culture identifies the agent as a candidate Bcl-2-modulatory agent or Bax modulatory agent.

Yeast two-hybrid systems may be used to screen a mammalian (typically human) cDNA expression library, wherein cDNA is fused to a GAL4 DNA binding domain or activator domain, and either a Bax or Bcl-2 polypeptide sequence is fused to a GAL4 activator domain or DNA binding domain, respectively. Such a yeast two-hybrid system can screen for cDNAs that encode proteins which bind to Bax or Bcl-2 sequences. For example, a cDNA library can be produced from mRNA from a human mature B cell (Namalwa) line (Ambrus et al. (1993) *Proc. Natl. Acad. Sci. (U.S.A.))* or other suitable cell type. Such a cDNA library cloned in a yeast two-hybrid expression system (Chien et al. (1991) *Proc. Natl. Acad. Sci. (U.S.A.)* 88: 9578) can be used to identify cDNAs which encode proteins that interact with Bax or Bcl02 and thereby produce expression of the GAL4-dependent reporter gene. Polypeptides which interact with Bax or Bcl-2 can also be identified by immunoprecipitation of Bax or Bcl-2 with antibody and identification of co-precipitating species. Further, polypeptides that bind Bax or Bcl-2 can be identified by screening a peptide library (e.g., a bacteriophage peptide display library, a spatially defined VLSIPS peptide array, and the like) with a Bax or Bcl-2 polypeptide.

Antisense Polynucleotides

Additional embodiments directed to modulation of neoplasia or apoptosis include methods that employ specific antisense polynucleotides complementary to all or part of the sequences shown in FIG. 3 or FIGS. 5 and 6. Such complementary antisense polynucleotides may include nucleotide substitutions, additions, deletions, or transpositions, so long as specific hybridization to the relevant target sequence corresponding to FIG. 3 or FIGS. 5 and 6 is retained as a functional property of the polynucleotide. Complementary antisense polynucleotides include soluble antisense RNA or DNA oligonucleotides which can hybridize specifically to Bax mRNA species and prevent transcription of the mRNA species and/or translation of the encoded polypeptide (Ching et al. (1989) *Proc. Natl. Acad. Sci. U.S.A.* 86: 10006; Broder et al. (1990) *Ann. Int. Med.* 113: 604; Loreau et al. (1990) *FEBS Letters* 274: 53; Holcenberg et al., WO91/11535; U.S. Ser. No. 07/530,165; WO91/09865; WO91/04753; WO90/13641; and EP 386563, each of which is incorporated herein by reference). The antisense polynucleotides therefore inhibit production of Bax polypeptides. Antisense polynucleotides that prevent transcription and/or translation of mRNA corresponding to Bax polypeptides may inhibit apoptosis, senescence, AIDS, and the like, and/or reverse the transformed phenotype of cells. Antisense polynucleotides of various lengths may be produced, although such antisense polynucleotides typically comprise a sequence of about at least consecutive nucleotides which are substantially identical to a naturally-occurring Bax polynucleotide sequence, and typically which are identical to a sequence shown in FIG. 3 or FIGS. 5 or 6.

Antisense polynucleotides may be produced from a heterologous expression cassette in a transfectant cell or transgenic cell, such as a transgenic pluripotent hematopoietic stem cell used to reconstitute all or part of the hematopoietic stem cell population of an individual. Alternatively, the antisense polynucleotides may comprise soluble oligonucleotides that are administered to the external milieu, either in the culture medium in vitro or in the circulatory system or interstitial fluid in vivo. Soluble antisense polynucleotides present in the external milieu have been shown to gain access to the cytoplasm and inhibit translation of specific mRNA species. In some embodiments the antisense polynucleotides comprise methylphosphonate moieties. For general methods relating to antisense polynucleotides, see *Antisense RNA and DNA*, (1988), D. A. Melton, Ed., Cold Spring Harbor Laboratory, Cold Spring Harbor, N.Y.).

Transgenic Animal Embodiments

Genomic clones of Bax, particularly of the murine cognate Bax gene, may be used to construct homologous targeting constructs for generating cells and transgenic nonhuman animals having at least one functionally disrupted Bax allele. Guidance for construction of homologous targeting constructs may be found in the art, including: Rahemtulla et al. (1991) *Nature* 353: 180; Jasin et al. (1990) *Genes Devel.* 4: 157; Koh et al. (1992) *Science* 256: 1210; Molina et al. (1992) *Nature* 357: 161; Grusby et al. (1991) *Science* 253: 1417; Bradley et al. (1992) *Bio/Technology* 10: 534. Homologous targeting can be used to generate so-called "knockout" mice, which are heterozygous or homozygous for an inactivated Bax allele. Such mice may be sold commercially as research animals for investigation of immune system development, neoplasia, apoptosis, and other uses.

Chimeric targeted mice are derived according to Hogan, et al., *Manipulating the Mouse Embryo: A Laboratory Manual*, Cold Spring Harbor Laboratory (1988) and *Teratocarcinomas and Embryonic Stem Cells: A Practical Approach*, E. J. Robertson, ed., IRL Press, Washington, D.C., (1987). Embryonic stem cells are manipulated according to published procedures (*Teratocarcinomas and Embryonic Stem Cells: A Practical Approach*, E. J. Robertson, ed., IRL Press, Washington, D.C. (1987); Zjilstra et al. (1989) *Nature* 342:435; and Schwartzberg et al. (1989) *Science* 246: 799.

Additionally, a Bax cDNA or genomic gene copy may be used to construct transgenes for expressing Bax polypeptides at high levels and/or under the transcriptional control of transcription control sequences which do not naturally occur adjacent to the Bax gene. For example but not limitation, a constitutive promoter (e.g., a CMV or pgk promoter) or a cell-lineage specific transcriptional regulatory sequence (e.g., an LCK or immunoglobin gene promoter/enhancer) have been operably linked to a Bax-encoding polynucleotide sequence to form a transgene. Such transgenes can be introduced into cells (e.g., fertilized eggs, ES cells, hematopoietic stem cells) and transgenic cells and transgenic nonhuman animals may be obtained according to conventional methods. Transgenic cells and/or transgenic nonhuman animals may be used to screen for antineoplastic agents and/or to screen for potential carcinogens or agents that modulate apoptosis, as overexpression of Bax or inappropriate expression of Bax may result in a preneoplastic or neoplastic state, may prevent neoplastic development, or may produce premature senescence or depletion or ablation of specific lymphocyte compartments.

Identification and Isolation of Proteins That Bind Bax

Proteins that bind to Bax and/or a Bax/Bcl-2 complex are potentially important regulatory proteins. Such proteins may be targets for novel antineoplastic agents and other novel drugs. These proteins are referred to herein as accessory proteins. Accessory proteins may be isolated by various methods known in the art.

One preferred method of isolating accessory proteins is by contacting a Bax polypeptide in a cell extract to an antibody that binds the Bax polypeptide, and isolating resultant immune complexes. These immune complexes may contain accessory proteins bound to the Bax polypeptide. The accessory proteins may be identified and isolated by denaturing the immune complexes with a denaturing agent and, preferably, a reducing agent. The denatured, and preferably reduced, proteins can be electrophoresed on a polyacrylamide gel. Putative accessory proteins can be identified on the polyacrylamide gel by one or more of various well known methods (e.g., Coomassie staining, Western blotting, silver staining, etc.), and isolated by resection of a portion of the polyacrylamide gel containing the relevant identified polypeptide and elution of the polypeptide is from the gel portion.

Yeast two-hybrid systems wherein on GAL4 fusion protein comprises a Bax polypeptide sequence, typically a full-length of near full-length Bax polypeptide sequence (e.g., the sequence of FIG. 3), and the other GAL4 fusion protein comprises a cDNA library member can be used to identify cDNAs encoding Bax-interacting proteins, according to the general method of Chien et al. (1991) op.cit. Alternatively, an *E. coli*/BCCP interactive screening system (Germino et al. (1993) *Proc. Natl. Acad. Sci. (U.S.A.)* 90: 1639, incorporated herein by reference) can be used to identify Bax-interacting protein sequences. Also, an expression library, such as λgtll cDNA expression library (Dunn et al. (1989) *J. Biol. Chem.* 264: 13057), can be screened with a labelled Bax polypeptide to identify cDNAs encoding polypeptides which specifically bind Bax. For these procedures, cDNA libraries usually comprise mammalian cDNA populations, typically human, mouse, or rat, and may represent cDNA produced from RNA and one cell type, tissue, or organ and one or more developmental stage. Specific binding for screening cDNA expression libraries is usually provided by including one or more blocking agent (e.g., albumin, nonfat dry milk solids, etc.) prior to and/or concomitant with contacting the labeled Bax polypeptide (and/or labeled anti-Bax antibody).

A putative accessory protein may be identified as an accessory protein by demonstration that the protein binds to Bax and/or a Bax/Bcl-2 complex. Such binding may be shown in vitro by various means, including, but not limited to, binding assays employing a putative accessory protein that has been renatured subsequent to isolation by a polyacrylamide gel electrophoresis method. Alternatively, binding assays employing recombinant or chemically synthesized putative accessory protein may be used. For example, a putative accessory protein may be isolated and all or part of its amino acid sequence determined by chemical sequencing, such as Edman degradation. The amino acid sequence information may be used to chemically synthesize the putative accessory protein. The amino acid sequence may also be used to produce a recombinant putative accessory protein by: (1) isolating a cDNA clone encoding the putative accessory protein by screening a cDNA library with degenerate oligonucleotide probes according to the amino acid sequence data, (2) expressing the cDNA in a host cell, and (3) isolating the putative accessory protein.

Putative accessory proteins that bind Bax and/or Bax/Bcl-2 complex in vitro are identified as accessory proteins. Accessory proteins may also be identified by crosslinking in vivo with bifunctional crosslinking reagents (e.g., dimethylsuberimidate, glutaraldehyde, etc.) and subsequent isolation of crosslinked products that include a Bax polypeptide. For a general discussion of cross-linking, see Kunkel et al. (1981) *Mol. Cell. Biochem.* 34:3. Preferably, the bifunctional crosslinking reagent will produce crosslinks which may be reversed under specific conditions after isolation of the crosslinked complex so as to facilitate isolation of the accessory protein from the Bax polypeptide. Isolation of crosslinked complexes that include a Bax polypeptide is preferably accomplished by binding an antibody that binds a Bax polypeptide with an affinity of at least $1\times10^7$ $M^{-1}$ to a population of crosslinked complexes and recovering only those complexes that bind to the antibody with an affinity of at least $1\times10^7$ $M^{-1}$. Polypeptides that are crosslinked to a Bax polypeptide are identified as accessory proteins.

Screening assays can be developed for identifying candidate antineoplastic agents as being agents which inhibit binding of Bax to an accessory protein under suitable binding conditions.

Methods for Forensic Identification

The Bax polynucleotide sequences of the present invention can be used for forensic identification of individual humans, such as for identification of decedents, determination of paternity, criminal identification, and the like. For example but not limitation, a DNA sample can be obtained from a person or from a cellular sample (e.g., crime scene evidence such as blood, saliva, semen, and the like) and subjected to RFLP analysis, allele-specific PCR, or PCR cloning and sequencing of the amplification product to determine the structure of the Bax gene region. On the basis of the Bax gene structure, the individual from which the sample originated will be identified with respect to his/her Bax genotype. The Bax genotype may be used alone or in conjunction with other genetic markers to conclusively identify an individual or to rule out the individual as a possible perpetrator.

In one embodiment, human genomic DNA samples from a population of individuals (typically at least 50 persons from various racial origins) are individually aliquoted into reaction vessels (e.g., a well on a microtitre plate). Each aliquot is digested (incubated) with one or more restriction enzymes (e.g., EcoRI, HindIII, SmaI, BamHI, SalI, NotI, AccI, ApaI, BglII, XbaI, PstI) under suitable reaction conditions (e.g., see New England Biolabs 1993 catalog). Corresponding digestion products from each individual are loaded separately on an electrophoretic gel (typically agarose), electrophoresed, blotted to a membrane by Southern blotting, and hybridized with a labeled Bax probe (e.g., a full-length human Bax cDNA sequence of FIG. 3 or FIGS. 5 and 6). Restriction fragments (bands) which are polymorphic among members of the population are used as a basis to discriminate Bax genotypes and thereby classify individuals on the basis of their Bax genotype.

Similar categorization of Bax genotypes may be performed by sequencing PCR amplification products from a population of individuals and using sequence polymorphisms to identify alleles (genotypes), and thereby identify or classify individuals.

Methods of Rational Drug Design

Bax and Bcl-2 polypeptides, especially those portions which form direct contacts in Bax/Bcl-2 heterodimers, can be used for rational drug design of candidate bcl-2-modulating agents (e.g., antineoplastics and immunomodulators). The substantially purified Bax/Bcl-2 heterodimers and the identification of Bax as a docking partner for Bcl-2 as provided herein permits production of substantially pure Bax/Bcl-2 polypeptide complexes and computational models which can be used for protein X-ray crystallography or other structure analysis methods, such as the DOCK program (Kuntz et al (1982) *J. Mol. Biol.* 161: 269; Kuntz ID (1992) *Science* 257: 1078) and variants thereof. Potential therapeutic drugs may be designed rationally on the basis of structural information thus provided. In one embodiment, such drugs are designed to prevent formation of a Bax polypeptide: Bcl-2 polypeptide complex. Thus, the present invention may be used to design drugs, including drugs with a capacity to inhibit binding of Bax to Bcl-2.

The following examples are given to illustrate the invention, but are not to be limiting thereof. All percentages given throughout the specification are based upon weight unless otherwise indicated. All protein molecular weights are based on mean average molecular weights unless otherwise indicated.

The nomenclature used hereafter and the laboratory procedures in cell culture, molecular genetics, and nucleic acid chemistry and hybridization described below may involve well known and commonly employed procedures in the art. Standard techniques are used for recombinant nucleic acid methods, polynucleotide synthesis, and microbial culture and transformation (e.g., electroporation, lipofection). The techniques and procedures are generally performed according to conventional methods in the art and various general references (see, generally, Sambrook et al. Molecular Cloning: A Laboratory Manual, 2d ed. (1989) Cold Spring Harbor Laboratory Press, Cold Spring Harbor, N.Y., which is incorporated herein by reference) which are provided throughout this document.

Oligonucleotides can be synthesized on an Applied Bio Systems oligonucleotide synthesizer according to specifications provided by the manufacturer.

Methods for PCR amplification are described in the art (*PCR Technology: Principles and Applications for DNA Amplification* ed. H A Erlich, Freeman Press, New York, N.Y. (1992); *PCR Protocols: A Guide to Methods and Applications*, eds. Innis, Gelfland, Snisky, and White, Academic Press, San Diego, Calif. (1990); Mattila et al. (1991) *Nucleic Acids Res.* 19: 4967; Eckert, K. A. and Kunkel, T. A. (1991) *PCR Methods and Applications* 1: 17; *PCR*, eds. McPherson, Quirkes, and Taylor, IRL Press, Oxford; and U.S. Pat. No. 4,683,202, which are incorporated herein by reference).

The experimental procedures, reagents, starting materials and test procedures performed herein used the following techniques.

A) Cell Culture

RL7, a human B cell line which bears the t(14;18) and expresses high levels of Bcl-2 was maintained in Iscove's modified Dulbecco's medium supplemented with 10% fetal calf serum (FCS)(supplied by Gibco). The interleukin-3 (IL-3) dependent murine cell line FL5.12, a lymphoid progenitor clone, and all its derivatives were maintained in Iscove's modified Dulbecco's medium supplemented with 10% FCS and 10% WEHI-3B conditional medium as a source of IL-3.

B) Antibodies

The 6C8, human Bcl-2 specific hamster moAb (Hockenbery et al., 1990); the 12CA5, influenza virus hemagglutinin protein epitope specific murine moAb (Kolodziej and Young, 1991); the 3F11, murine Bcl-2 specific hamster moAb (Veis et al, 1993) were used. 124, a human Bcl-2 specific murine moAb was purchased from DAKO. TN3 19.12, a human TNF specific hamster moAb (Sheehan et al., 1989), was used as a control antibody. For Western immunostaining, the primary antibody dilutions were: 6C8 (1:100), 3F11 (1:100), 12CA5 (1:50). The 3F11 antibody was directly biotinylated, as described (Veis et al.,1993) for immunoblots. The other antibodies were detected with species specific biotinylated secondary antibodies.

C) Immunoprecipitation and Western blotting

Prior to metabolic labeling, cells were washed once in prewarmed, serum-free, methionine-free Dulbecco's medium. Cells were resuspended at 3–5x$10^6$ cells/ml in methionine-free Dulbecco's medium supplemented with 10% dialyzed FCS and either 5% complete medium or 5% WEHI 3B supernatant. Metabolic labeling was performed with 40 uCi/ml of ($^{35}$S)methionine, ($^{35}$S)cysteine for 9–12 hours before lysis. All steps of the immunoprecipitation were carried out on ice or in the cold room. Cells were washed twice with cold phosphate-buffered saline and lysed in an NP-40 isotonic lysis buffer with freshly added protease inhibitors (142.5 mM KCl, 5 mM MgCl2, 10 mM HEPES pH:7.2, 1 mM EGTA, 0.2% NP-40, 0.2 mM phenylmethylsulfonyl fluoride, 0.1% Aprotinin, 0.7 ug/ml Pepstatin and 1 ug/ml Leupeptin) by nutation for 30'. Nuclei and unlysed cellular debris were removed by centrifugation at 215,000×g for 10'. Lysates were precleared with 10% v/v Protein A-Sepharose (Prot.A-S) for 30' which was removed by centrifugation at 400×g for 2'. In experiments, the lysates were also mixed with 10× excess cold cells lysates for 15' prior to the addition of the antibody. Specific antibodies were added for 90' and immunoprecipitates were captured with 10% v/v Prot.A-S for 60'. In some experiments, supernatants of the primary immunoprecipitation were precleared again with 10% v/v Prot.A-S for 30', and reprecipitated with an appropriate second antibody. Immunoprecipitates were washed (unless indicated otherwise) once in lysis buffer followed by a wash in lysis buffer without NP-40. Immunoprecipitates were solubilized with SDS-PAGE sample buffer and electrophoresed through 12.5% SDS-polyacrylamide gels. Gels containing ($^{35}$S) methionine labeled proteins were fixed with 10% glacial acetic acid and 30% methanol overnight, enhanced by impregnating with a commercial fluorography enhancing solution (Enhance by DuPont) for 60', and precipitated in water for 30'. Gels were then dried and autoradiography performed at −70° C.

For immunoblots, proteins were electrotransferred overnight at 4° C. on nitrocellulose membranes. Filters were blocked for 2 hours with phosphate-buffered saline containing 3% non-fat milk. All additional immunostaining steps were performed in phosphate-buffered saline with 0.05% Tween-20 (PBS-Tween) at room temperature. Filters were incubated with primary antibody for 2 hours. Species specific biotinylated secondary antibodies (1:300) were also reacted for 2 hours. Immunoblots were reacted with horseradish-peroxidase-Streptavidin (1:1000) for 1 hour. Filters were washed in PBX-Tween 4 times for 5' between each step and were developed with diazobenzidine (BioRad) enhanced with nickel chloride (0.03%).

D) Peptide Sequencing

For protein isolation 1x$10^9$ RL-7 or FL5.12-hBcl-2 cells were immunoprecipitated in large scale preparations, as described above. Immunoprecipitates were electrophoresed through a 3 mm thick preparative 12.5% SDS-polyacrylamide gel, stained with Coomassie blue dye for 10' and destained for 20'. Appropriate protein bands were excised from the gel and partially digested with an optimized amount of *S. aureus* V8 protease (Calbiochem) "in gel", as described (Cleveland et al, 1976). Following separation on a second 17.5% SDS-polyacrylamide gel, resulting peptide fragments were electrotransferred to a polyvinylidine difluoride (immobilon PVDF by Millipore) membrane. Filters were stained with 0.1% w/v Coomassie blue dye in 50% methanol for 7', destained with 50% methanol, 10% glacial acetic acid for 5', rinsed several times in water and dried. Stained peptide fragments were excised and stored in a macrophage tube at 20° C. until microsequencing was performed by direct N-terminal Edman degradation (Matsudaira, 1987).

For the cyanogen-bromide (CNBr) and o-phthaldehyde (OPA) protocol, large-scale immunoprecipitates were electrophoresed through a 3 mm thick preparative 12.5% SDS-polyacrylamide gel, electrotransferred to PVDF membrane and Coomassie dye stained, as above. p21 bands were excised, digested with CNBr at the methionine residues and sequenced. In certain samples, amino acid ends were blocked with OPA at the cycle when an amino acid proline appeared (Hulmes et al., 1989). Sequencing resumed from the single peptide fragment that contained the unblocked imino acid proline at its N-terminus.

E) PCR Amplification and Cloning

Poly(A+) RNA from RL-7 cells was prepared by standard protocol primed with oligo(dT) 15-mers and random hexamers (supplied from Pharmacia), and reverse transcribed with Moloney murine lymphotrophic virus reverse transcriptase (BRL). The generated complementary DNA (cDNA) was used in a mixed oligonucleotide polymerase chain reactions (PCR) (Gould et al., 1989). Two mixed oligonucleotide pools, containing all possible codon degeneracies, were synthesized based on the determined amino acid sequence of human 21 kD Bax. The first primer pool was a mixture of 2056 17-mers corresponding to the amino acid sequence DPVPQD. The second (antisense) primer pool was derived from amino acid sequence IGDELD and was a mixture of 2056 17-mers. A 100-ul PCR mixture contained 7890 pmol of each primer, 0.125 ug of cDNA, 2 mM of each dNTP, 10 mM Tris.HCL (pH:8.3), 50 mM KCl, 21.5 mM MgCl2, and 2.5 units of Thermus aquaticus (Tag) DNA polymerase (supplied by Perkin-Elmer/Cetus). Thirty-eight amplification cycles consisted of: denaturation, 94° C. for 2' (first cycle 4'); annealing, 60° C. 2'; extension, 72° C. 10". (last cycle 60"). PCR products were size fractionated by agarose electrophoresis and the expected 71 bp product was purified and directly ligated into a PCR cloning vector (TA cloning system by InVitrogen). Colonies containing inserts were selected and the insert sequenced with Sequenase (supplied by United States Biochemical) using primers to the T7 and SP6 regions of the plasmid vector.

F) Screening of cDNA and Genomic Libraries

Standard techniques of molecular cloning were used as described, unless indicated otherwise. Restriction enzymes were from Boehringer Mannheim Biochemicals and New England Biolabs. The 712 bp PCR cDNA (FIG. 3, bps 142–212) was radiolabeled by PCR and used to screen an Epstein-Barr virus transformed human mature B cell (Namalwa) cDNA library (Ambrus et al., 1993) in lambda-ZAP II (supplied by Stratagene) by standard hybridization and washing at 2×SSC/0.1% SDS, 50° C. Three independent positive clones were in vivo excised and sequenced. The longest of the sequenced inserts (820bp) served as a probe to further screen the Namalwa human cDNA library, a human t(17;19) ALL early B cell (UOC-B1) cDNA library in lambda-ZAP II (Inaba et al., 1992) or an oligo(T) primed, size selected murine 70Z/3 pre-β cell cDNA library in lambda gtll (Ben-Neriah, 1986). Several additional human and murine cDNA clones were obtained, subcloned, and sequenced. The final Bax sequences were determined on both strands.

For genomic screenings, a 129 SV murine genomic library in lambda FIX II (obtained from Stratagene), was screened with a full length murine Bax cDNA clone. The plaque purified genomic clones, that reacted with probes for the 5' and 3' end of the cDNA, were selected. The insert of phage clone F1, that possesses the entire 5' through 3' ends of the cDNA sequence, was subcloned into Bluescript. Exon positions were placed by restriction analysis and DNA sequencing defined the exon/intron boundaries.

G) Northern Analysis

Poly (A+) RNA from RL-7 and FL5.12 cells was prepared, electrophoresed in a denaturing 1.2% agarose-formaldehyde gel, and transferred onto a nitrocellulose membrane. Filters were hybridized with various probes, and washed by standard protocol. However, for the exon 2 specific probe, the high stringency wash was in 2×SSC/0.1 SDS at 50° C.

H) Epitope Tagging and Expression Vector Construction

An eleven amino acid tag, that contained a well characterized epitope of the influenza virus hemagglutinin (HA) protein was attached to the N-terminus of murine Baxα (HA-Baxα) by a three step PCR approach (Kolodziej and Young, 1991). In the first, second and third rounds of PCR, the ends of the Baxα ORF was stepwise extended by using 24–26 bp primers in which the N-terminus possessed the epitope and the consensus translation start site (Kozak, 1986), while the C-terminus had a stop codon. In addition, an EcoRI site was also incorporated into each primer used in the third round of amplification. The PCR mixture contained 20 pmol of each primer, 50 ng of cDNA, 2 mM of each DNTP, 10 mM Tris.HCL (pH: 8.3), 50 mM KCl, 1.5 mM MgCl2, and 2.5 units of Thermus aquaticus (Taq) DNA polymerase. Amplification of the target DNAs through 38 cycles were: denaturation, 94° C. for 1'. (first cycle 4'.); annealing, 60° C., 1'. (first cycle 52° C.); extension, 72° C., 1'. (last cycle 10') PCR products were purified and either used as template for the next round of amplification or directly ligated into a PCR cloning vector (TA cloning system by InVitrogen). The authenticity of the PCR reactions were confirmed by sequencing. The inserts were excised by EcoRI digestion, cloned into the EcoRI cloning site of SFFV-LTR-Neo expression vector (Fuhlbrigge et al, 1988) and transformed into competent XL-1 Blue cells (Strategene). Doubly CsCl purified and linearized sense-orientation plasmid constructs were transfected into FL5.12 cells by electroporation (200V, 900 mF) with a BTX 300 transfector. Cells were recovered in nonselective media for 24–48 hours, after which stably transfected cells were selected for neomycin resistance in 2 mg/ml G418 (supplied by Gibco), or for hygromycin resistance with 2 mg/ml hygromycin (supplied by Calbiochem), by plating 4–12×$10^4$ cells into 0.2 ml wells. Surviving clones were expanded and screened for the expression level of HA-Baxα and endogenous murine or transfected human Bcl-2 protein, by solubilization and immunoblotting of equal amount of total protein. High or low HA-Baxα and/or human Bcl-2 expressing clones were selected for subsequent analysis.

I) Growth Factor Deprivation Studies

To assess the effect of Baxα on cell survival, stably transfected cells were seeded at a concentration of 2×$10^5$ cells/ml in the presence of IL-3 for 24 hrs. Cells were washed thoroughly 3× in the serum free medium to remove the growth factor, and cultured at 5×$10^5$ cells/ml in triplicate. Viabilities were determined at various time points by trypan blue exclusion counting at least 100 cells from each individual culture.

EXAMPLE 1

This Example demonstrates the co-precipitation of Bcl-2 with a 21 kD protein.

Co-immunoprecipitation experiments were performed utilizing the 6C8 monoclonal antibody (moAb) that is specific for human Bcl-2, and RL-7, a human B cell line which bears the t(14;18) translocation and expresses high levels of Bcl-2. A variety of detergent conditions were tested to identify Bcl-2 associated proteins. When RL-7 cells were metabolically labeled with $^{35}$S-methionine, lysed and solubilized with 0.2% NP-40, an abundant 21 kD protein (p21) co-precipitated with Bcl-2. A lesser amount of a 24 kD species was also detected (FIG. 1).

In FIG. 1 cell lysates of ($^{35}$S)methionine-labeled RL-7 cells were immunoprecipitated with an anti human Bcl-2 moAb in the presence (+) or absence (−) of competitor cold lysate and washed as indicated above each lane. When immunoprecipitates were washed in isotonic lysis solution the association remained intact. However, the addition of 0.1% SDS to the wash eliminated p21, indicating that p21 was a non-covalently associated protein rather than a Bcl-2 degradation product.

In the presence of excess cold RL-7 cell lysate radiolabeled p21 still co-precipitated with Bcl-2 indicating that this was not a non-physiological association following cell lysis.

To confirm a specific interaction between Bcl-2 and p21, an interleukin-3 (IL-3) dependent murine cell line, FL5.12 was examined. In the absence of IL-3, FL5.12 dies by apoptosis, but overexpression of Bcl-2 extends it survival.

Figure 2:
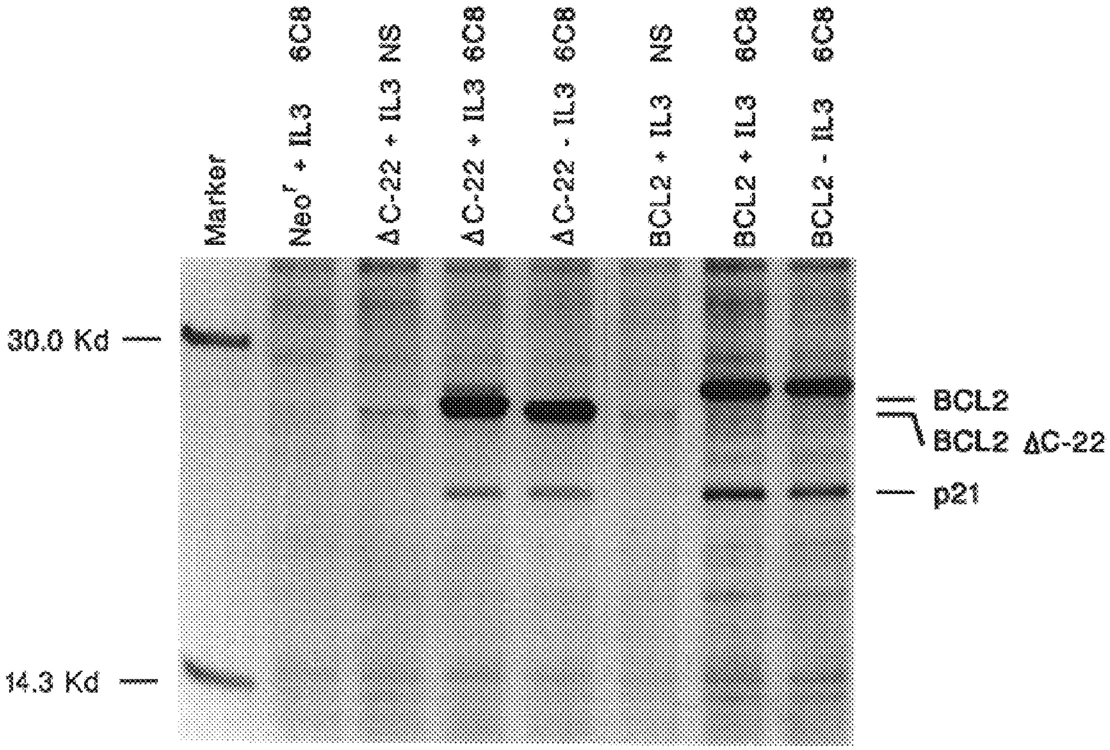
FIG. 2 shows the analysis of ($^{35}$S) Methionine-labeled immunoprecipitates using FL5.12 clones.

Stable transfectants of FL5.12 expressing wild type human Bcl-2 (FL5.12 hBcl-2) or a human Bcl-2 construct that lacks the COOH-terminal signal-anchor sequence (Δ C-22) were generated. The Bcl-2 Δ C-22 protein is no longer an integral membrane protein, yet it still provides partial protection from cell death. Immunoprecipitation of human Bcl-2 with the species specific 6C8 moAb revealed an associated murine p21 protein in FL5.12 hBcl-2 cells (FIG. 2). In FIG. 2 cell lysates of ($^{35}$S)methionine-labeled FL5.12 clones transfected with vector only (Neo$^r$), with wild type human Bcl-2 (Bcl-2), or a deletion mutant lacking the signal-anchor sequence of human Bcl-2 (Δ C-22), were immunoprecipitated with an anti-human Bcl-2 moAb (6C8) or control antibody (NS). The immunoprecipitates were analyzed by SDS-PAGE. The p21 molecule was not detected when FL5.12 cells transfected with only a Neo$^R$ vector were immunoprecipitated with 6C8. Similarly, an isotype matched control antibody, TN3 19.12 (NS) did not recognize the p21 molecule in FL5.12-hBcl-2 cells. The Δ C-22 cytosolic form of Bcl-2 also co-precipitated mouse p21 from 0.2% NP-40 lysates, even though somewhat less efficiently. These findings demonstrate the specificity and the conservation of the interaction between p21 and Bcl-2 across species. For this reason we refer to p21 as Bax (i.e; Bcl-2 Associated X protein).

EXAMPLE 2

This Example determined whether the induction of programmed cell death altered the association of Bcl-2 with Bax.

Immunoprecipitations were performed 12 hours following IL-3 withdrawal, a time point when FL5.12 cells begin to die and after which re-addition of IL-3 will not rescue cells. There was no change in the amount of Bax associated with wild type or truncated Bcl-2 following IL-3 deprivation.

EXAMPLE 3

This Example demonstrates the molecular cloning of Bax.

To determine the identity of Bax, large scale 6C8 moAb immunoprecipitates of human RL-7 and murine FL5.12-hBcl-2 cells were electrophoresed through a preparative SDS-polyacrylamide gel, and electroblotted to polyvinylidine difluoride (PVFD) membrane. The p21 (Bax) containing band was processed for microsequencing and the N-terminus proved to be blocked. Consequently internal peptide fragments were generated by V8 protease, cyanogen bromide (CNBr), or CNBr followed by O-phthaldehyde in situ digestions. Peptide fragments were sequenced by Edman degradation and 2 overlapping internal fragments provided 29 amino acids of human or murine sequences (FIG. 3).

In FIG. 3 the DNA sequence of the coding strand of human Bax and predicted amino acid sequence is shown. Only those residues of the murine protein that are divergent are shown. The heavy underlined amino acid residues correspond to the sequenced peptides of human (top) and murine (bottom) Bax. The thin underlined amino acids correspond to residues whose positions were unambiguously determined by aligning the cDNA sequence with the amino acid residues obtained from the sequencing of a mixture of peptide fragments generated by cyanogen bromide digestion. The zig-zagged line marks the predicted transmembrane domain of Bax. Exon boundaries are denoted by numbers above the cDNA sequence. Arrows indicate the origin of degenerate primers used in the mixed-oligonucleotide PCR amplification. The start of divergence between the α and β form of Bax is indicated by the *.

The sequences isolated were not identical nor homologous to known proteins and provide a basis for the cloning of the Bax cDNA. Two degenerate primers (FIG. 3, arrows) corresponding to the DPVPQD (sense) and IDGELD (antisense) amino acid regions of the sequenced human fragment were used in a mixed oligonucleotide polymerase chain reaction (PCR) with RL-7 cDNA as template. The predicted size 71 bp PCR product was subcloned, its authenticity was verified by DNA sequencing, and it was used as a probe to screen a human B cell cDNA library. An 820 bp partial cDNA clone was obtained, sequenced and used to screen additional human and murine cDNA libraries. Multiple human and murine cDNA clones were obtained, subcloned and sequenced to establish the complete amino acid sequence of Bax. To verify the authenticity of the predicted protein deduced from the cDNA sequence, the amino acid residues obtained by Edman degradation were aligned. FIG. 3 displays the human cDNA sequence and the deduced as well as direct amino acid sequence of both human and murine Bax. All sequenced amino acids were accounted for and were identical with the predicted protein sequence from the cDNAs.

The open reading frames (oRF) of both human and murine Bax are 576 bp and are 89.4% identical to one another. Both ORF encode a 192 amino acid protein with a predicted molecular weight of 21.4 kD. The methionine initiation codon of both the murine and human cDNA conforms to a Kozak consensus sequence (Kozak, 1986). The murine and human Bax proteins are highly conserved being 96% homologous with only six conservative and eight non-conservative amino acid changes, mostly in the N-terminal half. Both proteins have seven Ser/Thr residues that may represent sites of phosphorylation. Hydropathicity analysis (Eisenberg et al., 1984) predicts the presence of a C-terminal transmembrane domain suggesting that Bax exists as an integral membrane protein.

EXAMPLE 4

This Example demonstrates the genomic organization of the Bax gene.

Murine genomic clones were isolated by screening a genomic phage library with a murine Bax cDNA probe. Clones were plaque purified and characterized by restriction analysis. The location of exons and the exon-intron boundaries were determined by S restriction enzyme analysis and genomic sequencing. The direction of the transcription is from left to right.

Phage clone F1 contained a 16 kb genomic insert possessing the entire 5' through 3' ends of the cDNA sequence. The exon-intron boundaries were sequenced with primers derived from the cDNA and in all cases were in agreement with consensus exon/intron splice sequence requirements. The Bax gene consists of six exons all within a 4.5 kb region. Protein encoding information is contributed by all six exons.

EXAMPLE 5

This Example demonstrates the alternative transcripts and tissue distribution of the Bax gene.

The 70-Z/3 murine pre-B cell cDNA library consistently yielded clones of a single Bax species whose sequence is shown in FIG. 3. However, a Namalwa human mature B cell and a t(17/19) early B leukemia cell (UOC-B1) cDNA library also yielded several clones that diverged from the sequence depicted in FIG. 3. These libraries possessed three species of Bax cDNAs shown in FIG. 4.

In FIG. 4, the boxes indicate exons identified by numbers. The shading difference between exon 3 for its RNA versus protein product in Bax γ indicates a frameshift in exon 3 due to the alternative splicing of exon 2. The ~1.0 kb αRNA encodes the 192 amino acid 21 kD protein with the predicted transmembrane segment A ~1.5 kb βRNA encodes a 218 amino acid 24 kD protein that lacks a hydrophobic terminus and may be a cytosolic form. The βRNA possesses an unspliced intron 5 of 630 bp accounting for the apparent size increment from 1.0 to 1.5 kb (FIG. 4 and FIG. 5). In FIG. 5 the DNA sequence and predicted amino acid sequence code of the Baxβ form starting at the exon 5-intron 5 border. Intron 5 contributes 60 amino acids before encountering a stop codon and lacks a transmembrane domain. The multiple cDNAs which represent the γ form of RNA lack the small 53 bp exon 2 (FIG. 4). Both 1.0 kb and 1.5 kb forms of the γ RNA species were noted and are distinguished by the alternative splicing of intron 5 (FIG. 4). The elimination of exon 2 shifts the reading frame in exon 3 which would contribute 30 novel amino acids before encountering a stop codon (FIG. 6) In FIG. 6, the DNA sequence and predicted amino acid sequence of the Bax γ form is shown. If translated the γ RNAs would predict a protein of only 41 amino acids with a molecular weight of 4.5 kd (FIG. 4).

To test if the predicted Bax species existed as mature mRNAs within cells, Northern blot analysis of poly (A+) RNA from FL5.12 and RL-7 was performed. An exon 1,3,4,5,6 containing cDNA probe identified a single 1.0 kb RNA species in FL5.212 but a 1.0 and 1.5 kb RNA within RL-7. Both the 1.0 and 1.5 kb RNAs were detected by an exon 6 specific probe, only the 1.5 kb RNA was identified. An exon 2 specific probe appeared to hybridize more strongly to the RNAs of the IL-3 dependent FL5.12 cell than the immortalized RL-7 cell line. Thus, evidence exists by Northern and cDNA analysis for the existence of alternatively spliced α, β, and γ RNA species that predict 3 types of proteins. FL5.12 cells possess the 1.0 kb α RNA, and demonstrated only the p21 molecule in association with Bcl-2 (FIG. 2). Of potential relationship, RL-7 revealed both a 1.0 kb αand 1.5 kb β RNA and displayed both a p21 and p24 molecule associated with Bcl-2 (FIG. 1). It further appears that the Bcl-2 associated p24 molecule in RL-7 is the product of the 1.5 kb Bax β RNA.

Northern analysis of total RNA from a survey of organs indicated that Bax was not lymphoid restricted but was widely expressed in a variety of tissues. Many tissues including lung, stomach, kidney and spleen expressed both 1.0 and 1.5 kb RNA species. The 1.0 kb RNA was somewhat preferential in heart and smooth muscle, whereas the duodenum revealed principally the 1.5 kb RNA. The 1.0 kb RNA was most abundant in the pancreas, while liver did not express substantial amounts of the gene. curiously the brain apparently possesses the 1.5 kb RNA and a higher molecular weight species. Northern analysis indicates a wide expression of Bax and a splicing pattern that varies between lineages and cell types.

EXAMPLE 6

This Example demonstrates that the Bax protein is homologous to Bcl-2.

The GenBank database when searched with the BLAST and TFASTA algorithms revealed a 20.8% identity and 43.2% similarity between p21 Bax and Bcl-2 (FIG. 7). The alignment was maximized by introducing insertions marked by minuses. Identity across all 4 proteins is denoted in black shading, conservative changes are stippled, and the exon boundaries are numbered. The two most conserved regions, domain I and domain II, are boxed. While some homology exists throughout the molecules the regions corresponding to exon 4 and 5 of Bax are the most conserved. The most highly conserved areas between Bcl-2 and Bax are denoted in FIG. 7 as domain I and domain II. Domain I is located on Bax exon 4, domain II on exon 5 and the putative transmembrane domain on exon 6. The juncture of Bax exon 5/6 at the end of domain II is identical to the location of the exon 2/3 juncture for Bcl-2. Of interest the retention of intron 5 at this site results in the β form of Bax RNA that lacks a transmembrane domain. Similarly, a β RNA form of Bcl-2 has been observed that lacks exon 3 and terminates in intron 2 predicting a β protein that would lack the signal-anchor segment.

EXAMPLE 7

This Example demonstrates that overexpressed Bax α accelerates programmed cell death.

The homology and physical association between Bax and Bcl-2 suggested that Bax might also modulate programmed cell death. Consequently, we overexpressed Bax within FL5.12 cells which normally die by apoptosis following withdrawal of IL-3. To follow the protein level of transfected Bax, an 11 amino acid tag containing a well characterized epitope of the influenza virus hemagglutinin (HA) protein was added to the N-terminus of murine Baxα by the PCR approach. This HA-Baxα insert was subcloned into an expression construct utilizing the SFFV LTR as a constitutively expressed promoter. FL5.12 cells were electroporated and G418 resistant stable clones were selected by limiting dilution. Clones were assessed for levels of endogenous murine Bcl-2 with the 3F11 moAb specific for mouse Bcl-2 and for Bax with the 12CA5 moAb specific for the HA epitope tag (FIG. 8B, C.).

A series of high and low Bax expressing clones were placed into IL-3 deficient media and cell survival was monitored by vital dye exclusion. Neither overexpression of wild type Baxα or HA-Baxα has ever conferred a survival advantage in the numerous clones that have been assessed. Instead, the presence of high levels of Bax have consistently accelerated the rate of cell death FIG. 8A.

Figure 8A:
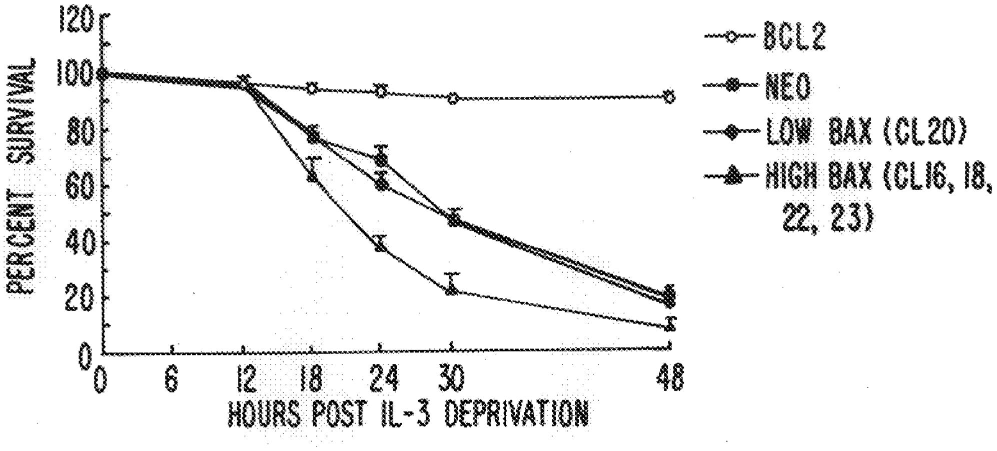
FIG. 8 demonstrates that overexpressed Bax accelerates cell death.

In FIG. 8A viability assays were performed. Triplicate cultures of FL5.12 control cells ($Neo^r$), human Bcl-2 transfected (Bcl-2), and several independent clones constitutively expressing HA-Baxα were deprived of IL-3. The percent viability was assessed by trypan blue exclusion as 12, 18, 24, 30, and 48 hrs following IL-3 deprivation and plotted as the mean±standard error.

Figure 8B:
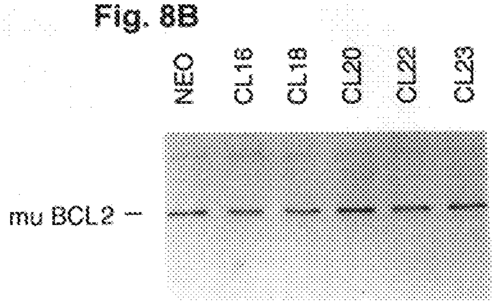
Figure 8C:
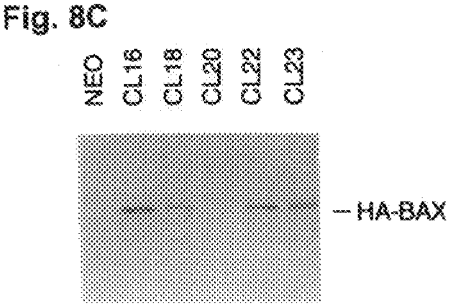

In FIGS. 8B and C, Western blot analysis of endogenous murine Bcl-2 (B) or HA-Baxα (C) protein in FL5.12 control cells (Neo) and HA-Baxα (cl.#) transfected FL5.12 clones. The murine Bcl-2 specific moAb 3F11 (B), or the hemagglutinin epitope tag specific moAb 12CA5 (C) was used. HA-Baxα stably transfected clones 16, 18, 20, 22, and 23 and FL5.12 cells transfected with a control vector lacking the Bax insert ($Neo^R$) possessed comparable levels of endogenous murine Bcl-2 (FIG. 8B). Levels of Baxα protein varied between very low (CL20), to high (CLs 16, 18, 22, 23) (FIG. 8c). As shown in FIG. 8 a Cl 20 deviates only minimally from the $Neo^R$ control cell line at 24–48 hours post IL-3 deprivation. However, high expressing CLs 16, 18, 22, and 23 display accelerated cell death at 18–30 hrs and are nearly all dead at 48 hours compared to the 18% viability of the $Neo^R$ line.

EXAMPLE 8

The Example demonstrates that the ratio of Bcl-2 to Bax affects the rate of programmed cell death.

To investigate the inter-relationship between levels of Bcl-2 and Bax we overexpressed Bcl-2 in two cell lines with high levels of HA-Baxα. Clones 16 and 23 of the established HA-BAXα clones were co-transfected with a SFFV-hBcl-2 vector and an expression vector (LAP 267) providing a hygromycin selection marker. Hygromycin resistant clones were selected and assessed for the expression of hBcl-2 with the 6C8 moAb and for levels of HA-Baxα with the 12CA5 moAb (FIG. 9B, C).

Figure 9A:
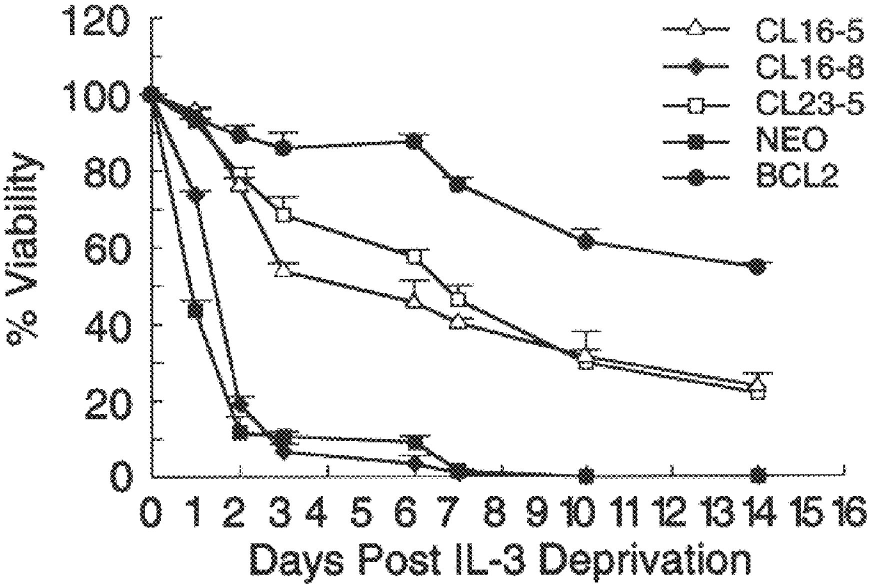
FIG. 9 demonstrates that the ratio of Bcl-2 and Bax affects the viability of IL-3 deprived FL5.12 cells.
Figure 9B:
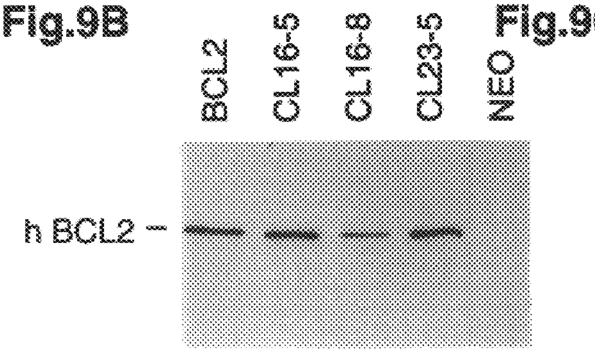
Figure 9C:
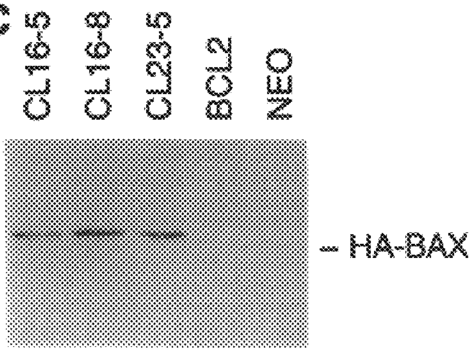

In FIG. 9A, viability assays were performed with triplicate cultures of FL5.12 control cells ($Neo^r$), human Bcl-2 transfected (Bcl-2), and three independent FL5.12 cells constitutively expressing both HA-Baxα and human Bcl-2 (Cls 16-8, 16-5, 23-5) were deprived of IL-3. The percent viability was assessed by trypan blue exclusion at several timepoints and plotted as the mean±standard error. FIG. 9B, C show Western blot analysis of transfected human Bcl-2 (B) and HA-Baxα (C) protein in FL5.12 control cells (Neo), human Bcl-2 transfected (Bcl-2), and three independent FL5.12 cells contitutively expressing both HA-Baxα and human Bcl-2 (CLs 16-5, 16-8, 23-5). The human Bcl-2 specific moAb 6C8 (B) or the hemagglutinin epitope tag specific moAb 12CA5 was used.

Clone 16-5 and 23-5 expressing high levels of hBcl-2 and Clone 16-8 expressing intermediate amounts of hBcl-2 were selected for further study. Densitometry estimates of the relative amounts of the two proteins within these cells revealed a relative ratio of hBcl-2/HA-Baxα of 2.04 for CL 16-5, 1.65 for CL 23-5, and 0.55 for Clone 16-8. The time course of apoptotic death following IL-3 deprivation was compared in these clones and in FL5.12 cells possessing only $Neo^R$ control vector or only hbcl-2 (FIG. 9A). The addition of hBcl-2 partially countered the Bax accelerated cell death. In multiple experiments the rate of cell death paralleled the ratios of hBcl-2/HA-Baxα. Clones 16-5 and 23-5 of the double transfected clones demonstrated no death at 24 hrs whereas the $Neo^R$ control line was only 43% viable by this time. Clone 16-8 with the lowest hBcl-2/HA-Baxα ratio was 73% viable at 24 hours but lost all viability by day 7. Clones 16-5 and 23-5 with high hBcl-2/HA-Baxα ratios possessed viable cells over two weeks following IL-3 deprivation. Despite comparable levels of Bcl-2, Clone 16-5 and Clone 23-5 never approached the viability observed for the clone which only expressed hBcl-2 (FIG. 9*a*). Thus the presence of Bax also counters the death-repressor activity of Bcl-2.

EXAMPLE 9

This Example demonstrates that Bax forms homodimers and heterodimerizes with Bcl-2.

The shared homology and reciprocal relationship between Bcl-2, Bax and cell survival prompted a further examination of their in vivo association. When HA-Baxα single transfected cells were immuno-precipitated with the HA tag specific 12CA5 moAb, a substantial amount of endogenous p21 Bax was co-precipitated (lane 5, FIG. 10A). Cell lysates of ($^{35}$S)methionine-labeled FL5.12 clones transfected with human Bcl-2 (Bcl-2), with HA tagged murine Bax (Bax), or with both human Bcl-2 and HA tagged Bax (B+B), were immunoprecipitated with an anti human Bcl-2 moAb (6C8), with an HA specific moAb (12CA5), or with a murine Bcl-2 specific moAb (3F11). Immunoprecipitated proteins were resolved by SDS-PAGE. In FIG. 11 Western Blot analysis was performed of primary immunoprecipitates for murine Bcl-2 with a biotinylated 3F11 moAb (left) or for transfected human Bcl-2 with the 6C8 moAb (right). FL5.12 control cells ($Neo^r$) or clones transfected with HA BAXα (Bax) or human Bcl-2 plus HA-Baxα (B+B) were immunoprecipitated with the murine Bcl-2 specific moAb (3F11), the HA specific moAb (12CA5), or with a human Bcl-2 specific moAb (124).

Figure 10:
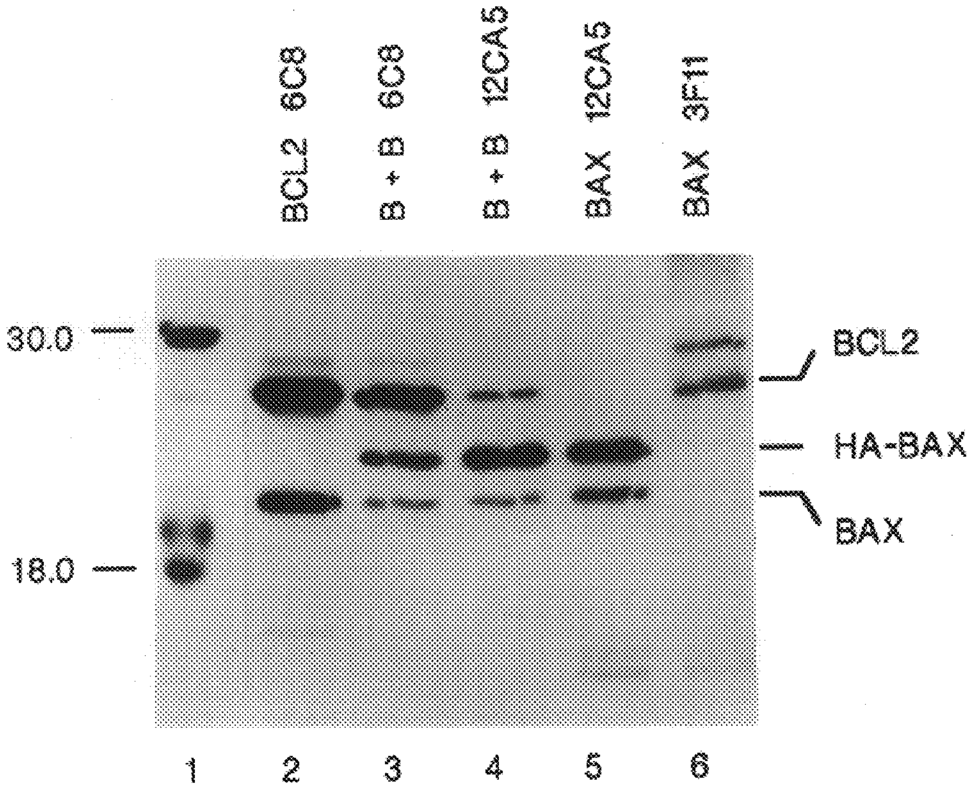
FIG. 10 demonstrates that Bax homodimerizes and forms heterodimers with Bcl-2.
Figure 11:
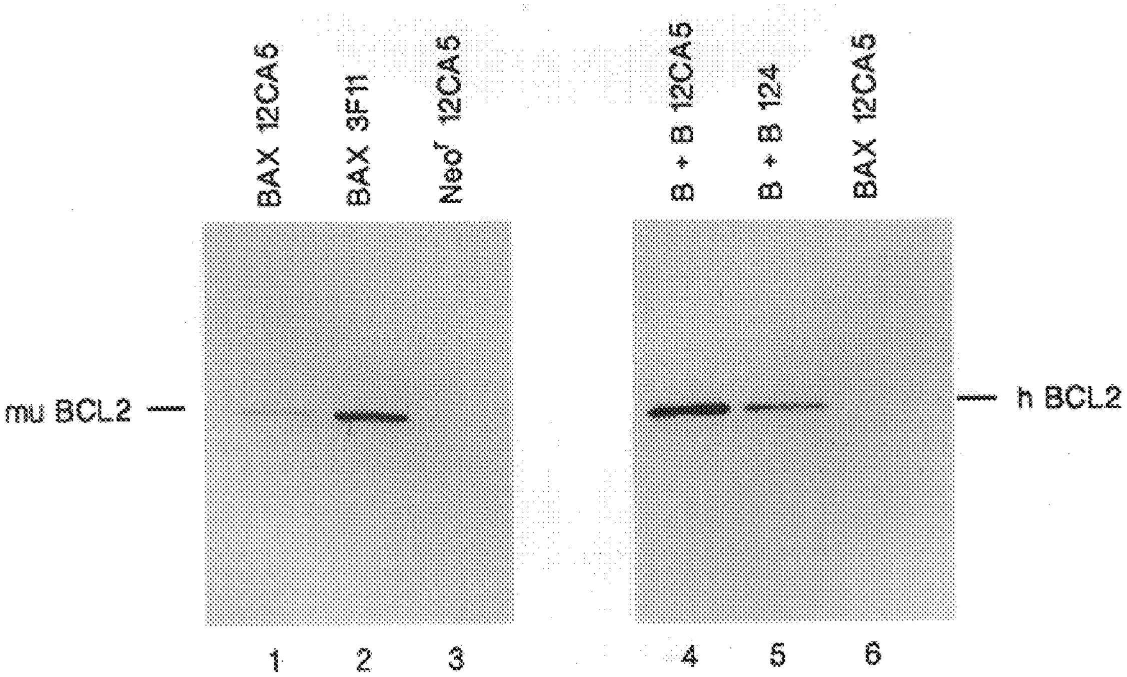
FIG. 11 shows western blot analysis of heterodimers.
Figure 12:
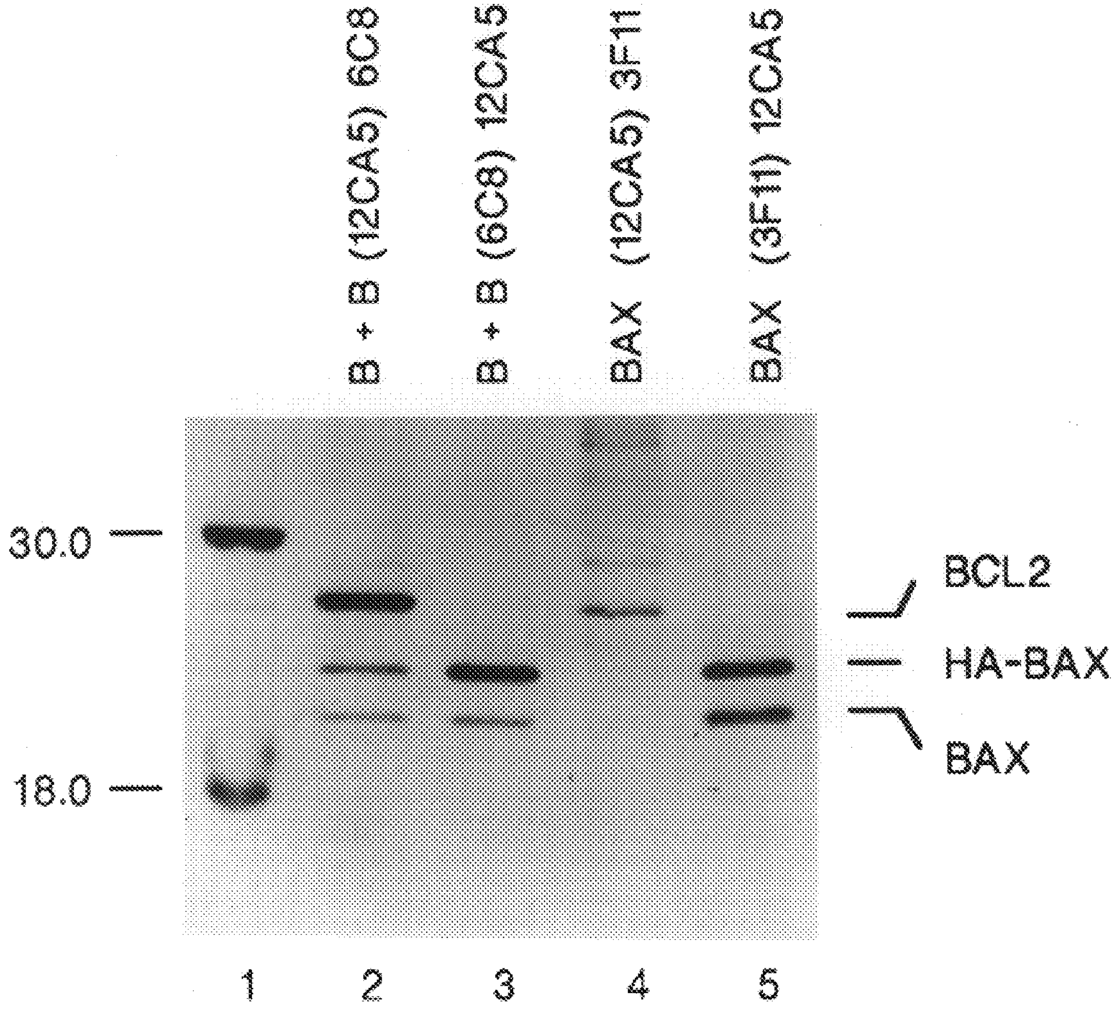
FIG. 12 shows immunoprecipitations of supernatants.

In FIG. 12 secondary immunoprecipitations of the supernatants from the precipitates in FIG. 10 were performed. Designations are identical to FIG. 10. MoAbs used in the primary immunoprecipitations are shown in parenthesis. MoAbs used in the secondary immunoprecipitation followed. Immunoprecipitated proteins were revolved by SDS-PAGE.

In addition a very small amount of endogenous murine Bcl-2 was also precipitated with HA-Baxα. Western blots of the 12CA5 moAb precipitates confirmed the identity of murine Bcl-2 (lane 1, FIG. 11). Immunoprecipitation of that remaining supernatant with the murine Bcl-2 specific 3F11 moAb revealed that the majority of endogenous Bcl-2 did not associate with Bax (lane 4, FIG. 12). This finding was confirmed by performing the experiments in the reverse order. Most of the murine Bcl-2 in a primary immunoprecipitate with the 3F11 moAb was not complexed with HA-Baxα or endogenous Bax (lane 6, FIG. 10). Yet, a secondary immunoprecipitation of that remaining supernatant with the 12CA5 moAb revealed the majority of HA-Baxα was complexed with the endogenous Bax protein (lane 5, FIG. 12). Immunoblots developed with a biotinylated 3F11 moAb confirmed that the amount of endogenous murine Bcl-2 associated with HA-Baxα was small compared to the total murine Bcl-2 (lanes 1, 2 FIG. 11).

However, high levels of Bcl-2 protein introduced by a Bcl-2 expression construct changed the ratio of Bcl-2/Bax heterodimers vs. Bax homodimers. When double transfected cells were immunoprecipitated with 6C8 moAb both epitope tagged and endogenous Bax complexed with the overexpressed hBcl-2 (lane 3, FIG. 10). A secondary immunoprecipitation of that remaining supernatant with the 12CA5 moAb revealed that some of the Bax was not complexed with Bcl-2 and formed homodimers instead (lane 3, FIG. 12). In reciprocal experiments, 12CA5 moAb immunoprecipitates also contained hbcl-2 (lane 4, FIG. 10). Substantial amounts of hBcl-2 appeared to be independent of Bax (compare lanes 3,4, FIG. 10). However, immunoprecipitation with 12CA5 was not complete in that the remaining supernatant when immunoprecipitated with the 6C8 moAb revealed endogenous Bax and HA-Baxα in association with Bcl-2 (lane 2, FIG. 12). Yet, the intensity of the bands argued that a portion of hBcl-2 was independent of Bax molecules (lane 2, FIG. 12). Immunoblots confirmed that substantial amounts of hBcl-2 were in the primary immunoprecipitates of HA-Baxα (lane 4, FIG. 11).

Figure 13:
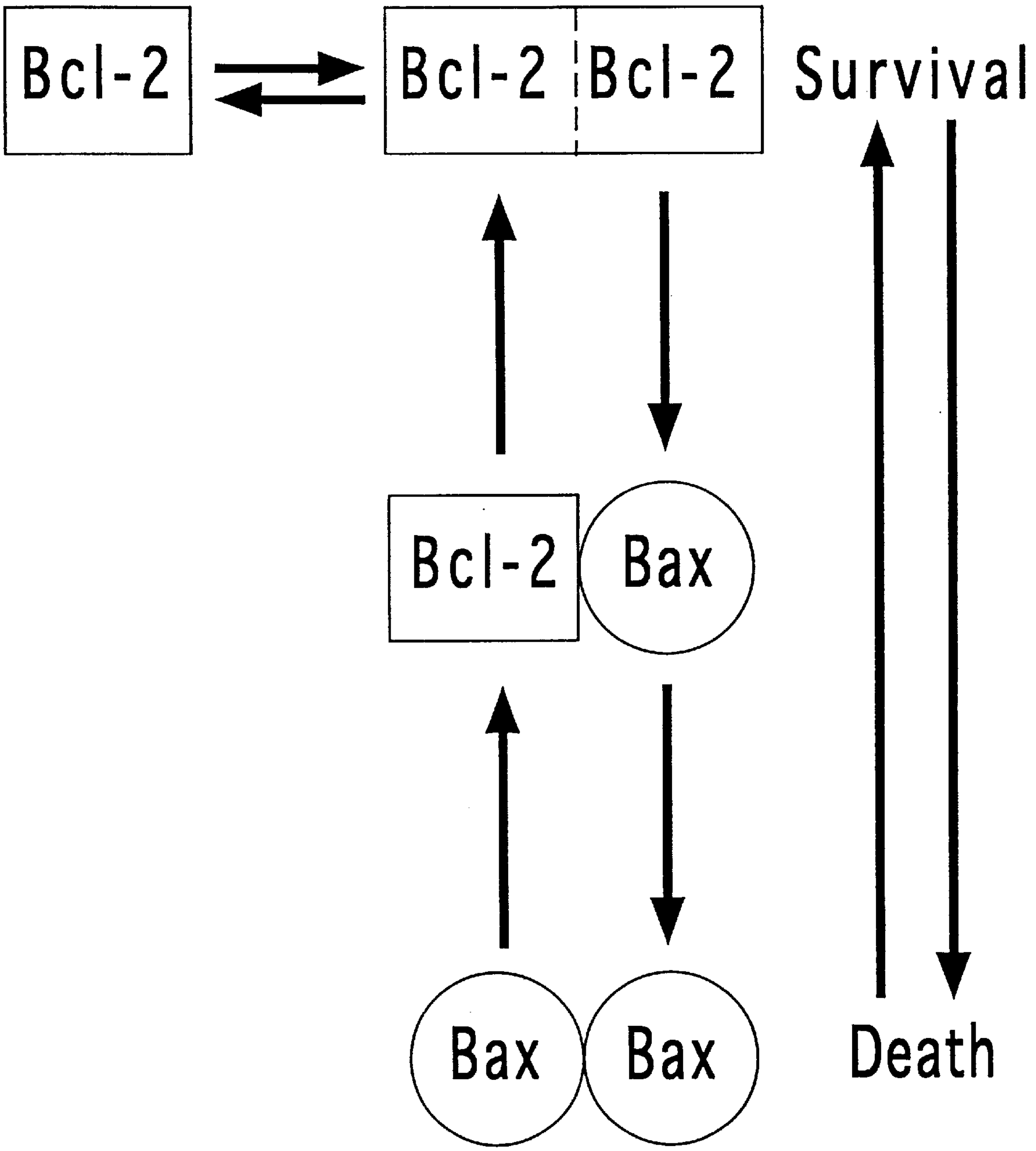
FIG. 13 demonstrates the interrelationship between Bcl-2 and Bax and the regulation of programmed cell death.

These studies establish that Bax homodimerizes and that the overexpression of Bcl-2 competes for Bax by heterodimerization (lanes 2,3,4, FIG. 10). This is also depicted in FIG. 13 wherein all indicated protein associations may represent dimers or higher oligomers. Free Bcl-2 is drawn alternatively as monomer or homodimer since some homodimerization of Bcl-2 has been noted.

The site-specific mutagenesis work of Bcl-2 and its implications for protein-protein interaction and definitively regulating a decisional step in the commitment to death has also been unexpectedly discovered. This is more particularly described in the following figures.

FIG. 14, the cloning of the Bax cDNA established a family of Bcl-2 closely related genes which were most highly conserved within segments known as domain I (SEQ ID NOS:12–16) and domain II (SEQ ID NOS:17–21). Domain I of human Bcl-2 is represented by SEQ ID NO:12, of human Bax by SEQ ID NO:13, of mouse MCL1 by SEQ ID NO:14, of African Swine Fever Virus ("ASFV") LMW5-HL by SEQ ID NO:15 and of Epstein Barr Virus ("EBV") BHRF-1 by SEQ ID NO:16. Domain II of human Bcl-2 is represented by SEQ ID NO:17, of human Bax by SEQ ID NO:18, of mouse MCL1 by SEQ ID NO:19, of ASFV LMW5-HL by SEQ ID NO:20 and of EBV BHRF-1 by SEQ ID NO:21. It is now clear that this is an even wider family of molecules that includes Bcl-x, MCL-1 and two DNA virus proteins, LMW5-HL as well as BHRF-1 of the Epstein Barr virus. As can be seen the homoliges within these sets of proteins are focused within domain I and II.

Particularly dramatic is the middle segment of domain I of FIG. 7, NWGR which is conserved all the way to the Epstein Barr virus protein retaining the GR motif. The demonstration of the capacity of Bax and Bcl-2 to interact both in vivo and in vitro strongly indicates that these other Bcl-2 related proteins will also be involved in homodimerization and heterodimerization with different members of this family. Thus, all manipulations of domain I and domain II which are shown to affect the Bcl-2/Bax interaction and physiologic functions are equally applicable to all the family members denoted.

FIG. 14B detailed the point mutations throughout the domain I and Bcl-2 that were utilized (SEQ ID NOS:21–26).

FIG. 14C denotes the tested mutations through the conserved domain II (SEQ ID NOS:27–31) of FIG. 7.

Figure 15A:
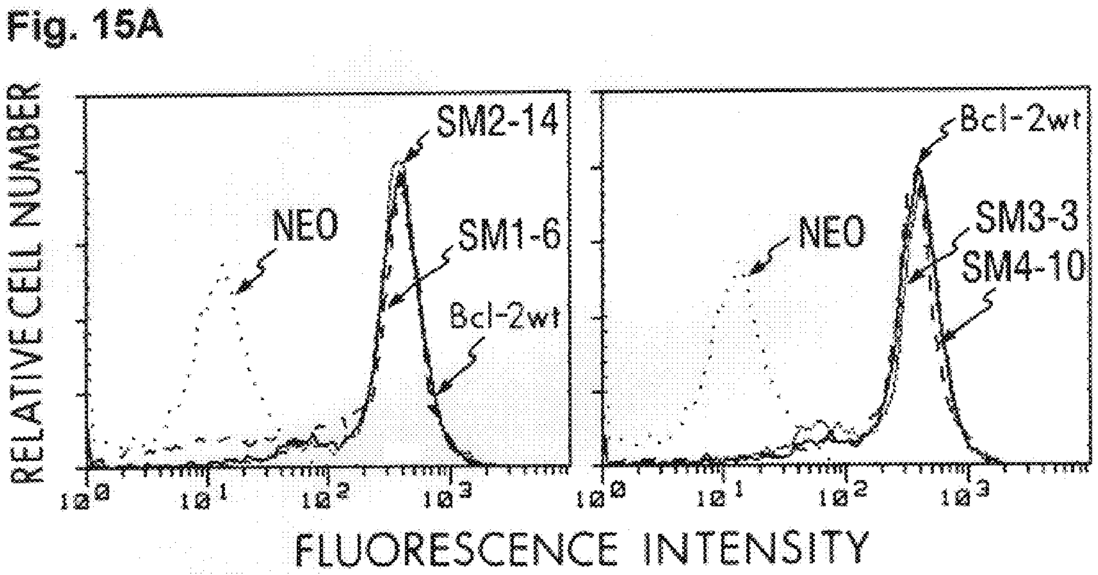
FIG. 15 shows an analysis of the level of mutant Bcl-2 protein in two cell lines (FL5.12 and 2B4).
Figure 15B:
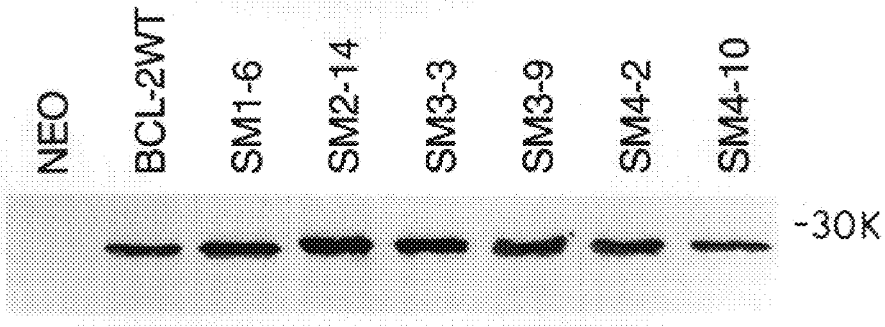
Figure 15C:
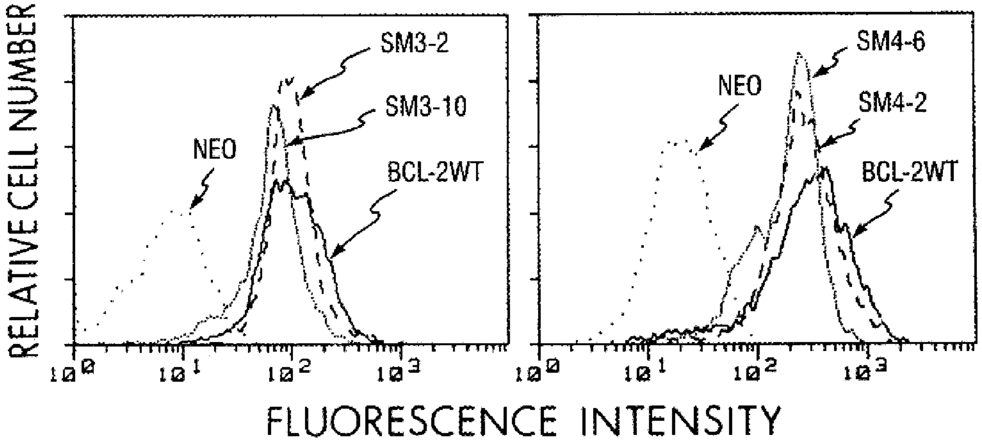
Figure 15D:
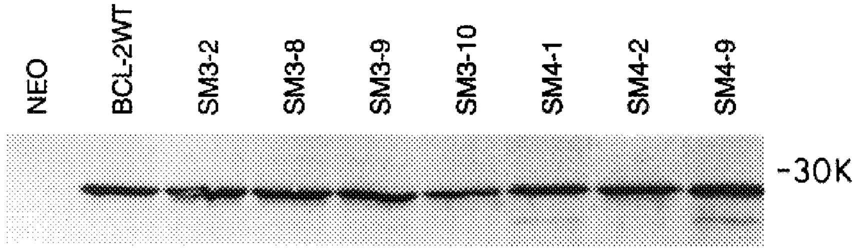

FIG. 15A is an analysis of the level of Bcl-2 protein expression in the IL-3 dependent FL5.12 cell line that has been stably transfected with Bcl-2 protein intracellularly as determined by flow cytometry. As indicated the levels of the mutation products are comparable to that of the wild-type Bcl-2 clones. FIG. 15 is a Western blot of the same stable transfectants of FL5.12 that confirm comparable levels of steady state protein. FIG. 15C is a parallel analysis of stable transfectants bearing these expression constructs in the 2B4 T cell hybridoma that is sensitive to dexamethasone as well as gamma irradiation induced death. Once again these reagents bear comparable levels of steady state Bcl-2 protein. This figure establishes that any physiologic differences in function that these molecules have is inherent to the altered point mutations and not to quantitative levels of Bcl-2 protein.

Figure 16A:
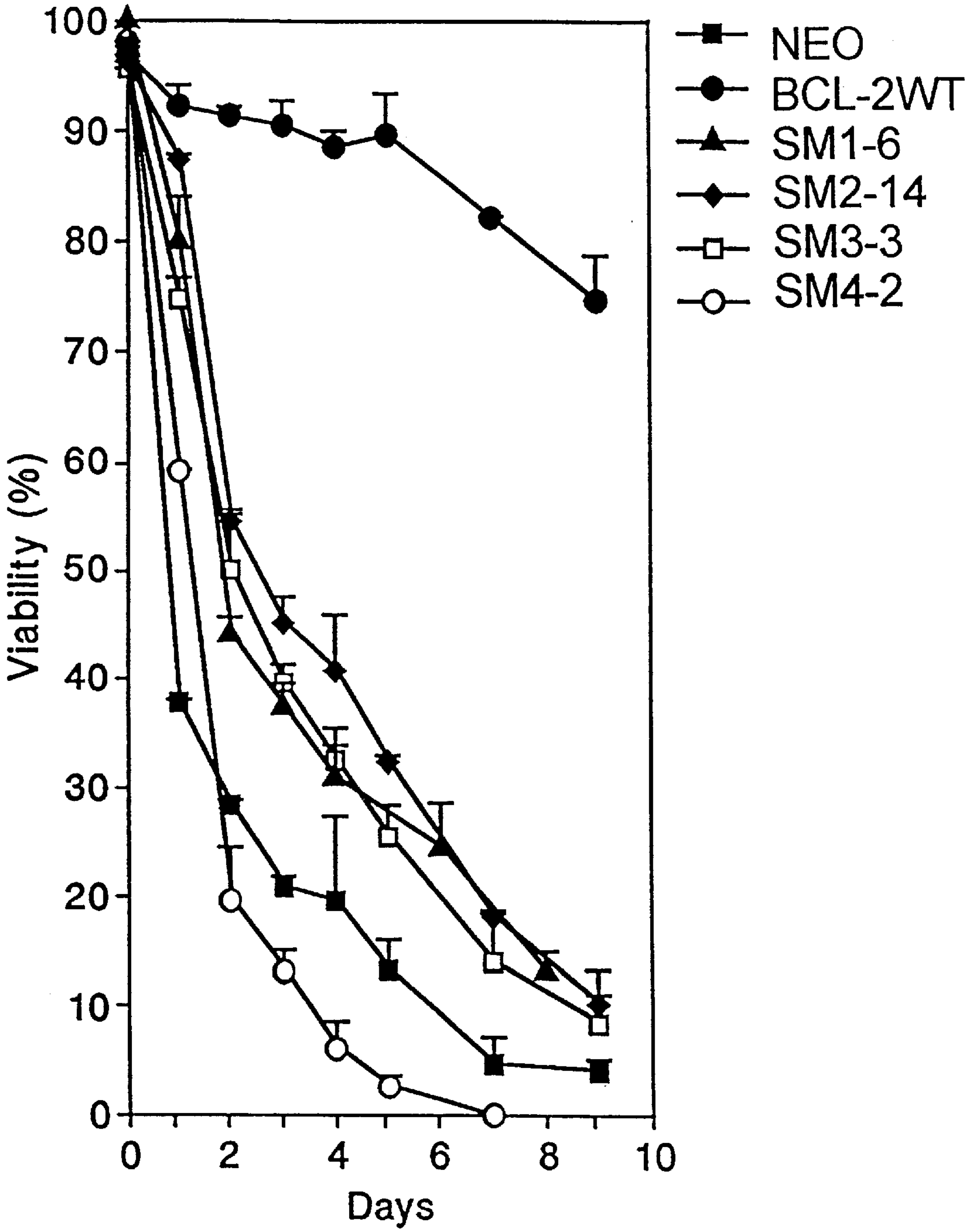
FIG. 16 shows an Il-3 deprivation time course of stable cell transfects and DNA Fragmentation assay (FL5.12).

FIG. 16 is an IL-3 deprivation time course of the stable transfects of FL5.12. It demonstrates that wild-type Bcl-2 saves FL5.12 cells from programmed cell death when compared to a control that has received a neomycin resistance expression vector only. Importantly, mutations in domain I that eliminate either the FRDG sequence or the WGR sequence essentially eliminate the capacity of the Bcl-2 product to repress death. The rate of death returns to the same time course of the Neo control clone. Also noted is that a single amino acid alteration through the WGR sequence with a substitution of either an alanine in mI-3 or a glutamic acid within mI-4 for the glycine in the WGR sequence completely eliminates the capacity of Bcl-2 to repress cell death. In fact those clones show an acceleration of death compared to the control. As we will discuss later this provides evidence that Bcl-2 may be interacting with other proteins beyond Bax.

Figure 16B:
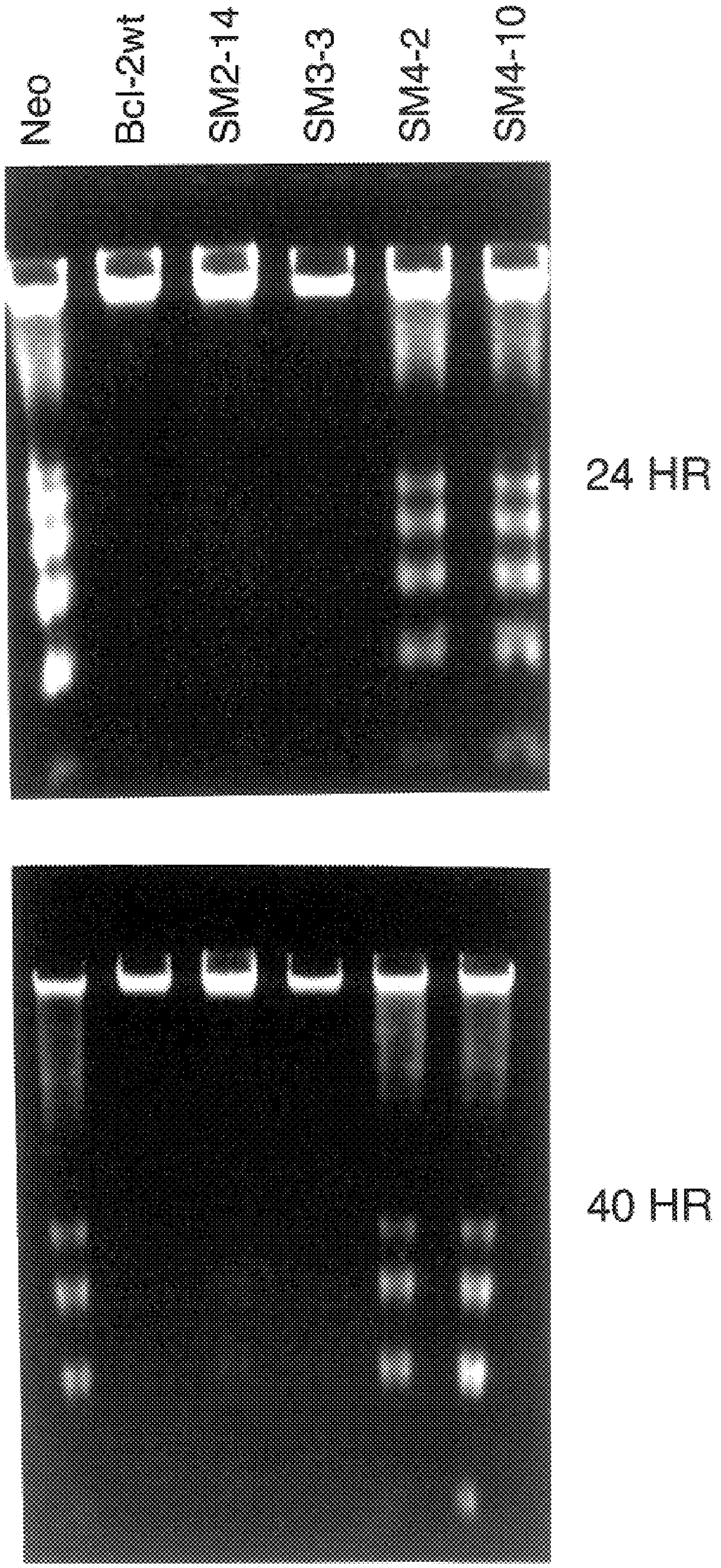
Figure 16C:
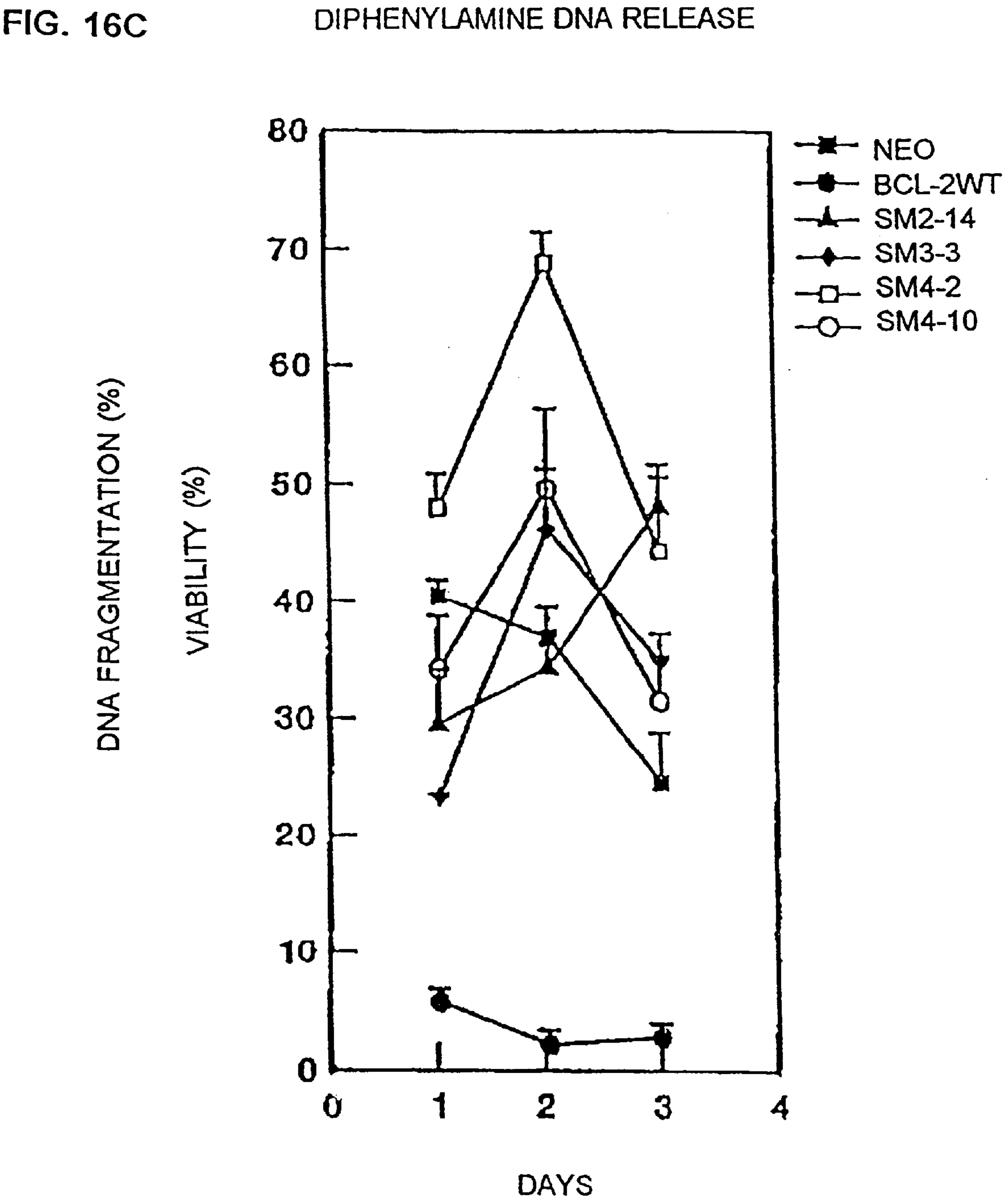

FIG. 16B establishes that this death is an apoptotic programmed cell death in which a nucleosomal length DNA degradation pattern is seen. In FIG. 16C a more quantitative measurement of this is provided looking at per cent of DNA fragmentation as a measurement of released DNA by a diphenylamine assay. This shows that the clones which express the mutant Bcl-2 degrade and release their DNA in comparison to the wild-type Bcl-2. This essentially establishes the death pattern as being apoptosis.

Figure 17A:
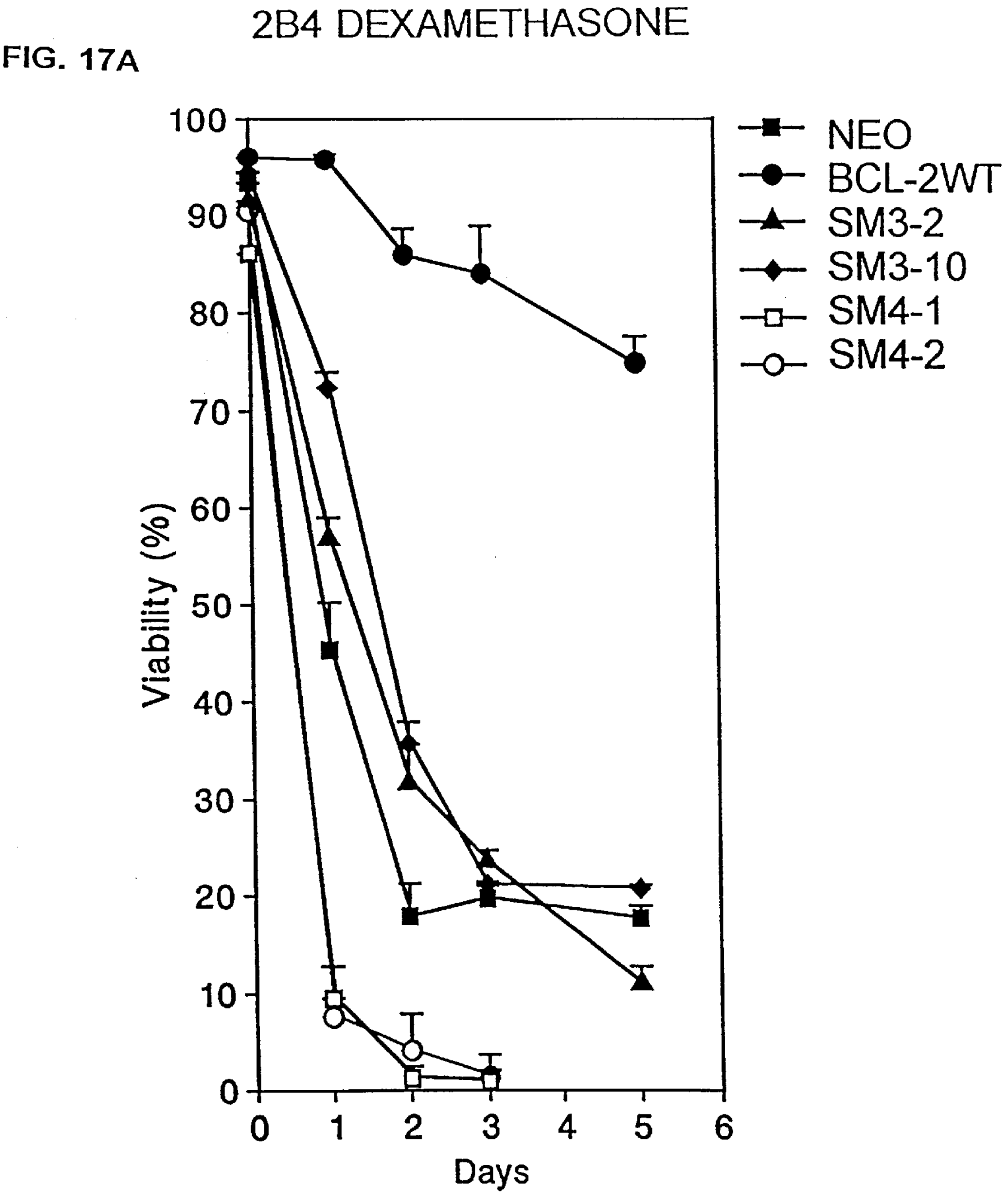
FIG. 17 shows two viability studies of cell lines (2B4).
Figure 17B:
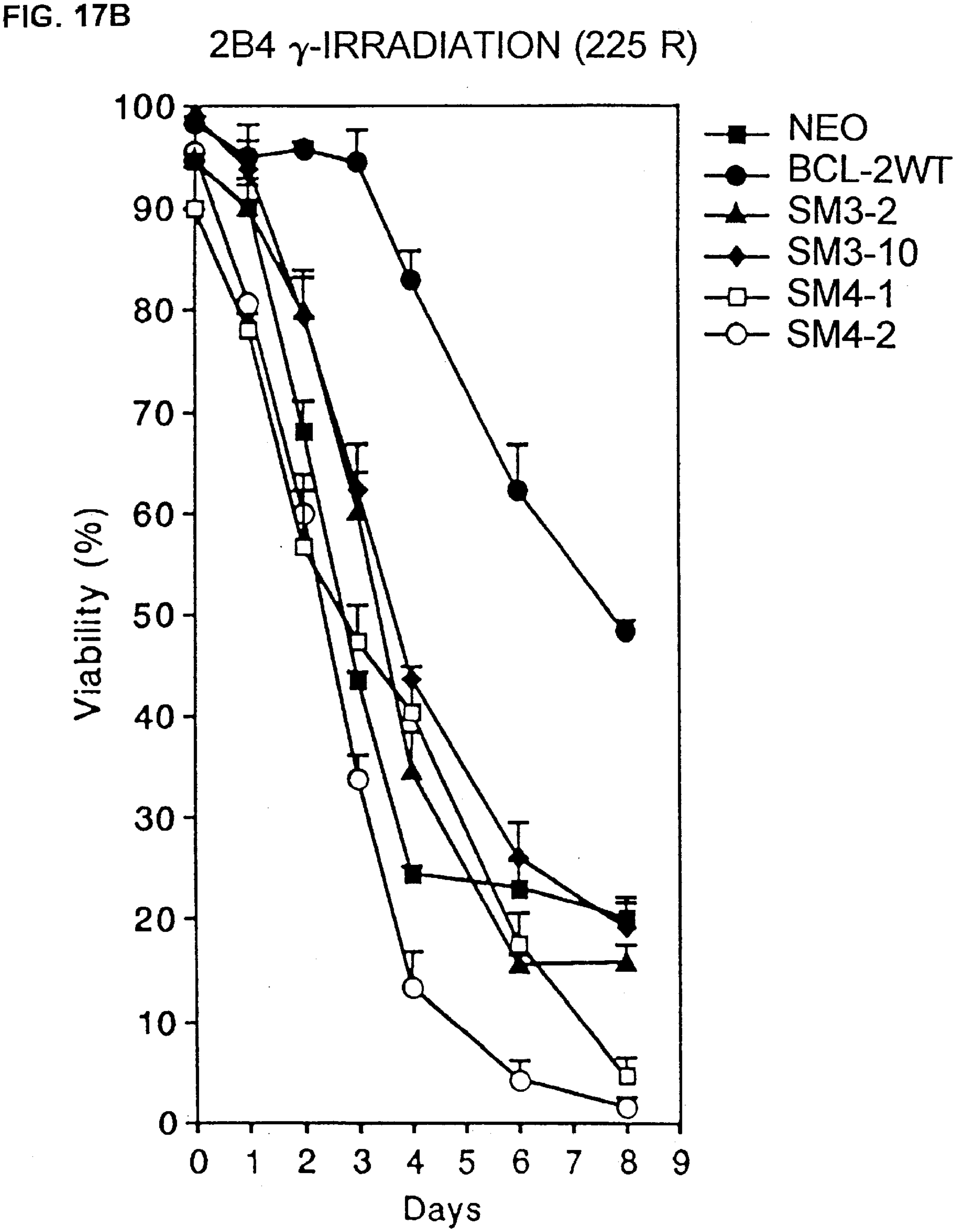

FIG. 17 shows a parallel study of viability in which the 2B4 T cell hybridoma bears either wild-type Bcl-2 or the WAR or WER mutant within domain I. Bcl-2 wild-type confers resistance to either glucocorticoid or gamma irradiation induced programmed cell death. The presence of mutations SM3 and SM4 eliminates Bcl-2's death repressor activity in these signal transduction pathways of apoptosis as well. Once again the WER mutation shows an accelerated rate of cell death compared to the neomycin resistance containing control.

Figure 18A:
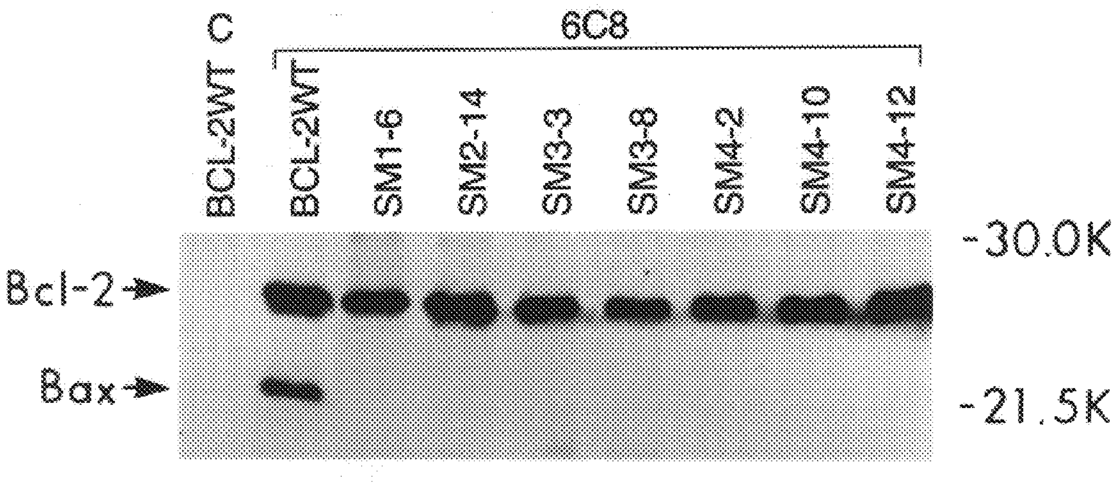
FIG. 18 shows immunoprecipitations of radiolabeled transfectants.
Figure 18B:
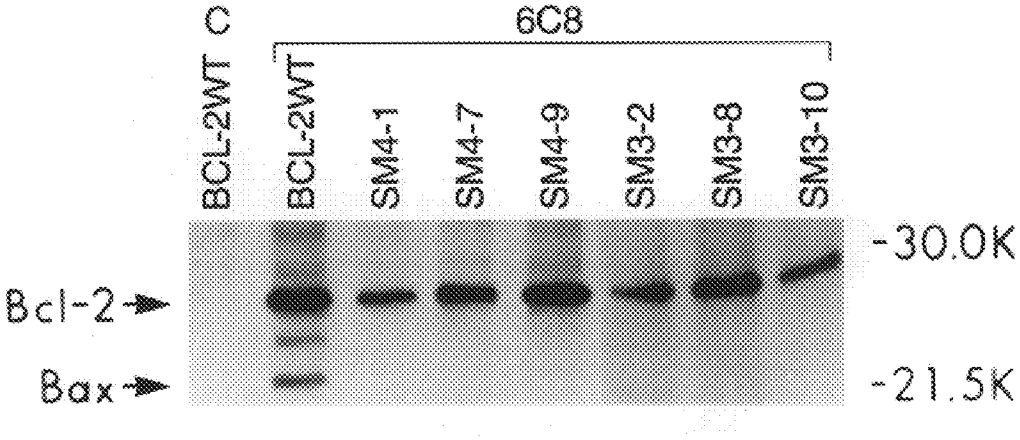

FIG. 18 shows immunoprecipitations of radiolabeled FL5.12 stable transfectants in A and 2B4 stable transfectants in B. Immunoprecipitation of wild-type Bcl-2 always shows associated Bax and at times the p24 molecule. However, all of the mutations which disrupt the capacity for Bcl-2 to block death also disrupt its ability to recognize Bax.

Figures 19A, 19B, 19C, 19D:
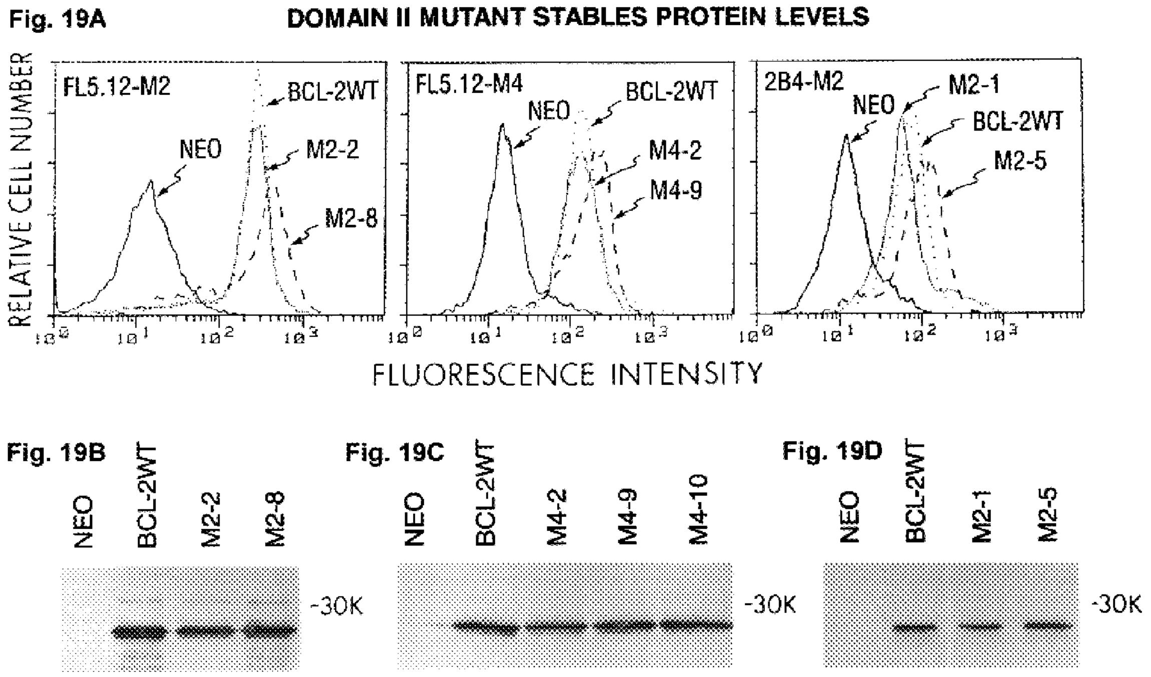
FIG. 19 demonstrates a parallel assessment of stable transfectants of domain II Bcl-2 mutants.

FIG. 19 is a parallel assessment of stable transfectants of FL5.12 and 2B4 cells with the mutations through domain II. The flow cytometry examination of Bcl-2 protein levels indicate a comparable quantity of the mutant as compared to wild-type Bcl-2 in these stable clones. Panels 19B, C and D confirm that at a Western blot level.

Figure 20A:
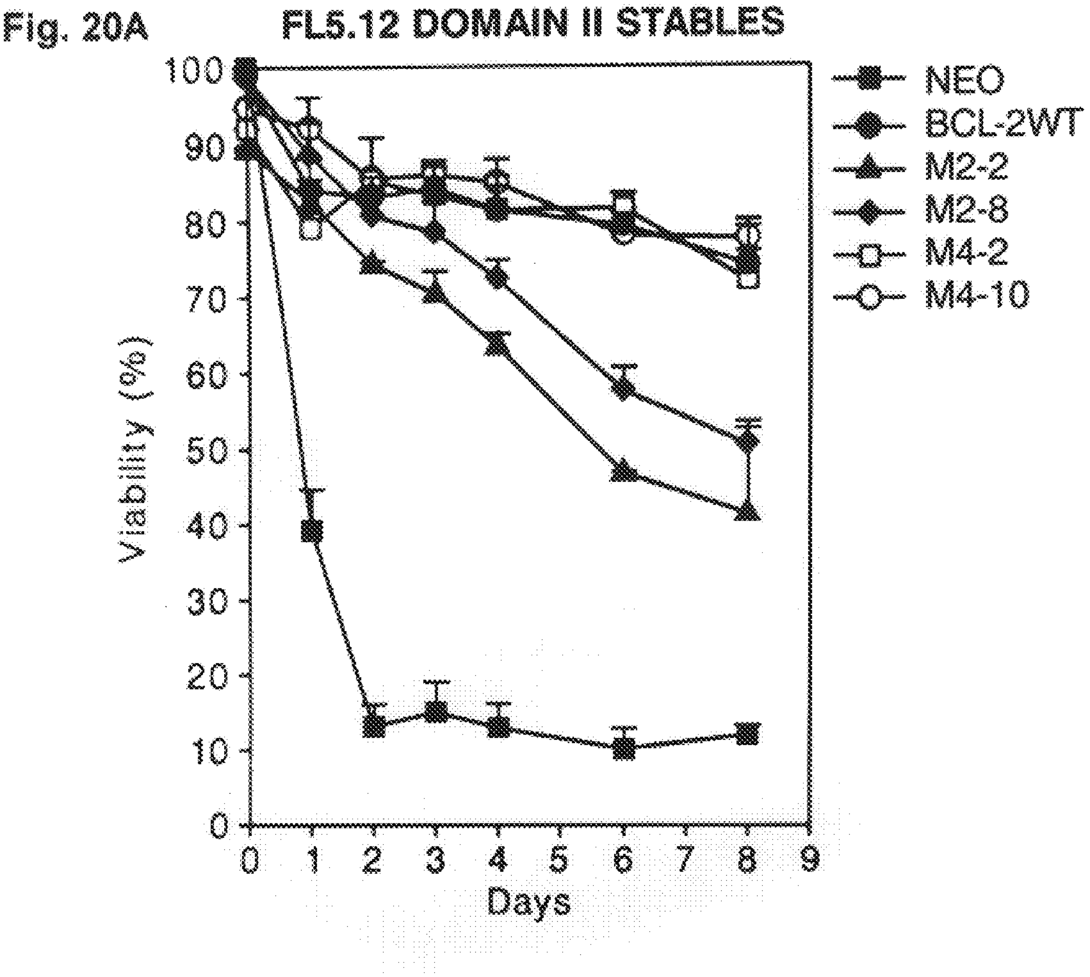
FIG. 20 demonstrates the cell death response in cells with domain II Bcl-2 mutants and 2 immunoprecipitations of radiolabeled transfected cells.
Figure 20B:
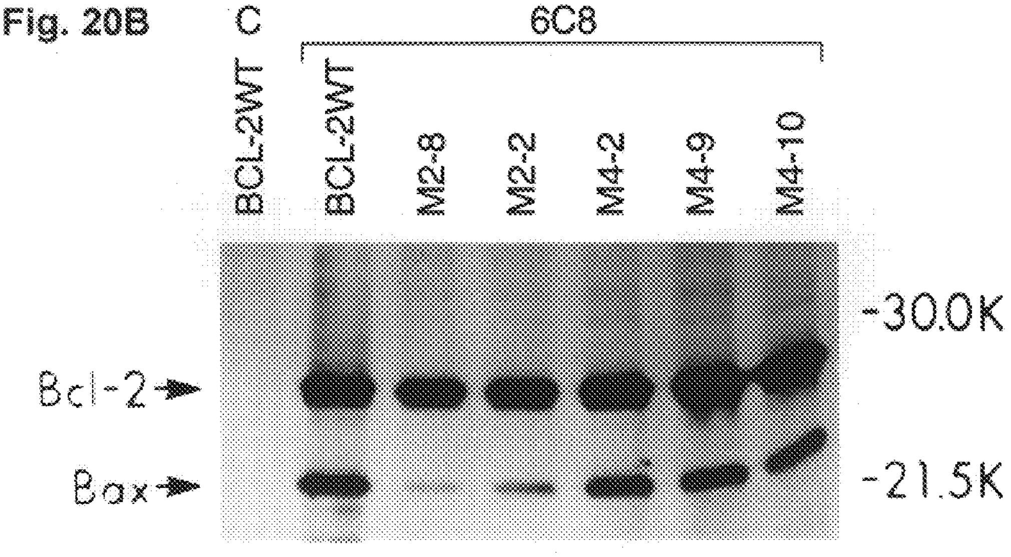

FIG. 20 tests the death responses of FL5.12 cells in A and 2B4 cells in C which bear the domain II mutants. The M3 and M5 mutations had no effects upon the cell death pattern of either FL5.12 or 2B4. Thus, not all conserved amino acids within domain II mediate any functional difference in the Bcl-2 molecule. However, mutations of the QDN in the M2 set of mutants do disturb Bcl-2 function. However, the whole QDN has to be eliminated in that the single substitution of M4 is not sufficient for an effect. Panels B and D are the primary immunoprecipitants of these mutated molecules. They prove that the M2 mutations which partially destroy Bcl-2 function have a reduced association with Bax. However the M4 mutations which function normally has a full association with Bax. Thus, even changes in domain II which affect Bcl-2 function appears to be mediated through its loss of interaction with the Bax molecule.

Figure 21A:
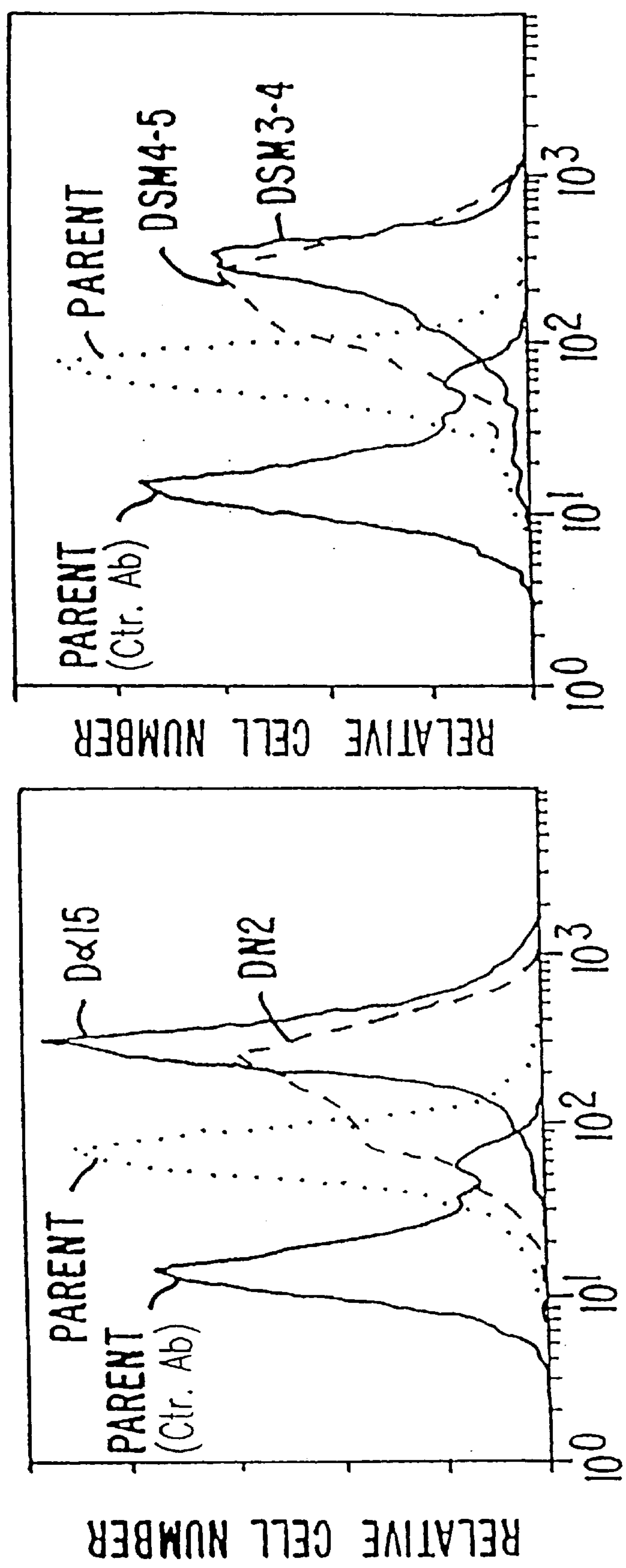
FIG. 21 shows cells that have two expression constructs and indicates the effect of Bcl-2 domain I mutations on homodimerization and heterodimerization.
Figure 21B:
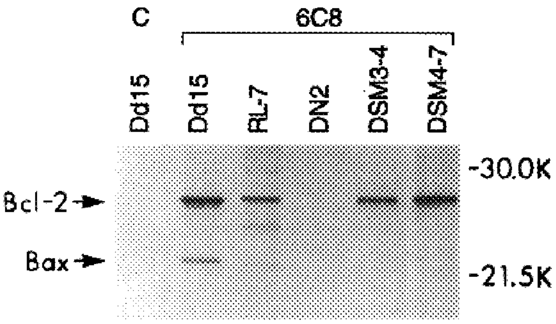
Figure 21C:
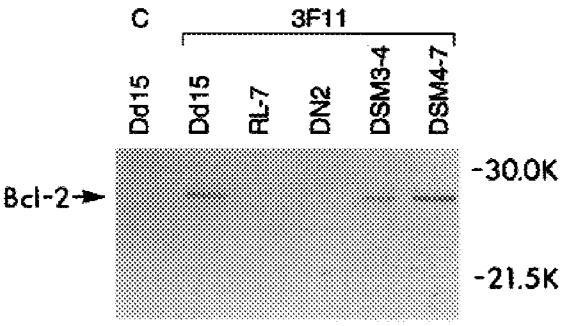

In FIG. 21 cells are created that bear two expression constructs. The Dα15 cell line is an FL5.12 bearing human Bcl-2 wild-type and mouse Bcl-2 wild-type vector. The DN2 bears a control Neomycin resistant expression vector and mouse Bcl-2 wild-type vector. The clone DSM4-5 contains mutant Bcl-2 of domain I and a mouse Bcl-2 wild-type whereas the DSM-4 contains another Bcl-2 mutant of human origin with mouse Bcl-2 wild-type. The flow of cytometry histograms in FIG. 21 denote that the double transfectants bear comparable levels of the mouse Bcl-2 wild-type protein. FIGS. 21B and C prove that the mutations of Bcl-2 that interfere with its capacity to associate with Bax still allow the formation of Bcl-2 homodimers. In FIG. 21B we see a primary immunoprecipitation of either wild-type human Bcl-2 or the mutated human Bcl-2 in which the 3-4 and 4-7 mutants have no associated Bax. Those immunoprecipitations are then developed by Western blot analysis with an anti-mouse Bcl-2 antibody. Both the wild-type human Bcl-2 as well as the two mutants mI 3-4 and mI 4-7 both associate with the wild-type mouse Bcl-2. Moreover, cross linking experiments indicate the capacity of Bcl-2 to homodimerize as well as heterodimerize. The Bcl-2 homodimers are seen with mI3-4 and mI4-7 as well.

The results of this data firmly establishes that agents that disrupt the capacity of Bcl-2 to interact with Bax will eliminate the death repressor activity. Such cells are very vulnerable to programmed cell death. Consequently any therapeutic strategy that eliminates this protein-protein heterodimerzation would be a fundamental and exceptionally successful mechanism to kill cells. Such an approach has importance for cancer therapy, the elimination of autoreactive cells in autoimmunity, and the elimination of hyperplasias in a variety of pathologic hypertrophies such as benign prostatic hypertrophy, lymphoproliferative diseases and the like.

These have not only been created in vivo mammalian cell line systems as screening reagents but we have also created an in vitro protein-protein association assay as well as a yeast two hybrid system assay for screening chemical compounds and synthetic peptides which would disrupt Bcl-2/Bax interactions. This approach is also being applied to the disruption of interactions between all of these family members which interact through domain I and domain II.

An in vitro protein interaction system has been created in which Bax tagged with glutathione-S-tranferase (GST) and attached to a glutathione bearing bead is interacted with a radiolabeled member of this family such as Bcl-2. In such a system Bcl-2 will associate with Bax and can be precipitated with the bead. This provides a rapid in vitro screening assay in which synthetic peptides which mimic the domain I and domain II structures can be screened for their capacity to disrupt the association of Bcl-2 and Bax and other related family members. Such a system can also be utilized as a rapid through-put to screen selected and random chemical libraries for their capacity to interfere with this interaction.

As a first level of in vivo interference of protein-protein heterodimerization we have created a yeast 2 hybrid system. In this system the Bcl-2AC22 is fused to a gal4 DNA binding domain while the BaxΔC23 is fused to a gal4 activation domain. We have shown that Bcl-2 and Bax interact, heterodimerizing within yeast cells, enabling the activation of a lacZ reporter driven by a ga14 DNA recognition motif. This provides a rapid through-put easily quantifiable, simple spectrophometry assay for therapeutic products that could result in a disruption of Bcl-2/Bax interactions. Successful molecules identified by the in vitro protein-protein interaction or primarily isolated from this assay could be identified.

Ultimately, reagents identified in such systems could be confirmed to be of biologic importance in the mammalian cell lines established. Those include the FL5.12 and 2B4 clones bearing stable transfections of Bcl-2, Bax and their modified analogs. Ultimately, proof of concept on any therapeutic agent could proceed to testing in our in vivo models in which we have transgenic mice overexpressing Bcl-2, or overexpressing Bax.

The present invention thus find wide application to a multitude of treatment regimens and diagnostic uses.

It may be used in any therapy which regulates the ratio of Bcl-2/Bax and will alter the rheostat of a cell's selection of survival versus death. This is a powerful therapeutic modality in which changing the ratio to favor Bax and cell death would be applicable to hyperplasias, hypertrophies, cancers and autoimmunity. Altering the ratio to promote the survival of cells by having Bcl-2 in excess would be a successful strategy in the treatment of neuro-degenerative disease as well as immunodeficiency, ischemia induced injury such as myocardial infarction and neurologic stroke. This would include regulating either Bcl-2 or Bax at the gene transcription level or at the protein half-life or protein modification level.

In this regard, a method for modulating apoptosis of a cell, typically a lymphocyte, is provided by this invention. The method comprises administering to a cell an agent which alters intermolecular binding between Bcl-2 and Bax proteins, typically by inhibiting formation of heteromultimers (e.g., heterodimers) between Bcl-2 and Bax and/or homomultimers of Bcl-2 or Bax. Administration of such agents can selectively inhibit formation of Bax/Bax homodimers or Bax/Bcl-2 heterodimers or higher multimeric forms having biological activity. In one embodiment, the agent is a compound comprising a structure of a Bax protein domain I or domain II polypeptide domain; for example, a polypeptide comprising a Bax domain I or domain II sequence can serve as such an agent if deliverable intracellularly. In an embodiment, the agent is a compound comprising a structure of a Bcl-2 protein domain I or domain II polypeptide domain comprising a sequence variation (e.g., mutation) which reduces the agent's affinity for Bax and which does not substantially reduce the agent's affinity for Bcl-2, whereby the agent competitively inhibits formation of Bcl-2/Bcl-2 homodimers comprising naturally-occurring Bcl-2 but does not substantially inhibit formation of Bcl-2/Bax heterodimers or other heteromultimers.

In another aspect of the invention, the method(s) of modulating apoptosis of a cell by administering an agent which alters intermolecular binding between Bcl-2 and Bax proteins are used to treat a pathological condition in a patient. For example, a patient with a pathological condition wherein abnormal cell proliferation or abnormal cell apoptosis is an underlying etiology may be treated by administering an agent which modulates the amount of Bax protein present in cell (e.g., a neoplastic or hyperplastic cell) and/or the ratio of Bax:Bcl-2 proteins in a cell and/or the ratios of Bax/Bax homomultimers, Bax/Bcl-2 heteromultimers, and Bcl-2/Bcl-2 homomultimers.

In another aspect of the invention, an antisense polynucleotide is adminstered to inhibit transcription and/or translation of Bax in a cell.

In another aspect of the invention, a polynucleotide encoding a Bax polypeptide is delivered to a cell, such as an explanted lymphocyte, hematopoietic stem cell, bone marrow cell, and the like. The delivered polynucleotide, typically including an operably-linked promoter (and optionally enhancer) to drive transcription of the Bax-encoding polynucleotide providing expression of a Bax polypeptide, is transferred to the cell to form a stably or transiently transfected cell or homologous recombinant cell wherein Bax protein is expressed under the control of a predetermined transcriptional control sequence. Such transfected cells may be transferred into a patient (e.g., the patient from which the cells were originally explanted) for therapy of a disease, such as a neoplastic disease, and may be used, in one embodiment, to reconstitute hematopoietic cells following chemotherapy/radiotherapy. Such methods may be used, for example, in gene therapy (e.g., to treat neoplasia, hyperplasia, autoimmune diseases, and the like) and Bax polynucleotides may be used in conjunction with suitable gene therapy modalities and delivery systems (e.g., adenoviral vectors and the like).

In another aspect of the invention, transgenic nonhuman animals, such as mice, bearing a transgene encoding a Bax polypeptide and/or a Bcl-2 polypeptide are provided. Such transgenes may be homolgously recombined into the host chromosome or may be non-homlogously integrated. Typically, such transgenes comprise a sequence encoding a Bax polypeptide (or Bcl-2 polypeptide) wherein the polynucleotide sequence is operably linked to a transcription control sequence (e.g., promoter/enhancer) for modulatable (e.g., inducible and/or repressible) or constitutive transcription of the Bax (or Bcl-2) encoding sequence. In one variation, the endogenous Bax gene is functionally disrupted by gene targeting via homologous recombination with a targeting construct. Nonhuman animals harboring such Bax functionally disrupted alleles (i.e., "gene knockouts"), generally homozygous for such Bax knockouts may also comprise a Bax transgene, such that Bax is expressed under the transcriptional control of an operably linked transcriptional control sequence other than the naturally occurring transcriptional control sequence of the nonhuman animal's endogenous Bax gene.

The invention also provides host cells expressing Bax polypeptides encoded by a polynucleotide other than a naturally-occurring Bax gene of the host cell. An exogenous polynucleotide sequence encoding a Bax polypeptide or portion thereof can be transferred into a host cell and transcribed under the control of a transcriptional control sequence such that a Bax polypeptide is expressed. In one variation, the Bax polypeptide(s) can be recovered from the host cell alone or in conjuction with one or more other polypeptide species associated with it. Such host cells may further comprise a polynucleotide sequence encoding a Bcl-2 polypeptide other than the naturally-occurring Bcl-2 gene of the host cell; such cells may express a Bcl-2 polypeptide and a Bax polypeptide; such cells may further comprise knockout alleles of Bax and/or Bcl-2. In one variation, the host cell is a yeast cell and the Bax and/or Bcl-2 polypeptide is expressed as a fusion protein; one embodiment of this variation employs a yeast two-hybrid expression system.

The invention provides antibodies, both monoclonal antibodies and polyclonal antisera, which specifically bind to a Bax polypeptide with an affinity of about at least $1\times10^7$ $M^{-1}$, typically at least $1\times10^8$ $M^{-1}$ or more.

It may also be used in any therapy which disrupts the Bcl-2/Bax heterodimerization which would lead to the death of cells by the elimination of Bcl-2 death repressor activity. This would include random screens of chemicals, compounds that would be able to do that, as well as peptides which would lead through molecular modeling to organic chemicals that would also disrupt this association.

In this regard, the invention provides screening assays for identifying agents which modulate (e.g., inhibit) binding of a Bax polypeptide to a Bcl-2 polypeptide and/or which modulate (e.g., inhibit) binding of a Bax polypeptide to a Bax polypeptide. The compositions of such screening assays generally comprise a Bax polypeptide and a Bcl-2 polypeptide in a suitable aqueous binding solution or in a cell (e.g., a yeast or mammalian cell, a bacterium, a plant cell); the Bax and Bcl-2 polypeptides generally comprise a domain I sequence and/or a domain II sequence. An agent is added to such a screening assay and the formation of Bax/Bcl-2 heteromultimers (heterodimers) is determined; agents which reduce or argument the formation of Bax/Bcl-2 heteromultimers as compared to a parallel control Bax/Bcl-2 binding reation lacking the agent are thereby identified as Bax/Bcl-2 modulators. Optionally, or alternatively, the capacity of an agent to inhibit or argument formation of Bcl-2/Bcl-2 homomultimers (homodimers) and/or Bax/Bax homomultimers (homodimers) can be measured relative to a control binding reaction lacking the agent; such assays identify Bcl-2 modulators and/or Bax modulators. Agents which selectively or preferentially inhibit Bax/Bcl-2 heteromultimer (homodimer) formation as compared to Bax/Bax or Bcl-2/Bcl-2 homomultimer (homodimer) formation can be identified by the assays.

In another aspect, candidate agents are identified by their ability to block the binding of a Bax polypeptide to a Bcl-2 polypeptide. The Bax polypeptide includes one or more Bcl-2 binding sites at which a Bcl-2 protein specifically binds. One means for detecting binding of a Bax polypeptide to a Bcl-2 polypeptide is to immobilize one of the polypeptide species, such as by covalent or noncovalent chemical linkage to a solid support, and to contact the immobilized Bax (or Bcl-2) polypeptide with a Bcl-2 (or Bax) polypeptide that has been labeled with a detectable marker (e.g., by incorporation of radiolabeled amino acid). Such contacting is typically performed in aqueous conditions which permit binding of a Bax (or Bcl-2) polypeptide to a Bcl-2 (or Bax) polypeptide containing a binding sequence, such as domain I or domain II. Binding of the labeled Bax (or Bcl-2) to the immobilized Bcl-2 (or Bax) is measured by determining the extent to which the labeled polypeptide is immobilized as a result of a specific binding interaction. Such specific binding may be reversible, or may be optionally irreversible if a cross-linking agent is added in appropriate experimental conditions.

In a variation of the invention, polynucleotides of the invention are employed for diagnosis of pathological coditions or genetic disease that involve neoplasia or abnormal apoptosis, and more specifically conditions and diseases that involve alterations in the structure or abundance of Bax.

The invention also provides Bax polynucleotide probes for diagnosis of pathological conditions (e.g., neoplasia, AIDS, hyperplasia, congenital genetic diseases) by detection of Bax mRNA or rearrangements or amplification of the Bax gene in cells explanted from a patient, or detection of a pathognomonic Bax allele (e.g., by RFLP or allele-specific PCR analysis). Typically, the detection will be by in situ hybridization using a labeled (e.g., $^{32}P$, $^{35}S$, $^{14}C$, $^{3}H$, fluorescent, biotinylated, digoxigeninylated) Bax polynucleotide, although Northern blotting, dot blotting, or solution hybridization on bulk RNA or poly $A^+$ RNA isolated from a cell sample may be used, as may PCR amplification using Bax-specific primers. Cells which contain an increased or decreased amount or altered structure of Bax mRNA as compared to cells of the same cell type(s) obtained from a normal undiseased control source will be identified as candidate pathological cells. Similarly, the detection of pathognomonic rearrangements or amplification of the Bax locus or closely linked loci in a cell sample will identify the presence of a pathological condition or a predisposition to developing a pathological condition (e.g., cancer, genetic disease) and may be used for forensic identification of individual identity and paternity.

Polynucleotide sequences encoding Bax are also provided. The characteristics of the cloned sequences are given, including the nucleotide and predicted amino acid sequence in FIGS. 3, 5 and 6. Polynucleotides comprising sequences encoding these amino acid sequences can serve as templates for the recombinant expression of quantities of Bax polypeptides, such as human Bax and murine Bax. Polynucleotides comprising such sequences can also serve as probes for nucleic acid hybridization to detect the transcription and mRNA abundance of Bax mRNA in individual lymphocytes (or other cell types) by in situ hybridization, and in specific lymphocyte populations by Northern blot analysis and/or by in situ hybridization (Alwine et al.(1977) *Proc. Natl. Acad. Sci. U.S.A.* 74: 5350) and/or PCR amplification and/or LCR detection. Such recombinant polypeptides and nucleic acid hybridization probes can be used in conjunction with in vitro screening methods for pharmaceutical agents (e.g., antineoplastic agents, immunomodulators) and for diagnosis and treatment of neoplastic or preneoplastic pathological conditions, genetic diseases, and other pathological conditions.

All publications and patent applications herein are incorporated by reference to the same extent as if each individual publication or patent application was specifically and individually indicated to be incorporated by reference.

Furthermore, the Bcl-2/Bax experimental system serves as a generalizable paradigm for the differential regulation of all molecules that repress or accelerate cell death. The alterations of their inherent ratios or the disruption of their protein-protein interactions as either homodimers or heterodimers reflects a powerful and predicted approach from these experimental data.

The invention being thus described, it will be obvious that the same may be varied in many ways. Such variations are not to be regarded as a departure from the spirit and scope of the is invention, and all such modifications are intended to be included within the scope of the following claims.

What is claimed is:

1. A method for identifying candidate Bax modulatory agents comprising:

combining in aqueous binding conditions an agent, a Bax polypeptide capable of binding to a Bcl-2 polypeptide under the aqueous binding conditions, a Bcl-2 polypeptide capable of binding to a Bax polypeptide under the aqueous binding conditions, wherein said Bax polypeptide is selected from the group consisting of SEQ ID NO:2, SEQ ID NO:3, SEQ ID NO:5, SEQ ID NO:7, SEQ ID NO:8, SEQ ID NO:9, SEQ ID NO:32, BAX analogs with at least 90% sequence identity to said SEQ ID NOs and fragments thereof;

determining whether the agent inhibits formation of Bax/Bcl-2 heterodimers; and identifying agents which inhibit formation of Bax/Bcl-2 heterodimers as candidate Bax modulatory agents.

2. The method of claim 1, wherein the Bax polypeptide is a full-length human Bax α isoform polypeptide of SEQ ID NO:2 or a full-length human Bax β isoform polypeptide of SEQ ID NO:32.

3. The method of claim 1, wherein the Bcl-2 polypeptide is a full-length human Bcl-2 polypeptide.

4. A method for identifying candidate Bax modulatory agents, comprising:

combining in aqueous binding conditions an agent, a Bax polypeptide capable of binding to a Bax polypeptide forming a Bax/Bax homodimer under the aqueous binding conditions, wherein said Bax polypeptide is selected from the group consisting of SEQ ID NO:2, SEQ ID NO:3, SEQ ID NO:5, SEQ ID NO:7, SEQ ID NO:8, SEQ ID NO:9, SEQ ID NO:32, Bax analogs with at least 90% sequence identity to said SEQ ID NOs and fragments thereof; and identifying agents which inhibit formation of the Bax/Bax homodimers as candidate Bax modulatory agents.

5. The method of claim 4, wherein the Bax polypeptide is a full-length human Bax α isoform polypeptide of SEQ ID NO:2 or a full-length human Bax β isoform polypeptide of SEQ ID NO:32.

6. The method according to claim 4, wherein the candidate Bax modulatory agent is not cytotoxic to mammalian cells which do not express detectable amounts of Bax mRNA or protein.

7. A method of screening for candidate Bax-modulating agents comprising:

performing a heterodimerization assay which includes a Bax polypeptide with a Bcl-2 polypeptide and an agent, wherein said Bax polypeptide is selected from the group consisting of SEQ ID NO:2, SEQ ID NO:3, SEQ ID NO:5, SEQ ID NO:7, SEQ ID NO:8, SEQ ID NO:9, SEQ ID NO:32, Bax analogs with at least 90% sequence identity to said SEQ ID NOs and fragments thereof; and determining whether the agent inhibits or augments the heterodimerization.

8. The method of claim 7, wherein the heterodimerization assay comprises an in vitro binding reaction.

9. The method of claim 7, wherein the heterodimerization assay comprises a two-hybrid assay in yeast or an *E. coli*/BCCP interactive system.

10. The method of claim 9, wherein the two-hybrid assay comprises a human Bax polypeptide sequence fused to a GAL4 protein and a human Bcl-2 polypeptide sequence fused to a GAL4 protein.

11. The method of claim 7, wherein a Bax or Bcl-2 polypeptide is immobilized.

12. The method of claim 2, wherein the agent is a peptide having the sequence corresponding to amino acids 106–109 of SEQ ID NO:2 or a compound derived by molecular modeling of this sequence.

13. A method for identifying candidate Bax modulatory agents, comprising:

combining in aqueous binding conditions an agent, a Bax polypeptide capable of binding to a Bax polypeptide forming a Bax/Bax homodimer under the aqueous binding conditions;

determining whether the agent inhibits formation of Bax/Bax homodimers, wherein said Bax polypeptide is selected from the group consisting of SEQ ID NO:2, SEQ ID NO:3, SEQ ID NO:5, SEQ ID NO:7, SEQ ID NO:8, SEQ ID NO:9, SEQ ID NO:32, Bax analogs with at least 90% sequence identity to said SEQ ID NOs and fragments thereof;

combining in aqueous binding conditions an agent, a Bax polypeptide capable of binding to a Bcl-2 polypeptide under the aqueous binding conditions, a Bcl-2 polypeptide capable of binding to a Bax polypeptide under the aqueous binding conditions;

determining whether the agent inhibits or augments the formation of Bax/Bcl-2 heterodimers; and identifying agents which preferentially inhibit formation of Bax/Bcl-2 modulatory agents.

14. The method of claim 13, wherein the binding of Bcl-2 to Bax requires domain I or domain II.

* * * * *

```
                              SEQUENCE LISTING

<160> NUMBER OF SEQ ID NOS: 32

<210> SEQ ID NO 1
<211> LENGTH: 624
<212> TYPE: DNA
<213> ORGANISM: Homo sapiens

<400> SEQUENCE: 1

gaggcggcgg cgggagcggc ggtgatggac gggtccgggg agcagcccag aggcgggggg     60

cccaccagct ctgagcagat catgaagaca ggggcccttt tgcttcaggg tttcatccag    120

gatcgagcag ggcgaatggg gggggaggca cccgagctgg ccctggaccc ggtgcctcag    180

gatgcgtcca ccaagaagct gagcgagtgt ctcaagcgca tcggggacga actggacagt    240

aacatggagc tgcagaggat gattgccgcc gtggacagag actccccccg agaggtcttt    300

ttccgagtgg cagctgacat gttttctgac ggcaacttca actggggccg ggttgtcgcc    360

cttttctact ttgccagcaa actggtgctc aaggccctgt gcaccaaggt gccggaactg    420

atcagaacca tcatgggctg gacattggac ttcctccggg agcggctgtt gggctggatc    480

caagaccagg gtggttggga cggcctcctc tcctactttg ggacgcccac gtggcagacc    540

gtgaccatct ttgtggcggg agtgctcacc gcctcgctca ccatctggaa gaagatgggc    600

tgaggcccca gctgccttgg actg                                           624


<210> SEQ ID NO 2
<211> LENGTH: 192
<212> TYPE: PRT
<213> ORGANISM: Homo sapiens

<400> SEQUENCE: 2

Met Asp Gly Ser Gly Glu Gln Pro Arg Gly Gly Gly Pro Thr Ser Ser
                  5                  10                  15

Glu Gln Ile Met Lys Thr Gly Ala Leu Leu Leu Gln Gly Phe Ile Gln
             20                  25                  30

Asp Arg Ala Gly Arg Met Gly Gly Glu Ala Pro Glu Leu Ala Leu Asp
         35                  40                  45

Pro Val Pro Gln Asp Ala Ser Thr Lys Lys Leu Ser Glu Cys Leu Lys
     50                  55                  60
```

-continued

```
Arg Ile Gly Asp Glu Leu Asp Ser Asn Met Glu Leu Gln Arg Met Ile
 65                  70                  75                  80

Ala Ala Val Asp Arg Asp Ser Pro Arg Glu Val Phe Phe Arg Val Ala
                 85                  90                  95

Ala Asp Met Phe Ser Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
        115                 120                 125

Val Pro Glu Leu Ile Arg Thr Ile Met Gly Trp Thr Leu Asp Phe Leu
    130                 135                 140

Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
            180                 185                 190


<210> SEQ ID NO 3
<211> LENGTH: 192
<212> TYPE: PRT
<213> ORGANISM: Mus musculus

<400> SEQUENCE: 3

Met Asp Gly Ser Gly Glu Gln Leu Gly Ser Gly Gly Pro Thr Ser Ser
                  5                  10                  15

Glu Gln Ile Met Lys Thr Gly Ala Phe Leu Leu Gln Gly Phe Ile Gln
             20                  25                  30

Asp Arg Ala Gly Arg Met Ala Gly Glu Thr Pro Glu Leu Thr Leu Glu
         35                  40                  45

Gln Pro Pro Gln Asp Ala Ser Thr Lys Lys Leu Ser Glu Cys Leu Arg
     50                  55                  60

Arg Ile Gly Asp Glu Leu Asp Ser Asn Met Glu Leu Gln Arg Met Ile
 65                  70                  75                  80

Ala Asp Val Asp Arg Asp Ser Pro Arg Glu Val Phe Phe Arg Val Ala
                 85                  90                  95

Ala Asp Met Phe Ala Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
        115                 120                 125

Val Pro Glu Leu Ile Arg Thr Ile Met Gly Trp Thr Leu Asp Phe Leu
    130                 135                 140

Arg Glu Arg Leu Leu Gly Trp Ile Gln Asp Gln Gly Gly Trp Glu Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
            180                 185                 190


<210> SEQ ID NO 4
<211> LENGTH: 186
<212> TYPE: DNA
<213> ORGANISM: Homo sapiens

<400> SEQUENCE: 4

tgggtgagac tcctcaagcc tcctcacccc caccaccgcg ccctcaccac cgcccctgcc     60
```

-continued

```
ccaccgtccc tgccccccgc cactcctctg ggaccctggg ccttctggag caggtcacag    120

tggtgccctc tccccatctt cagatcatca gatgtggtct ataatgcgtt ttccttacgt    180

gtctga                                                               186


<210> SEQ ID NO 5
<211> LENGTH: 61
<212> TYPE: PRT
<213> ORGANISM: Homo sapiens

<400> SEQUENCE: 5

Trp Val Arg Leu Leu Lys Pro Pro His Pro His His Arg Ala Leu Thr
                5                   10                  15

Thr Ala Pro Ala Pro Pro Ser Leu Pro Pro Ala Thr Pro Leu Gly Pro
            20                  25                  30

Trp Ala Phe Trp Ser Arg Ser Gln Trp Cys Pro Leu Pro Ile Phe Arg
        35                  40                  45

Ser Ser Asp Val Val Tyr Asn Ala Phe Ser Leu Arg Val
    50                  55                  60


<210> SEQ ID NO 6
<211> LENGTH: 126
<212> TYPE: DNA
<213> ORGANISM: Homo sapiens

<400> SEQUENCE: 6

atggacgggt ccggagagca gcccagaggc ggggtttcat ccaggatcga gcagggcgaa     60

tgggggggga ggcacccgag ctggccctgg acccggtgcc tcaggatgcg tccaccaaga    120

agctga                                                               126


<210> SEQ ID NO 7
<211> LENGTH: 41
<212> TYPE: PRT
<213> ORGANISM: Homo sapiens

<400> SEQUENCE: 7

Met Asp Gly Ser Gly Glu Gln Pro Arg Gly Gly Val Ser Ser Arg Ile
                5                   10                  15

Glu Gln Gly Glu Trp Gly Gly Arg His Pro Ser Trp Pro Trp Thr Arg
            20                  25                  30

Cys Leu Arg Met Arg Pro Pro Arg Ser
        35                  40


<210> SEQ ID NO 8
<211> LENGTH: 192
<212> TYPE: PRT
<213> ORGANISM: Mus musculus

<400> SEQUENCE: 8

Met Asp Gly Ser Gly Glu Gln Leu Gly Ser Gly Gly Pro Thr Ser Ser
                5                   10                  15

Glu Gln Ile Met Lys Thr Gly Ala Phe Leu Leu Gln Gly Phe Ile Gln
            20                  25                  30

Asp Arg Ala Gly Arg Met Ala Gly Glu Thr Pro Glu Leu Thr Leu Glu
        35                  40                  45

Gln Pro Pro Gln Asp Ala Ser Thr Lys Lys Leu Ser Glu Cys Leu Arg
    50                  55                  60

Arg Ile Gly Asp Glu Leu Asp Ser Asn Met Glu Leu Gln Arg Met Ile
65                  70                  75                  80
```

-continued

```
Ala Asp Val Asp Thr Asp Ser Pro Arg Glu Val Phe Phe Arg Val Ala
                 85                  90                  95

Ala Asp Met Phe Ala Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
        115                 120                 125

Val Pro Glu Leu Ile Arg Thr Ile Met Gly Trp Thr Leu Asp Phe Leu
    130                 135                 140

Arg Glu Arg Leu Leu Val Trp Ile Gln Asp Gln Gly Gly Trp Glu Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
            180                 185                 190


<210> SEQ ID NO 9
<211> LENGTH: 192
<212> TYPE: PRT
<213> ORGANISM: Homo sapiens

<400> SEQUENCE: 9

Met Asp Gly Ser Gly Glu Gln Pro Arg Gly Gly Gly Pro Thr Ser Ser
                  5                  10                  15

Glu Gln Ile Met Lys Thr Gly Ala Leu Leu Leu Gln Gly Phe Ile Gln
             20                  25                  30

Asp Arg Ala Gly Arg Met Gly Gly Glu Ala Pro Glu Leu Ala Leu Asp
         35                  40                  45

Pro Val Pro Gln Asp Ala Ser Thr Lys Lys Leu Ser Glu Cys Leu Lys
     50                  55                  60

Arg Ile Gly Asp Glu Leu Asp Ser Asn Met Glu Leu Gln Arg Met Ile
 65                  70                  75                  80

Ala Ala Val Asp Thr Asp Ser Pro Arg Glu Val Phe Phe Arg Val Ala
                 85                  90                  95

Ala Asp Met Phe Ser Asp Gly Asn Phe Asn Trp Gly Arg Val Val Arg
            100                 105                 110

Leu Phe Tyr Phe Ala Ser Lys Leu Val Leu Lys Ala Leu Cys Thr Lys
        115                 120                 125

Val Pro Glu Leu Ile Arg Thr Ile Met Gly Trp Thr Leu Asp Phe Leu
    130                 135                 140

Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
            180                 185                 190


<210> SEQ ID NO 10
<211> LENGTH: 239
<212> TYPE: PRT
<213> ORGANISM: Homo sapiens

<400> SEQUENCE: 10

Met Ala His Ala Gly Arg Thr Gly Tyr Asp Asn Arg Glu Ile Val Met
                  5                  10                  15

Lys Tyr Ile His Tyr Lys Leu Ser Gln Arg Gly Tyr Glu Trp Asp Ala
             20                  25                  30
```

-continued

```
Gly Asp Val Gly Ala Ala Pro Pro Gly Ala Ala Pro Ala Pro Gly Ile
         35                  40                  45

Phe Ser Ser Gln Pro Gly His Thr Pro His Pro Ala Ala Ser Arg Asp
     50                  55                  60

Pro Val Ala Arg Thr Ser Pro Leu Gln Thr Pro Ala Ala Pro Gly Ala
 65                  70                  75                  80

Ala Ala Gly Pro Ala Leu Ser Pro Val Pro Pro Val Val His Leu Thr
                 85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Gly His Lys
225                 230                 235


<210> SEQ ID NO 11
<211> LENGTH: 236
<212> TYPE: PRT
<213> ORGANISM: Mus musculus

<400> SEQUENCE: 11

Met Ala Gln Ala Gly Arg Thr Gly Tyr Asp Asn Arg Glu Ile Val Met
                  5                  10                  15

Lys Tyr Ile His Tyr Lys Leu Ser Gln Arg Gly Tyr Glu Trp Asp Ala
             20                  25                  30

Gly Asp Ala Asp Ala Ala Pro Leu Gly Ala Ala Pro Thr Pro Gly Ile
         35                  40                  45

Phe Ser Phe Gln Pro Glu Ser Asn Pro Met Pro Ala Val His Arg Glu
     50                  55                  60

Met Ala Ala Arg Thr Ser Pro Leu Arg Pro Leu Val Ala Thr Ala Gly
 65                  70                  75                  80

Pro Ala Leu Ser Pro Val Pro Pro Cys Val His Leu Thr Leu Arg Arg
                 85                  90                  95

Ala Gly Asp Asp Phe Ser Arg Arg Tyr Arg Arg Asp Phe Ala Glu Met
            100                 105                 110

Ser Ser Gln Leu His Leu Thr Pro Phe Thr Ala Arg Gly Arg Phe Ala
        115                 120                 125

Thr Val Val Glu Glu Leu Phe Arg Asp Gly Val Asn Trp Gly Arg Ile
    130                 135                 140

Val Ala Phe Phe Glu Phe Gly Gly Val Met Cys Val Glu Ser Val Asn
145                 150                 155                 160

Arg Glu Met Ser Pro Leu Val Asp Asn Ile Ala Leu Trp Met Thr Glu
```

-continued

```
            165                 170                 175

Tyr Leu Asn Arg His Leu His Thr Trp Ile Gln Asp Asn Gly Gly Trp
            180                 185                 190

Asp Ala Phe Val Glu Leu Tyr Gly Pro Ser Met Arg Pro Leu Phe Asp
        195                 200                 205

Phe Ser Trp Leu Ser Leu Lys Thr Leu Leu Ser Leu Pro Trp Val Gly
    210                 215                 220

Ala Cys Ile Thr Leu Gly Ala Tyr Leu Gly His Lys
225                 230                 235


<210> SEQ ID NO 12
<211> LENGTH: 21
<212> TYPE: PRT
<213> ORGANISM: Homo sapiens

<400> SEQUENCE: 12

Glu Glu Leu Phe Phe Arg Asp Gly Val Asn Trp Gly Arg Ile Val
                 5                  10                  15

Ala Phe Phe Glu Gly Gly
                 20


<210> SEQ ID NO 13
<211> LENGTH: 23
<212> TYPE: PRT
<213> ORGANISM: Homo sapiens

<400> SEQUENCE: 13

Ala Asp Met Phe Phe Ser Asp Gly Asn Phe Asn Trp Gly Arg Val Val
                 5                  10                  15

Ala Leu Phe Tyr Phe Ala Ser
             20


<210> SEQ ID NO 14
<211> LENGTH: 23
<212> TYPE: PRT
<213> ORGANISM: Mus musculus

<400> SEQUENCE: 14

Ile His Val Phe Phe Ser Asp Gly Val Thr Asn Trp Gly Arg Ile Val
                 5                  10                  15

Thr Leu Ile Ser Phe Gly Ala
             20


<210> SEQ ID NO 15
<211> LENGTH: 21
<212> TYPE: PRT
<213> ORGANISM: African Swine Fever Virus
<220> FEATURE:
<221> NAME/KEY: SITE
<222> LOCATION: 5
<223> OTHER INFORMATION: Amino acid is either K (Lys) or R (Arg)

<400> SEQUENCE: 15

Thr Glu Leu Phe Xaa Asp Leu Ile Asn Trp Gly Arg Ile Cys Gly Phe
                 5                  10                  15

Ile Val Phe Ser Ala
             20


<210> SEQ ID NO 16
<211> LENGTH: 21
<212> TYPE: PRT
<213> ORGANISM: Epstein Barr Virus
```

-continued

<400> SEQUENCE: 16

Leu Glu Ile Phe His Arg Gly Asp Pro Ser Leu Gly Arg Ala Leu Ala
1               5                   10                  15

Trp Met Ala Cys Met
            20

<210> SEQ ID NO 17
<211> LENGTH: 23
<212> TYPE: PRT
<213> ORGANISM: Homo sapiens

<400> SEQUENCE: 17

Arg His Leu His Thr Trp Thr Gln Asp Asn Gly Gly Trp Asp Ala Phe
                5                   10                  15

Val Glu Leu Tyr Gly Pro Ser
            20

<210> SEQ ID NO 18
<211> LENGTH: 23
<212> TYPE: PRT
<213> ORGANISM: Homo sapiens

<400> SEQUENCE: 18

Glu Arg Leu Leu Gly Trp Ile Gln Asp Gln Gly Gly Trp Asp Leu Leu
                5                   10                  15

Ser Gly Tyr Phe Gly Thr Pro
            20

<210> SEQ ID NO 19
<211> LENGTH: 22
<212> TYPE: PRT
<213> ORGANISM: Mus musculus

<400> SEQUENCE: 19

Arg Thr Lys Arg Asp Trp Leu Val Lys Gln Arg Gly Trp Asp Gly Phe
                5                   10                  15

Val Glu Phe Phe His Val
            20

<210> SEQ ID NO 20
<211> LENGTH: 23
<212> TYPE: PRT
<213> ORGANISM: African Swine Fever Virus

<400> SEQUENCE: 20

His Asn Leu Leu Pro Trp Met Ile Ser His Gly Gly Gln Glu Glu Phe
                5                   10                  15

Leu Ala Phe Ser Leu His Ser
            20

<210> SEQ ID NO 21
<211> LENGTH: 23
<212> TYPE: PRT
<213> ORGANISM: Epstein Barr Virus

<400> SEQUENCE: 21

Glu Gly Leu Asp Gly Trp Ile His Gln Gln Gly Gly Trp Ser Thr Leu
                5                   10                  15

Ile Glu Asp Asn Ile Pro Gly
            20

-continued

<210> SEQ ID NO 22
<211> LENGTH: 15
<212> TYPE: PRT
<213> ORGANISM: Homo sapiens

<400> SEQUENCE: 22

Glu Glu Leu Phe Arg Asp Gly Val Asn Trp Gly Arg Ile Val Ala
5 10 15

<210> SEQ ID NO 23
<211> LENGTH: 15
<212> TYPE: PRT
<213> ORGANISM: variant Homo sapiens

<400> SEQUENCE: 23

Glu Glu Leu Ala Ala Ala Ala Val Asn Trp Gly Arg Ile Val Ala
5 10 15

<210> SEQ ID NO 24
<211> LENGTH: 15
<212> TYPE: PRT
<213> ORGANISM: variant Homo sapiens

<400> SEQUENCE: 24

Glu Glu Leu Phe Arg Asp Gly Val Asn Ala Ala Ala Ile Val Ala
5 10 15

<210> SEQ ID NO 25
<211> LENGTH: 15
<212> TYPE: PRT
<213> ORGANISM: variant Homo sapiens

<400> SEQUENCE: 25

Glu Glu Leu Phe Arg Asp Gly Val Asn Trp Ala Arg Ile Val Ala
5 10 15

<210> SEQ ID NO 26
<211> LENGTH: 15
<212> TYPE: PRT
<213> ORGANISM: variant Homo sapiens

<400> SEQUENCE: 26

Glu Glu Leu Phe Arg Asp Gly Val Asn Trp Glu Arg Ile Val Ala
5 10 15

<210> SEQ ID NO 27
<211> LENGTH: 15
<212> TYPE: PRT
<213> ORGANISM: Homo sapiens

<400> SEQUENCE: 27

Trp Ile Gln Asp Asn Gly Gly Trp Asp Ala Phe Val Glu Leu Tyr
5 10 15

<210> SEQ ID NO 28
<211> LENGTH: 15
<212> TYPE: PRT
<213> ORGANISM: variant Homo sapiens

<400> SEQUENCE: 28

Trp Ile Leu Ala Ala Gly Gly Trp Asp Ala Phe Val Glu Leu Tyr
5 10 15

<210> SEQ ID NO 29

-continued

<211> LENGTH: 15
<212> TYPE: PRT
<213> ORGANISM: variant Homo sapiens

<400> SEQUENCE: 29

```
Trp Ile Gln Asp Ala Gly Gly Trp Asp Ala Phe Val Glu Leu Tyr
                  5                  10                  15
```

<210> SEQ ID NO 30
<211> LENGTH: 11
<212> TYPE: PRT
<213> ORGANISM: variant Homo sapiens

<400> SEQUENCE: 30

```
Trp Ile Gln Asp Asn Gly Phe Val Glu Leu Tyr
                  5                  10
```

<210> SEQ ID NO 31
<211> LENGTH: 15
<212> TYPE: PRT
<213> ORGANISM: variant Homo sapiens

<400> SEQUENCE: 31

```
Trp Ile Gln Asp Asn Gly Gly Trp Asp Ala Phe Val Ala Leu Tyr
                  5                  10                  15
```

<210> SEQ ID NO 32
<211> LENGTH: 218
<212> TYPE: PRT
<213> ORGANISM: Homo sapiens

<400> SEQUENCE: 32

```
Met Asp Gly Ser Gly Glu Gln Pro Arg Gly Gly Gly Pro Thr Ser Ser
                  5                  10                  15

Glu Gln Ile Met Lys Thr Gly Ala Leu Leu Gln Gly Phe Ile Gln
              20                  25                  30

Asp Arg Ala Gly Arg Met Gly Gly Glu Ala Pro Glu Leu Ala Leu Asp
          35                  40                  45

Pro Val Pro Gln Asp Ala Ser Thr Lys Lys Leu Ser Glu Cys Leu Lys
     50                  55                  60

Arg Ile Gly Asp Glu Leu Asp Ser Asn Met Glu Leu Gln Arg Met Ile
 65                  70                  75                  80

Ala Ala Val Asp Arg Asp Ser Pro Arg Glu Val Phe Phe Arg Val Ala
                 85                  90                  95

Ala Asp Met Phe Ser Asp Gly Asn Phe Asn Trp Gly Arg Val Val Ala
             100                 105                 110

Leu Phe Tyr Phe Ala Ser Lys Leu Val Leu Lys Ala Leu Cys Thr Lys
        115                 120                 125

Val Pro Glu Leu Ile Arg Thr Ile Met Gly Trp Thr Leu Asp Phe Leu
    130                 135                 140

Arg Glu Arg Leu Leu Gly Trp Ile Gln Asp Gln Gly Gly Trp Val Arg
145                 150                 155                 160

Leu Leu Lys Pro Pro His Pro His His Arg Ala Leu Thr Thr Ala Pro
                165                 170                 175

Ala Pro Pro Ser Leu Pro Pro Ala Thr Pro Leu Gly Pro Trp Ala Phe
```

-continued

```
          180                 185                 190

Trp Ser Arg Ser Gln Trp Cys Pro Leu Pro Ile Phe Arg Ser Ser Asp
        195                 200                 205

Val Val Tyr Asn Ala Phe Ser Leu Arg Val
    210                 215
```